United States Patent [19]

Burnett et al.

[11] Patent Number: 5,688,787

[45] Date of Patent: Nov. 18, 1997

[54] SUBSTITUTED β-LACTAM COMPOUNDS USEFUL AS HYPOCHLESTEROLEMIC AGENTS AND PROCESSES FOR THE PREPARATION THEREOF

[75] Inventors: Duane A. Burnett, Fanwood; John W. Clader, Cranford; Sundeep Dugar, Parlin; Wayne Vaccaro, Princeton, all of N.J.

[73] Assignee: Schering Corporation, Kenilworth, N.J.

[21] Appl. No.: 588,785

[22] Filed: Jan. 19, 1996

Related U.S. Application Data

[63] Continuation of Ser. No. 178,312, filed as PCT/US92/05972, Jul. 21, 1992, which is a continuation-in-part of Ser. No. 734,426, Jul. 23, 1991, abandoned, and Ser. No. 734,652, Jul. 23, 1991, abandoned.

[51] Int. Cl.$^6$ .............. A61K 31/395; C07D 205/08; C07D 403/10; C07D 401/04
[52] U.S. Cl. ............................ 514/210; 540/200
[58] Field of Search ............ 514/210; 540/200

[56] References Cited

U.S. PATENT DOCUMENTS

| | | | |
|---|---|---|---|
| 4,166,907 | 9/1979 | Krapcho | 540/200 |
| 4,260,743 | 4/1981 | Bose | 540/364 |
| 4,834,846 | 5/1989 | Abramaer | 540/200 |
| 4,983,597 | 1/1991 | Yang et al. | 514/210 |
| 5,030,628 | 7/1991 | Joyeau et al. | 514/210 |
| 5,306,817 | 4/1994 | Thiruvengadam | 540/200 |

FOREIGN PATENT DOCUMENTS

| | | |
|---|---|---|
| 199630 | 10/1986 | European Pat. Off. |
| 264231 | 4/1988 | European Pat. Off. |
| 337549 | 10/1989 | European Pat. Off. |
| 365364 | 4/1990 | European Pat. Off. |
| 375527 | 6/1990 | European Pat. Off. |
| 462667 | 12/1991 | European Pat. Off. |
| 481671 | 4/1992 | European Pat. Off. |

OTHER PUBLICATIONS

Ram et al, *Indian J. Chem.*, Sect. B, 29B, 12(1990), pp. 1134–1137.

Oppolzer et al, *Tet. Lett.*, 25(1984), pp. 5885–5888.

Derwent Abstract of JP 61-057,580 (1986).

Derwent Abstract of JP 62-081,368 (1987).

Derwent Abstract of JP 61-280,295 (1986).

Derwent Abstract of JP 56-125,360 (1981).

Derwent Abstract of JP 56-061,352 (1981).

*Primary Examiner*—Mark L. Berch
*Attorney, Agent, or Firm*—Anita W. Magatti; Eric S. Dicker

[57] ABSTRACT

Novel compounds of the formula

I wherein

A is —CH=CH—B; —C≡C—B; —($CH_2$)$_p$—X—B, and X is a bone, —NH— or —S(O)$_{0-2}$—; optionally substituted heteroaryl or benzofused heteroaryl; —C(O)—B; or —($CH_2$)$_k$—N⟨ ⟩$R_{13}$, D is B'—($CH_2$)$_m$C(O)—, B'—($CH_2$)$_q$—, B'—($CH_2$)$_e$—Z—($CH_2$)$_r$, wherein Z is —O—, —C(O)—, phenylene, —NR$_8$— or —S(O)$_{0-2}$—, B'—(alkenylene)—; B'—(alkadienylene)—; B'—($CH_2$)$_f$—Z—(alkenylene), B'—($CH_2$)$_f$—V—($CH_2$)$_g$—, wherein V is cycloalkylene, B'—($CH_2$)$_f$—V—(alkenylene) or B'—(alkenylene)—V—($CH_2$)$_f$—, B'—($CH_2$)$_a$—Z—($CH_2$)$_b$—V—($CH_2$)$_d$—, T—($CH_2$)$_s$—, wherein T is cycloalkyl; naphthylmethyl or optionally substituted heteroarylmethyl;

B is optionally substituted phenyl;

B' is naphthyl, optionally substituted heteroaryl or optionally substituted phenyl;

R is hydrogen, fluoro, alkyl, alkenyl, alkynyl, or B—($CH_2$)$_n$—;

R$_4$ is optionally substituted phenyl, indanyl, benzofuranyl, tetrahydronaphthyl, pyridyl, pyrazinyl, pyrimidinyl or quinolyl; are disclosed, the method of using compounds of the formula II

II wherein

R$_{20}$ is optionally substituted phenyl, naphthyl, heteroaryl, or benzofused heteroaryl, R$_{21}$, R$_{22}$ and R$_{23}$ are H or R$_{20}$;

E, F and G are independently a bond; cycloalkylene; alkylene; alkenylene; alkynylene; a substituted alkylene, alkenylene or alkynylene chain; an interrupted alkylene, alkenylene or alkynylene chain; or an interrupted alkylene, alkenylene or alkynylene chain substituted by one or more substituents; or one of R$_{21}$—E and R$_{22}$—F is selected from the group consisting of halogeno, OH, alkoxy, —OC(O)R$_5$, —NR$_{10}$R$_{11}$, —SH or —S(alkyl);

R$_5$ is alkyl, phenyl, R$_{14}$-phenyl, benzyl or R$_{14}$-benzyl;

R$_{10}$ and R$_{11}$ are independently selected from H and lower alkyl, or a pharmaceutically acceptable salt thereof, in a pharmaceutically aceptable carrier as hypocholesterolemic agents is also disclosed.

7 Claims, No Drawings

SUBSTITUTED β-LACTAM COMPOUNDS USEFUL AS HYPOCHLESTEROLEMIC AGENTS AND PROCESSES FOR THE PREPARATION THEREOF

The present application is a continuation of U.S. application Ser. No. 08/178,312, filed Jan. 11, 1994, which is the United States nation application corresponding to International application No. PCT/US 92/05972, filed Jul. 21, 1992 and designating the United States, which PCT application is in turn a continuation-in-part of U.S. application Ser. Nos. 07/734,426 and U.S. application Ser. No. 07/734,652, both filed Jul. 23, 1991, both abandoned, the benefit of which applications are claimed pursuant to the provisions of 35 U.S.C. 120,363 and 365 (C).

BACKGROUND OF THE INVENTION

The present invention relates to substituted β-lactams useful as hypocholesterolemic agents in the treatment and prevention of atherosclerosis and to processses for preparing β-lactams.

Atherosclerotic coronary heart disease represents the major cause for death and cardiovascular morbidity in the western world. Risk factors for atherosclerotic coronary heart disease include hypertension, diabetes mellitus, family history, male sex, cigarette smoking and serum cholesterol. A total cholesterol level in excess of 225–250 mg/dl is associated with significant elevation of risk.

Cholesteryl esters are a major component of atherosclerotic lesions and the major storage form of cholesterol in arterial wall cells. Formation of cholesteryl esters is also a key step in the intestinal absorption of dietary cholesterol. The intracellular esterification of cholesterol is catalyzed by the enzyme acyl CoA:cholesterol acyl transferase (ACAT, EC 2.3.1.26). Thus, inhibition of ACAT is likely to inhibit the progression of atherosclerotic lesion formation, decrease the accumulation of cholesteryl esters in the arterial wall, and block the intestinal absorption of dietary cholesterol.

A few β-lactam compounds have been reported as being useful in lowering cholesterol and/or in inhibiting the formation of cholesterol-containing lesions in mammalian arterial walls. U.S. Pat. No. 4,983,597 discloses N-sulfonyl-2-azetidinones as anticholesterolemic agents and Ram, et al., in *Indian J Chem.*, Sect. B. 29B, 12 (1990), p. 1134–7, disclose ethyl 4-(2-oxoazetidin-4-yl)phenoxy-alkanoates as hypolipidemic agents. European Patent Publication 264,231 discloses 1-substituted-4-phenyl-3-(2-oxoalkylidene)-2-azetidinones as blood platelet aggregation inhibitors.

SUMMARY OF THE INVENTION

Novel hypocholesterolemic compounds of the present invention are represented by the formula I

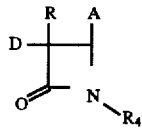

wherein

A is —CH=CH—B;

—C≡C—B;

—$(CH_2)_p$—X—B, wherein p is 0, 1 or 2 and X is a bond, —NH— or —$S(O)_{0-2}$—;

heteroaryl, benzofused heteroaryl, W-substituted heteroaryl or W-substituted benzofused heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, and wherein W is 1–3 substituents on the ring carbon atoms selected from the group consisting of lower alkyl, hydroxy lower alkyl, lower alkoxy, alkoxyalkyl, alkoxyalkoxy, alkoxycarbonylalkoxy, (lower alkoxy-imino)lower alkyl, lower alkanedioyl, lower alkyl lower alkanedioyl, allyloxy, —$CF_3$, —$OCF_3$, benzyl, $R_{14}$-benzyl, benzyloxy, $R_{14}$-benzyloxy, phenoxy, $R_{14}$-phenoxy, dioxolanyl, $NO_2$, —$NR_{10}R_{11}$, $NR_{10}R_{11}$ (lower alkyl)—, $NR_{10}R_{11}$ (lower alkoxy)—, OH, halogeno, —NHC(O)$OR_5$, —NHC(O)$R_5$, $R_6O_2$SNH—, $(R_6O_2S)_2N$—, —$S(O)_2NH_2$, —$S(O)_{0-2}R_{10}$, tert-butyldimethylsilyloxymethyl, —C(O)$R_{12}$ and

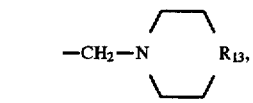

and wherein the substituents on the substituted heteroaryl ring nitrogen atoms, when present, are selected from the group consisting of lower alkyl, lower alkoxy, —C(O)$OR_5$,— C(O)$R_5$, OH, $NR_{10}R_{11}$(lower alkyl)—, $NR_{10}R_{11}$ (lower alkoxy)—, —$S(O)_2NH_2$ and 2-(trimethylsilyl) ethoxymethyl;

—C(O)—B; or

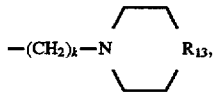

wherein k is 1 or 2;

D is B'—$(CH_2)_mC(O)$—, wherein m is 1, 2, 3, 4 or 5;

B'—$(CH_2)_q$—, wherein q is 2, 3, 4, 5 or 6;

B'—$(CH_2)_e$—Z—$(CH_2)_r$—, wherein Z is —O—, —C(O)—, phenylene, —$NR_8$— or —$S(O)_{0-2}$—, e is 0, 1, 2, 3, 4 or 5 and r is 1, 2, 3, 4 or 5, provided that the sum of e and r is 1,2, 3, 4, 5 or 6;

B'—($C_2$-$C_6$ alkenylene)—; B'—($C_4$-$C_6$ alkadienylene)—;

B'—$(CH_2)_t$—Z—($C_2$-$C_6$ alkenylene)—, wherein Z is as defined above, and wherein t is 0, 1, 2 or 3, provided that the sum of t and the number of carbon atoms in the alkenylene chain is 2, 3, 4, 5 or 6;

B'—$(CH_2)_f$—V—$(CH_2)g$—, wherein V is $C_3$-$C_6$ cycloalkylene, f is 1, 2, 3, 4 or 5 and g is 0, 1, 2, 3, 4 or 5, provided that the sum of f and g is 1, 2, 3, 4, 5 or6;

B'—$(CH_2)_t$—V—($C_2$-$C_6$ alkenylene)— or B'—($C_2$-$C_6$ alkenylene)—V—$(CH_2)_t$—, wherein V and t are as defined above, provided that the sum of t and the number of carbon atoms in the alkenylene chain is 2, 3, 4, 5 or 6;

B'—$(CH_2)_a$—Z—$(CH_2)_b$—V—$(CH_2)_d$—, wherein Z and V are as defined above and a, b and d are independently 0, 1, 2, 3, 4, 5 or 6, provided that the sum of a, b and d is 0, 1, 2, 3, 4, 5 or 6;

T—$(CH_2)_s$—, wherein T is cycloalkyl of 3–6 carbon atoms and s is 1, 2, 3, 4, 5or6; or naphthylmethyl, heteroarylmethyl, or W-substituted heteroarylmethyl, wherein heteroaryl and W are as defined above;

B is

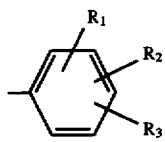

B' is naphthyl, heteroaryl or W-substituted heteroaryl, wherein heteroaryl is as defined above, or

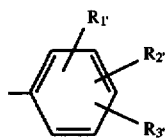

R is hydrogen, fluoro, $C_1$–$C_{15}$ alkyl, $C_1$–$C_{15}$ alkenyl, $C_1$–$C_{15}$ alkynyl, or B—$(CH_2)_h$—, wherein h is 0, 1, 2, or 3;

$R_1$, $R_2$ and $R_3$ are independently selected from the group consisting of H, lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —$CF_3$, —$OCF_3$, benzyl, $R_{14}$-benzyl, benzyloxy, $R_{14}$-benzyloxy, phenoxy, $R_{14}$-phenoxy, dioxolanyl, $NO_2$, —$NR_{10}R_{11}$, $NR_{10}R_{11}$(lower alkyl)—, $NR_{10}R_{11}$ (lower alkoxy)—, OH, o-halogeno, m-halogeno, —NHC(O)O$R_5$, —NHC(O)$R_5$, $R_6O_2$SNH—, $(R_6O_2S)_2$N—, —S(O)$_2$NH$_2$, —S(O)$_{0-2}R_{10}$, tert-butyldimethylsilyloxymethyl, —C(O)$R_{12}$,

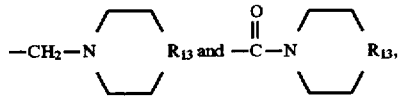

or $R_1$ is hydrogen and $R_2$ and $R_3$, together with adjacent carbon atoms to which they are attached, form a dioxolanyl ring;

$R_1'$, $R_2'$ and $R_3'$ are independently selected from the group consisting of H, lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl alkanedioyl, allyloxy, —$CF_3$, —$OCF_3$, benzyl, $R_{14}$-benzyl, benzyloxy, $R_{14}$-benzyloxy, phenoxy, $R_{14}$-phenoxy, dioxolanyl, $NO_2$, —$NR_{10}R_{11}$, $NR_{10}R_{11}$ (lower alkyl)—, $NR_{10}R_{11}$ (lower alkoxy)—, OH, halogeno, —NHC(O)O$R_5$, —NHC(O)$R_5$, $R_6O_2$SNH—, $(R_6O_2S)_2$N—, —S(O)$_2$NH$_2$, —S(O)$_{0-2}R_{10}$, tert-butyldimethylsilyloxymethyl, —C(O)$R_{12}$,

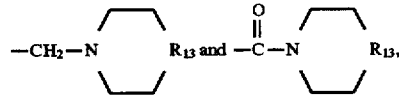

or $R_1'$, is hydrogen and $R_2'$, and $R_3'$, together with adjacent carbon atoms to which they are attached, form a dioxolanyl ring;

$R_4$ is

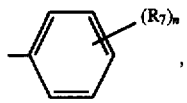

wherein n is 0, 1, 2 or 3, indanyl, benzofuranyl, benzodioxolyl, tetrahydronaphthyl, pyridyl, pyrazinyl, pyrimidinyl or quinolyl;

$R_5$ is lower alkyl, phenyl, $R_{14}$-phenyl, benzyl or $R_{14}$-benzyl;

$R_6$ is OH, lower alkyl, phenyl, benzyl, $R_{14}$-phenyl or $R_{14}$-benzyl;

$R_7$ is lower alkyl, lower alkoxy, OH, halogeno, —$NR_{10}R_{11}$, —NHC(O)O$R_5$, —NHC(O)$R_5$, $NO_2$, —CN, —$N_3$, —SH, —S(O)$_{0-2}$—(lower alkyl), —COO$R_9$, —CONR$_{10}$R$_{11}$, —COR$_{12}$, phenoxy, benzyloxy, —$OCF_3$, or tert-butyldimethylsilyloxy, and where n is 2 or 3, the $R_7$ groups can be the same or different;

$R_8$ is H, lower alkyl, phenyl lower alkyl, or —C(O)$R_9$;

$R_9$ is H, lower alkyl, phenyl or phenyl lower alkyl;

$R_{10}$ and $R_{11}$ are independently selected from H and lower alkyl;

$R_{12}$ is H, OH, alkoxy, phenoxy, benzyloxy,

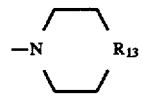

$R_{12}$ is H, OH, alkoxy, phenoxy, benzyloxy, —$NR_{10}R_{11}$, lower alkyl, phenyl or $R_{14}$-phenyl;

$R_{13}$ is —O—, —$CH_2$—, —NH— or —N(lower alkyl)—; and $R_{14}$ is 1–3 groups independently selected from the group consisting of lower alkyl, lower alkoxy, —COOH, $NO_2$, —$NR_{10}R_{11}$, OH or halogeno;

or a pharmaceutically acceptable salt thereof.

Preferred are compounds of formula I wherein R is H. Another group of preferred compounds of formula I is that wherein D is B'—$(CH_2)_q$—, B'—$(CH_2)_e$—Z—$(CH_2)_r$, B'—$(C_2$-$C_6$ alkenylene)—, or B'—$(CH_2)_f$—V—$(CH_2)_g$—, wherein B', Z, V, q, e, r, f, and g are as defined above. A third group of preferred compounds of formula I is that wherein $R_4$ is phenyl, $R_7$-substituted phenyl or indanyl. Still another group of preferred compounds of formula I is that wherein A is —$(CH_2)_p$—X—B, wherein X, B and p are as defined above.

Especially preferred are compounds of formula I wherein D is: B'—$(CH_2)_q$—, wherein B' is phenyl and q is 3 or 4; B'—$(CH_2)_e$—Z—$(CH_2)_r$, wherein B' is p-fluorophenyl or p-methoxyphenyl, e is zero, Z is —O—, and r is 2; B'—$(C_2$-$C_6$ alkenylene)— is 3-phenyl-1-propenyl; or B'—$(CH_2)_f$—V—$(CH_2)_g$—, wherein B' is phenyl, f is 1, V is cyclopropylene, and g is zero. Also especially preferred are compounds of formula I wherein A is —$(CH_2)_p$—X—B wherein p is zero and X is a bond. Preferably $R_1$, $R_2$ and $R_3$ are selected from H, OH, —$NO_2$, lower alkoxy, alkoxyalkoxy, lower alkyl lower alkandioyl, m-halogeno, $NR_{10}R_{11}$(lower alkoxy)—, allyloxy, phenoxy, alkoxycarbonylalkoxy and —C(O)$R_{12}$. Compounds wherein $R_1$ and $R_3$ are each H and $R_2$ is in the para-position are more preferred.

$R_7$ is preferably selected from lower alkyl, lower alkoxy, halogeno, —$OCF_3$, lower alkylthio, —$NR_{10}R_{11}$, —CN, OH, and —COR$_{12}$. More preferred are compounds wherein n is 1 and $R_7$ is in the para-position.

Especially preferred compounds of formula I, wherein R is hydrogen, are shown in the following Table 1:

| D | A | R4 |
|---|---|---|
| $C_6H_5-(CH_2)_3-$ | $p-CH_3O-C_6H_4-$ | $p-CH_3O-C_6H_4-$ |
| $C_6H_5-(CH_2)_4-$ | $p-CH_3O-C_6H_4-$ | $p-CH_3O-C_6H_4-$ |
| $C_6H_5-(CH_2)_3-$ | $p-CH_3O-C_6H_4-$ | $C_6H_5-$ |
| $C_6H_5-(CH_2)_3-$ | $p-OH-C_6H_4-$ | $p-CH_3O-C_6H_4-$ |
| $C_6H_5-(CH_2)_3-$ | $p-CH_3O-C_6H_4-$ | $p-Cl-C_6H_4-$ |
| $C_6H_5-(CH_2)_3-$ | $p-CH_3CH_2-O-C_6H_4-$ | $p-CH_3O-C_6H_4-$ |
| $C_6H_5-(CH_2)_3-$ | $p-CH_3O-C_6H_4-$ | $p-CH_3CH_2O-C_6H_4-$ |
| $p-F-C_6H_4-O-(CH_2)_2-$ | $p-CH_3O-C_6H_4-$ | $p-CH_3O-C_6H_4-$ |
| $C_6H_5-(CH_2)_3-$ | $p-CH_3O-C_6H_4-$ | $p-F-C_6H_4-$ |
| $C_6H_5-(CH_2)_3-$ | $p-CH_3O-C_6H_4-$ | $m-CH_3O-C_6H_4-$ |
| $C_6H_5-(CH_2)_3-$ | $p-CH_3O-C_6H_4-$ | $p-CF_3O-C_6H_4-$ |
| $C_6H_5-(CH_2)_3-$ | $p-CH_3O-C_6H_4-$ | $p-CH_3-C_6H_4-$ |
| $C_6H_5-CH_2-CH=CH-$ | $p-CH_3O-C_6H_4-$ | $p-CH_3O-C_6H_4-$ |
| $C_6H_5-(CH_2)_3-$ | $p-(CH_3(CH_2)_3)-O-C_6H_4-$ | $p-CH_3O-C_6H_4-$ |
| $C_6H_5-(CH_2)_3-$ | $p-CH_3O-C_6H_4-$ | $p-CH_3S-C_6H_4-$ |
| $C_6H_5-(CH_2)_3-$ | $p-(CH_2=CH-CH_2-O)-C_6H_4-$ | $p-CH_3O-C_6H_4-$ |
| $C_6H_5-(CH_2)_3-$ | $p-(C_6H_5-O)-C_6H_4-$ | $p-CH_3O-C_6H_4-$ |
| $C_6H_5-(CH_2)_3-$ | $p-(CH_3CH_2O_2C)-C_6H_4-$ | $p-CH_3O-C_6H_4-$ |
| $C_6H_5-(CH_2)_3-$ | $p-CH_3O-C_6H_4-$ | 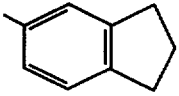 |
| $C_6H_5-(CH_2)_3-$ | $p-(CH_3CH_2CH_2-O)-C_6H_4-$ | $p-CH_3O-C_6H_4-$ |
| $C_6H_5-(CH_2)_5-$ | $p-CH_3O-C_6H_4-$ | $p-CH_3O-C_6H_4-$ |
| $C_6H_5-(CH_2)_3-$ | $p-CH_3O-C_6H_4-$ | $p-((CH_3CH_2)_2N)-C_6H_4-$ |
| $C_6H_5-(CH_2)_3-$ | $p-(CH_3CH_2O)-C_6H_4-$ | $C_6H_5-$ |
| 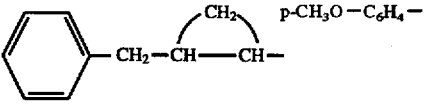 | $p-CH_3O-C_6H_4-$ | $p-CH_3O-C_6H_4-$ |
| $C_6H_5-(CH_2)_3-$ | $p-((CH_3)_2CH-O)-C_6H_4-$ | $p-CH_3O-C_6H_4-$ |
| $p-F-C_6H_4-O-(CH_2)_2-$ | $p-CH_3O-C_6H_4-$ | $C_6H_5-$ |
| $C_6H_5-(CH_2)_3-$ | $p-CH_3O-C_6H_4-$ | 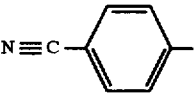 |
| $C_6H_5-(CH_2)_3-$ | $p-(CH_3O_2C)-C_6H_4-$ | $C_6H_5-$ |
| $C_6H_5-(CH_2)_3-$ | $p-CH_3O-C_6H_4-$ | 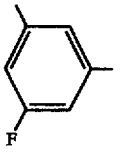 |
| $C_6H_5-(CH_2)_3-$ | 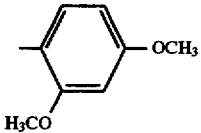 | $p-CH_3O-C_6H_4-$ |
| $C_6H_5-(CH_2)_3-$ | $p-CH_3O-C_6H_4-$ | $p-(H_3CC(O))-C_6H_4-$ |
| $C_6H_5-(CH_2)_3-$ | 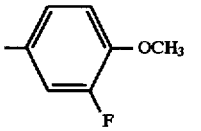 | $p-CH_3O-C_6H_4-$ |
| $C_6H_5-(CH_2)_3-$ | $p-(CH_3OCH_2O)-C_6H_4-$ | $C_6H_5-$ |
| $p-CH_3O-C_6H_4-O-(CH_2)_2-$ | $p-CH_3O-C_6H_4-$ | $C_6H_5-$ |
| $C_6H_5-(CH_2)_3-$ | $p-(CH_3CH_2OC(O)CH_2O)-C_6H_4-$ | $p-CH_3O-C_6H_4-$ |
| $C_6H_5-(CH_2)_3-$ | $p-(CH_3OC(O)-(CH_2)_2-C(O)-O)-C_6H_4-$ | $p-CH_3O-C_6H_4-$ |
| $C_6H_5-(CH_2)_3-$ | $p-((CH_3)_2N-(CH_2)_3-O)-C_6H_4-$ | $p-CH_3O-C_6H_4-$ |
| $C_6H_5-(CH_2)_3-$ | $p-HO-C_6H_4-$ | $p-HO-C_6H_4-$ |

-continued

| D | A | R$_4$ |
|---|---|---|
| (2-naphthylethyl structure) | p-CH$_3$O—C$_6$H$_4$— | C$_6$H$_5$— |

The first-listed compound in the above table having the (3R,4S) absolute stereochemistry is more preferred.

This invention also relates to the use of a novel compound of formula I of the present invention as a hypocholesterolemic agent in a mammal in need of such treatment.

In another aspect, the invention relates to a pharmaceutical composition comprising a novel β-lactam of formula I of the present invention in a pharmaceutically acceptable carrier.

In still another aspect, the present invention relates to a pharmaceutical composition comprising a cholesterol-lowering effective amount of a compound having the structural formula II $$\begin{array}{c} R_{22} \\ | \\ F \\ R_{21}-E \underset{O}{\overset{}{\diagdown}} \underset{N}{\overset{G-R_{23}}{\diagup}} \\ R_{20} \end{array}$$
II wherein R$_{20}$ is phenyl, W-substituted phenyl, naphthyl, W-substituted naphthyl, benzodioxolyl, heteroaryl, W-substituted heteroaryl, benzofused heteroaryl and W-substituted benzofused heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof;

R$_{21}$, R$_{22}$ and R$_{23}$ are independently selected from H or R$_{20}$;

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —CF$_3$, —OCF$_3$, benzyl, R$_{14}$-benzyl, benzyloxy, R$_{14}$-benzyloxy, phenoxy, R$_{14}$-phenoxy, dioxolanyl, NO$_2$, —NR$_{10}$R$_{11}$, NR$_{10}$R$_{11}$(lower alkyl)—, NR$_{10}$R$_{11}$(lower alkoxy)—, OH, halogeno, —NHC(O)OR$_5$, —NHC(O)R$_5$, R$_6$O$_2$SNH—, (R$_6$O$_2$S)$_2$N—, —S(O)$_2$NH$_2$, —S(O)$_{0-2}$R$_{10}$, tert-butyldimethylsilyloxymethyl, —C(O)R$_{12}$, $$-CH_2-N\diagup\diagdown R_{13} \text{ and } -\overset{O}{\overset{\|}{C}}-N\diagup\diagdown R_{13},$$

E, F and G are independently a bond; C$_3$–C$_6$ cycloalkylene; C$_1$–C$_{10}$ alkylene; C$_1$–C$_{10}$ alkenylene; C$_1$–C$_{10}$ alkynylene; an alkylene, alkenylene or alkynylene chain as defined substituted by one or more substituents independently selected from the group consisting of phenyl, W-substituted phenyl, heteroaryl and W-substituted heteroaryl, wherein hetemaryl is as defined above; an alkylene, alkenylene or alkynylene chain as defined interrupted by one or more groups independently selected from the group consisting of —O—, —S—, —SO—, —SO$_2$—, —NR$_8$, —C(O)—, C$_3$–C$_6$ cycloalkylene, phenylene, W-substituted phenylene, heteroarylene and W-substituted heteroarylene; or an interrupted alkylene, alkenylene or alkynylene chain as defined substituted by one or more substituents independently selected from the group consisting of phenyl, W-substituted phenyl, heteroaryl and W-substituted heteroaryl; or one of R$_{21}$-E and R$_{22}$-F is selected from the group consisting of halogeno, OH, lower alkoxy, —OC(O)R$_5$, —NR$_{10}$R$_{11}$, —SH or —S(lower alkyl);

R$_5$ is lower alkyl, phenyl, R$_{14}$-phenyl, benzyl or R$_{14}$-benzyl;

R$_6$ is OH, lower alkyl, phenyl, benzyl, R$_{14}$-phenyl or R$_{14}$-benzyl;

R$_8$ is H, lower alkyl, phenyl lower alkyl or —C(O)R$_9$;

R$_9$ is H, lower alkyl, phenyl or phenyl lower alkyl;

R$_{10}$ and R$_{11}$ are independently selected from H and lower alkyl;

R$_{12}$ is H, OH, alkoxy, phenoxy, benzyloxy, $$-N\diagup\diagdown R_{13},$$

—NR$_{10}$R$_{11}$, lower alkyl, phenyl or R$_{14}$-phenyl;

R$_{13}$ is —O—, —CH$_2$—, —NH— or —N(lower alkyl)—;

R$_{14}$ is 1–3 groups independently selected from the group consisting of lower alkyl, lower alkoxy, —COOH, NO$_2$, —NR$_{10}$R$_{11}$, OH or halogeno;

provided that when G is a bond, R$_{23}$ is not H, and provided that when R$_{23}$ is W-substituted phenyl, W is not p-halogeno;

or a pharmaceutically acceptable salt thereof;

in a pharmaceutically acceptable carrier.

It is noted that novel compounds of formula I are included within the scope of formula II.

Preferred compounds of formula II are those wherein R$_{21}$ is H and E is a bond or lower alkylene, and those wherein R$_{21}$ is phenyl and E is lower alkylene. Also preferred are compounds of formula II wherein R$_{22}$ is H and F is a bond. Another group of preferred compounds of formula II is that wherein G is a bond and R$_{23}$ is phenyl substituted by OH, —NO$_2$, lower alkoxy, alkoxyalkoxy, m-halogeno, lower alkyl lower alkandioyl, NR$_{10}$R$_{11}$(lower alkoxy)—, allyloxy, phenoxy, alkoxycarbonylalkoxy, and —C(O)R$_{12}$. Still another group of preferred compounds of formula II is that wherein R$_{20}$ is phenyl or phenyl substituted by lower alkyl, lower alkoxy, halogeno, —OCF$_3$, lower alkylthio, —NR$_{10}$R$_{11}$, —CN, OH or acetyl.

Certain compounds not within the scope of formula I but within the scope of formula II are novel compounds. Examples of such compounds are represented in the following Table 2

| $R_{21}$—E— | $R_{22}$—F— | $R_{23}$—G— | $R_{20}$— |
|---|---|---|---|
| $C_{10}H_{21}$— | H | $C_6H_5$— | 4-$CH_3O$—$C_6H_4$— |
| $C_{10}H_{21}$— | H | $C_6H_5$— | 2,4,6-tri-$CH_3O$—$C_6H_2$— |
| $C_{10}H_{21}$— | $CH_3CH_2$— | $C_6H_5$— | 4-$CH_3O$—$C_6H_4$— |
| $C_{10}H_{21}$— | $C_6H_5$—$(CH_2)_3$— | $C_6H_5$— | 4-$CH_3O$—$C_6H_4$— |
| $C_{10}H_{21}$— | $CH_3CH_2$— | $C_6H_5$— | 2,4,6-tri-$CH_3O$—$C_6H_2$— |
| $C_{10}H_{21}$— | $CH_3CH_2$— | $C_6H_5$—CH=CH— | 4-$CH_3O$—$C_6H_4$— |
| $C_{10}H_{21}$— | $CH_3$— | $C_6H_5$— | 4-$CH_3O$—$C_6H_4$— |

The present invention also relates to the method of lowering serum cholesterol in a mammal in need of such treatment comprising administering a pharmaceutical composition comprising a compound of formula II in a pharmaceutically acceptable carrier.

The present invention also relates to the use of a compound of formula I or II as an ACAT inhibitor.

The present invention also relates to a stereoselective process for producing β-lactams of formula I, wherein R is hydrogen, and D and A have trans relative stereochemistry, from a hydroxyamide of the formula

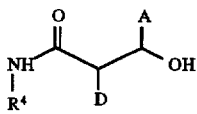

wherein D, A and $R^4$ are as defined above, by cyclizing the hydroxyamide, and wherein the hydroxyamide is prepared from a carboxylic acid $DCH_2COOH$, an aldehyde A—CHO and an amine $R_4NH_2$, wherein D, A and $R^4$ are as defined above, in a process utilizing as a chiral auxiliary an oxazolidinone of the formula

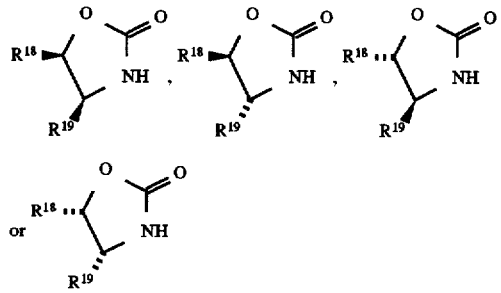

wherein $R^{18}$ and $R^{19}$ are independently selected from the group consisting of: hydrogen, $C_1$-$C_6$ alkyl, phenyl, naphthyl, substituted phenyl, substituted naphthyl, and benzyl, wherein said chiral auxiliary is preferably R-(+)-4-benzyl-oxazolidinone.

This process, designated Method D, for producing compounds of formula I, wherein R is hydrogen, and D and A have trans relative stereochemistry, comprises the steps:

(a) reacting a carboxylic acid of the formula
D—$CH_2COOH$, wherein D is as defined above, with a chlorinating agent;

(b) deprotonating a chiral oxazolidinone, as described above, preferably R-(+)-4-benzyloxazolidinone, with a strong base or a tertiary amine base and treating the resulting anion with the product of step (a);

(c) enolizing the product of step (b) with either:
  (i) a dialkylboron triflate and a tertiary amine base; or
  (ii) $TiCl_4$ and tetramethylethylenediamine (TMEDA) or a mixture of TMEDA and triethylamine;

then condensing with an aldehyde of the formula A—CHO, wherein A is as defined above;

(d) hydrolyzing the product of step (c) with a base and hydrogen peroxide;

(e) condensing the product of step (d) with an amine of the formula $R^4NH_2$, wherein $R^4$ is as defined above, by treating with a dehydrative coupling agent, optionally adding an activating agent;

(f) cyclizing the product of step (e) by reacting the product of step (e) with:
  (i) a dialkylazodicarboxylate and a trialkylphosphine; or
  (ii) a di- or tri-chlorobenzoyl chloride, an aqueous solution of a base and a phase transfer catalyst, then treating the resulting di- or tri-chlorobenzoate with an aqueous solution of a base and a phase transfer catalyst; or
  (iii) a dialkylchlorophosphate,-an aqueous solution of a base and a phase transfer catalyst; or
  (iv) a di- or tri-chlorobenzoyl chloride and a metal hydride.

In another embodiment, the process of this invention provides the steps of producing a β-lactam of formula I, wherein R is hydrogen, and D and A have trans relative stereochemistnJ, from a β-aminoamide derivative of the formula

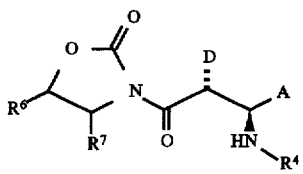

by cyclizing the β-aminoamide, wherein the β-aminoamide is prepared from a carboxylic acid $DCH_2COOH$, and an imine ACH=N—$R^4$, wherein D, A and $R^4$ are as defined above, in a process utilizing as a chiral auxiliary an oxazolidinone of the formula

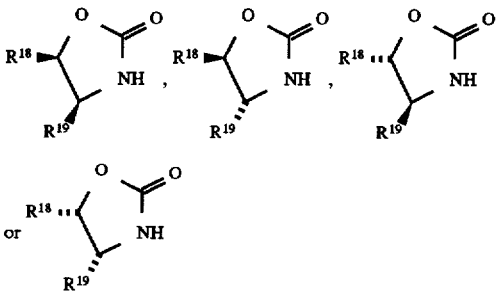

wherein $R^{18}$ and $R^{19}$ are as defined above, and wherein said chiral auxiliary is preferably R-(+)-4-benzyl-oxazolidinone.

This process, designated Method F, for producing compounds of formula I, wherein R is hydrogen, and D and A have trans relative stereochemistry, comprises the steps:

(a) enolizing the product of Method D, step (b) with $TiCl_4$ and tetramethylethylenediamine (TMEDA), then condensing with an imine of the formula A—CH=N—$R^4$, wherein A and $R^4$ are as defined above;

(b) cyclizing the product of step (a) by treating with a strong non-nucleophilic base, preferably sodium bistrimethylsilylamide.

DETAILED DESCRIPTION

As used herein, the term "lower alkyl" means straight or branched alkyl chains of 1 to 6 carbon atoms and "lower alkyoxy" similarly refers to alkoxy groups having 1 to 6 carbon atoms.

"Alkenyl" means straight or branched carbon chains having one or more double bonds in the chain, conjugated or unconjugated, and alkadienyl refers to chains having two double bonds in the chain. Similarly, "alkynyl" means straight or branched carbon chains having one or more triple bonds in the chain.

Where an alkyl, alkenyl or alkynyl chain joins two other variables and is therefore bivalent, the terms alkylene, alkenylene and alkynylene are used.

"Cycloalkyl" means a saturated carbon ring of 3 to 6 carbon atoms, while "cycloalkylene" refers to a corresponding bivalent ring, wherein the points of attachment to other groups include all positional isomers.

"Halogeno" refers to fluorine, chlorine, bromine or iodine radicals.

"Heteroaryl" includes all positional isomers for a given heteroaryl group as defined above, for example 2-pyridyl, 3-pyridyl and 4-pyridyl. Benzofused heteroaryl refers to radicals formed by the bonding of a benzene radical to adjacent carbon atoms on a heteroaryl ring; examples are indolyl, quinolyl, quinazolinyl, quinoxalinyl, benzotriazolyl, indazolyl, benzoxazolyl, benzothienyl and benzofuranyl.

"Phenylene" means a bivalent phenyl group, including ortho, meta and para-substitution and "heteroarylene" similarly means a bivalent heteroaryl group, ioncluding all positional isomers.

"(Lower alkoxyimino)lower alkyl" refers to the group ($C_1$-$C_6$ lower alkoxy)—N=CH—($C_1$-$C_5$ lower alkyl). "Lower alkanedioyl" means radicals of the formula —OC(O)($CH_2$)$_{1-4}$C(O)OH, while "lower alkyl lower alkanedioyl" means radicals of the formula —OC(O)($CH_2$)$_{1-4}$C(O)O—(lower alkyl).

$R_{14}$-benzyl and $R_{14}$-benzyloxy refer to benzyl and benzyloxy radicals which are substituted on the phenyl ring.

"Tertiary amine base" means a trialkylamine, such as triethylamine or diisopropylethylamine, or a nitrogen containing heterocycle, such as pyridine.

"Base" means a metal hydroxide base such as lithium, sodium or potassium hydroxide.

"Strong base" means a non-aqueous base such as a metal hydride or an alkyllithium.

"Metal hydride" means a commercially available metal hydride such as lithium, sodium or potassium hydride "Alkyllithium" means a alkyllithium reagent such as n-butyllithium, s-butyllithium, t-butyllithium or methyllithium.

"Dehydrative coupling agent" means a carbodiimide such as 1-(3'-dimethylaminopropyl)-3-ethylcarbodiimide hydrochloride (DEC) or dicyclohexylcarbodiimide (DCC).

"Activating agent" means an agent used to facilitate the formation of amide bonds such as 1-hydroxybenzotriazole (HOBT) or N-hydroxysuccinimide.

"Halide salt" means a metal salt of a halogen such as sodium, lithium or potassium bromide.

The carbon chains as defined in E, F, and G, when substituted by optionally substituted phenyl or heteroaryl groups, may include independent substitution on different carbon atoms, di-substitution on one carbon atom, or both. One skilled in the art will recognize that the number of double or triple bonds present, the replacement of carbon atoms in the chain and the presence of substitutents on the carbon atoms in the chain are all dependent on the length of the chain: shorter carbon chains cannot accommodate as many double or triple bonds, carbon replacements or substituents as longer carbon chains can. In general, unsaturated carbon chains contain 1 to 4 double or triple bonds, conjugated or non-conjugated. Where carbon atoms are replaced, 1 to 4 replacement groups can be present. Similarly, when carbon atoms in the chain are substituted, 1 to 4 substituents can be present.

Examples of alkyl chains are methyl, ethyl, propyl, butyl and decyl.

Examples of unsaturated E, F and G groups are ethylene and acetylene.

Examples of E, F and G groups Wherein the carbon atoms in the chain are replaced are —$CH_2CH_2O$—, —$OCH_2CH_2$—, —$CH_2O$—, —$CH_2CH_2CH_2O$—, —$CH_2$—O—$CH_2$—, —$CH_2CH_2$—O—$CH_2$, —$CH_2CH_2$—NH—, —$CH_2CH_2$—N($CH_3$)— and —O—$CH_2$C(O)—NH—.

Compounds of the invention have at least one asymmetrical carbon atom and therefore all isomers, including diastereomers and rotational isomers are contemplated as being part of this invention. The invention includes d and l isomers in both pure form and in admixture, including racemic mixtures. Isomers can be prepared using conventional techniques, either by reacting enantiomeric starting materials or by separating isomers of a compound of formula I or II.

Isomers may include geometric isomers, e.g. when E, F or G contains a double bond. All such isomers are contemplated for this invention.

Those skilled in the art will appreciate that for some compounds of formulae I and II, one isomer will show greater pharmacological activity than another isomer.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formulae I and II can be prepared by several known methods, and in particular compounds having trans stereochemistry can be prepared by a novel method D, as disclosed in U.S. Ser. No. 07/734,426, filed Jul. 23, 1991, or novel method F.

Method A:

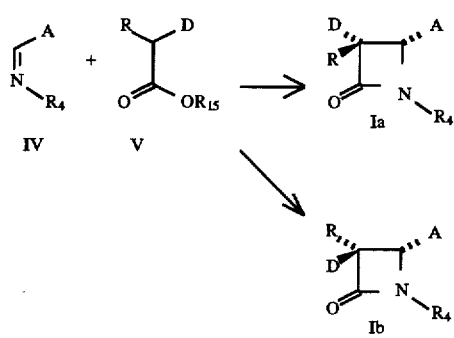

Compounds of formula Ia and Ib, wherein A, D, R and $R_4$ are as defined above, can be prepared by treatment of an ester of formula V, wherein $R_{15}$ is lower alkyl such as ethyl or a chiral moiety such as menthyl or 10-(diisopropylsulfonamido)-isobornyl, with a strong base such as lithium diisopropylamide in a suitable solvent such as tetrahydrofuran (THF) at $-78°$ C. Hexamethylphosphoric triamide (HMPA) may optionally be added as a cosolvent. An imine of formula IV is added and the reaction mixture is warmed to room temperature and the product isolated using conventional purification techniques. When a chiral ester of formula V is used, the resulting compound of formula Ia or Ib is not racetalc.

Method B:

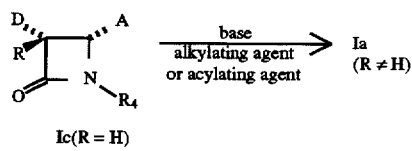

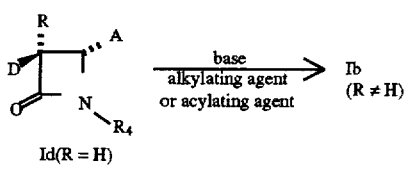

Compounds of formula Ic or Id can be converted to compounds of formula Ia or Ib by treatment with a strong base such as lithium diisopropylamide in a suitable solvent such as THF in the presence or absence of HMPA at $-78°$ C., followed by the addition of an alkylating agent $R-R_{17}$, or an acylating agent such as R—C(O)O—alkyl or R—C(O)Cl, wherein R is as defined above, except that R is not hydrogen, and $R_{17}$ is a leaving group such as bromo or iodo.

Method B':

Trans compounds of formula Id can be converted to the corresponding cis compounds of formula Ic by using Method B, above, but using a proton source such as acetic acid in place of the alkylating agent.

Method C:

Trans compounds of formula Id, wherein R is hydrogen and A, D and $R_4$ are as defined above can be prepared by treating cis compounds of formula Ic with a strong base such as lithium diisopropylamide or potassium t-butoxide in a suitable solvent such as THF. Those skilled in the art will appreciate that since the reaction conditions of Method C can be similar to those of Method A, the conversion of cis to trans sometimes occurs in situ under the conditions of Method A.

Method D

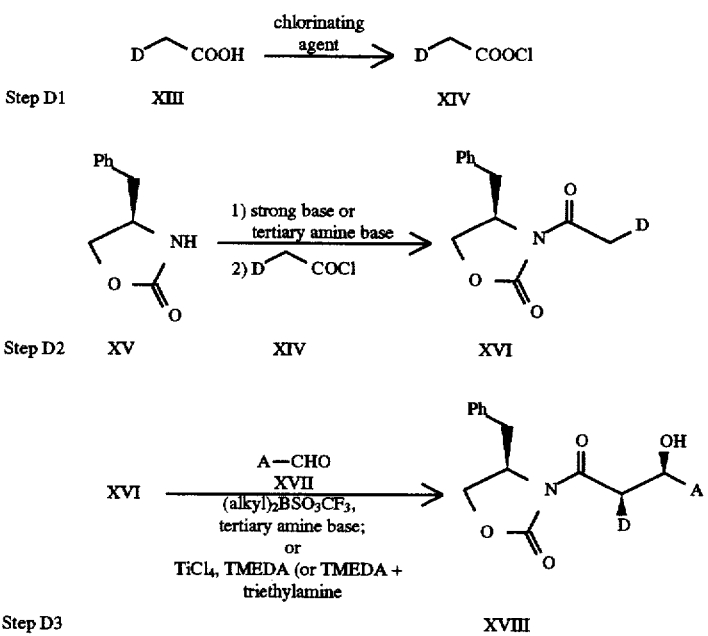

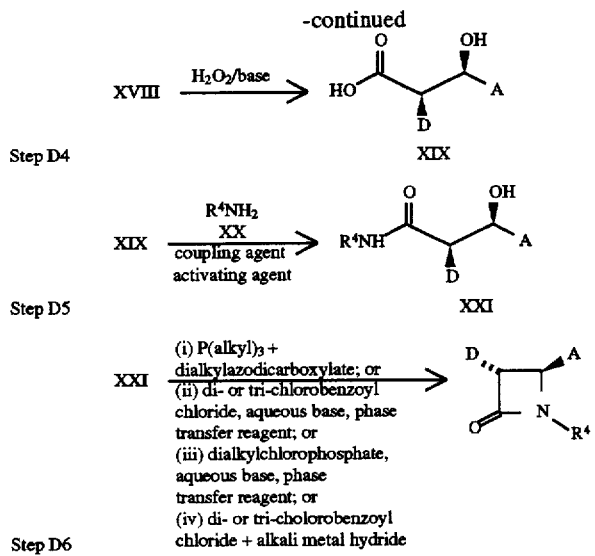

Step D4

Step D5

Step D6

In step D1 of Method D, the carboxylic acid XIII is treated with a chlorinating agent, e.g., thionyl chloride or oxalyl chloride, under a dry atmosphere, neat or in a suitable inert organic solvent, e.g., toluene, at 70° C. to produce compound XIV.

In step D2, compound XV is converted to compound XVI in a two step reaction, first by deprotonating with a strong base, such as an alkyllithium, e.g., n-butyllithium, or metal hydride, e.g., sodium hydride, or a tertiary amine base, such triethylamine, in a suitable anhydrous organic solvent, e.g., dry THF, under a dry, inert atmosphere, e.g., nitrogen, at about 0° C. to about −85° C., preferably about −78° C., over a period of about 30 to about 90 minutes, preferably about 60 minutes, and second by reacting the resulting anion, without isolation, with compound XIV in a suitable anhydrous organic solvent, e.g., dry THF, under a dry, inert atmosphere, e.g., nitrogen, at about −50° C. to about −85° C., preferably about −78° C., over a period of about 30 to about 60 minutes, preferably about 45 minutes, followed by continued reaction at about −10° C. to about 10° C., preferably about 0° C., for a period of about 30 to about 90 minutes, preferably about 60 minutes, then isolating the product, compound XVI, by extraction.

In step D3, compound XVI is treated with a dialkylboron triflate, e.g., di-n-butylborontriflate (Bu$_2$BSO$_3$CF$_3$), in a suitable inert organic solvent, e.g. CH$_2$Cl$_2$, under a dry, inert atmosphere, e.g., nitrogen, at about −60° C. to about 10° C., preferably about −10° C. to about 0° C., for a period of about 10 minutes. A tertiary amine base, e.g., diisopropylethylamine, is added at about −10° C. to about 0° C., preferably about −6° C. to about −3° C., for about 20 to about 40 minutes, preferably about 30 minutes. The mixture is stirred at about −50° C. to about −85° C., preferably about −78° C., for about 20 to about 40 minutes, preferably about 30 minutes, then treated with compound XVII, at about −50° C. to about −85° C., preferably about −78° C., for about 20 to about 40 minutes, preferably about 30 minutes. The mixture is stirred at about −10° C. to about 5° C., preferably about 0° C. for about 30 to about 90 minutes, preferably about 60 minutes, then quenched with an aqueous pH 7 buffer solution, e.g., an aqueous solution of KH$_2$PO$_4$ and NaOH, and treated with methanol, and hydrogen peroxide, preferably 30% hydrogen peroxide, at about −5° C. to about 5° C., preferably about 0° C., for about 1 hour. The product is isolated by extraction and crystallized from a suitable solvent, e.g., hexane/ethyl acetate, to obtain compound XVIII.

Alternatively, step D3 comprises treating compound XVI with titanium tetrachloride (TiCl$_4$), in a suitable inert organic solvent, e.g. CH$_2$Cl$_2$, at about −60° C. to about 0° C., preferably about −25° C. to about −15° C., and most preferably at about −20° C., for a period of about 10 minutes. Tetramethylethylenediamine (TMEDA) or a combination of TMEDA and triethylamine is added slowly over a period of about 10 minutes, while maintaining the temperature at about about −25° C. to about −10° C. The mixture is stirred at about −25° C. to about −10° C., preferably about −15° C. to about −10° C., for a period of 30 to 90 minutes, preferably about 60 minutes, then treated with a compound of the formula XVII. The mixture is stirred at about −25° C. to about −10° C., preferably about −15° C. to about −10° C., for a period of 30 to 90 minutes, preferably about 60 minutes, then stirred for 30 to 60 minutes, preferably about 40 minutes, while warming to about 0° C. to about 10° C., preferably about 10° C. The mixture is quenched with an aqueous solution of tartaric acid, preferably a solution of about 10% tartaric acid in water. The product is then isolated by extraction with a suitable solvent, e.g. ethyl acetate, and recrystallized from a suitable solvent, such as ethyl actetate/hexane, to obtain compound XVIII.

In step D4, compound XVIII is treated with hydrogen peroxide, preferably 30% hydrogen peroxide; in a inert organic solvent, e.g., THF/water, at about −5° C. to about 5° C., preferably about 0° C., for about 10 to about 20 minutes, preferably about 15 minutes, then treated with a base, e.g., lithium hydroxide, at about −5° C. to about 5° C., preferably about 0° C., until no starting material remains, as determined by thin layer chromatography (TLC), in about 2 hours to about 4 hours, preferably about 3 hours. The excess peracid is reduced by slowly adding a solution of sodium sulfite in water to the mixture over a period of about 30 to about 90 minutes, preferably about 70 minutes. The bulk of the solvent is removed under vacuum and the residue diluted with water. Compound IV is recovered from the mixture by extraction with a suitable inert organic solvent, e.g., toluene. The remaining aqueous solution is acidified to a pH of about 2.0 to about 3.0, preferably pH of about 2.4, using hydrochloric acid. The product is isolated by extraction using a suitable inert organic solvent, e.g., ethyl acetate, to provide compound XIX.

In step D5, compound XIX is reacted with compound XX, a dehydrative coupling agent, e.g., dicyclohexylcarbodiimide (DCC), and an activating agent, e.g., 1-hydroxybenzotriazole (HOBT), in a suitable inert organic solvent, e.g., dimethylformamide or acetonitrile, at about 25° C. to about 50° C., preferably about 40° C. The reaction is continued until the starting material is consumed, as determined by TLC, in about 4 hours. The product is isolated by extraction to obtain compound XXI.

In step D6, compound XXI is cyclized by treating with triphenylphosphine or preferably a trialkylphosphine, e.g., tri-n-butylphosphine, and a dialkylazodicarboxylate, e.g., diethylazodicarboxylate (DEAD), in a suitable anhydrous organic solvent, e.g., dry THF, under a dry, inert atmosphere, e.g. nitrogen, at about −50° C. to about −85° C., preferably about −70° C., for about 1 to about 3 hours, preferably about 2 hours. The reaction is then continued at about room temperature for about 12 to about 24 hours. The product is purified by preparative high performance liquid chromatography (HPLC) to obtain a compound of formula I, having trans relative stereochemistry. The use of tributylphosphine in this step gives reaction yields significantly higher than the yields obtained using triphenylphosphine.

Alternatively, step D6 comprises combining compound XXI and a suitable phase transfer catalyst, e.g. tetra-n-butylammonium hydrogen sulfate, in a suitable solvent, such as methylene chloride. The mixture is stirred while cooling to about 0° C. to 20° C., preferably about 10° C. to about 20° C., then treated with an aqueous base, such as an alkali metal hydroxide, preferably 50% aqueous sodium hydroxide. A di- or tri-chlorobenzoyl chloride, preferably 2;6-dichlorobenzoyl chloride or 2,4,6-trichlorobenzoyl chloride, is slowly added over a period of 20 to 60 minutes, preferably about 30 minutes. The mixture is stirred at about 0° C. to about 25° C., preferably about 15° C. to about 20° C., for a pedod of 2 to 4 hours, preferably about 3 hours, then poured into cold water. The organic layer is separated and washed with water to neutral pH. The di- or tri-chlorobenzoate product is isolated by crystallization from methylene chloride/heptane. The di- or tri-chlorobenzoate product is combined with a suitable phase transfer catalyst, e.g. benzyltriethylammonium chloride, in a suitable solvent, such as a mixture methylene chloride and methyl t-butyl ether. The mixture is stirred at about 0° C. to about 25° C., preferably about 15° C. to about 20° C., and treated with an aqueous base, e.g. an alkali metal hydroxide, preferably 50% aqueous sodium hydroxide. After stirring for a period of 2 to 6 hours, preferably about 4 hours, the mixture is poured into ice water. The organic layer is washed with water to neutral pH. The product is isolated by removing the solvent, then purified by chromatography and recrystallization from a suitable solvent to give a compound of formula I, having trans relative stereochemistry.

A third alternative for step D6 comprises treating compound XXI in a suitable solvent, such as $CH_2Cl_2$, with a dialkylchlorophosphate, preferably diethylchlorophosphate, and an aqueous base, such as an alkali metal hydroxide, preferably 50% aqueous sodium hydroxide, in the presence of phase transfer catalyst, such as tetra-n-butylammonium hydrogen sulfate or benzyltriethylammonium chloride.

Another alternative for step D6 comprises treating compound XXI with a di- or tri-chlorobenzoyl chloride, preferably 2,6-dichlorobenzoyl chloride or 2,4,6-trichlorobenzoyl chloride, and a suitable base, such as sodium hydride in a suitable solvent, such as $CH_2Cl_2$, dimethylformamide, or a combination thereof. The product is isolated and purified by chromatography followed by crystallization from a suitable solvent, e.g. ether/hexane.

Starting compounds XIII, XV, XVII, and XX are all either commercially available or well known in the art and can be prepared via known methods.

Method E:

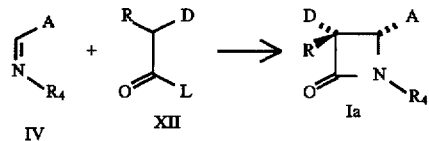

Compounds of formula Ia can also be prepared by treatment of an imine of formula IV with an activated carboxylic acid derivative of formula XII in the presence of a base such as triethylamine, tributylamine or diethylisopropylamine in an inert solvent such as $CH_2Cl_2$, heptane or toluene. Examples of activated carboxylic acid derivatives of formula XII include acid chlorides (L=Cl), mixed anhydrides formed with phenyl phosphorodichloridate (L=OP(O)(Cl) OPh), and N-methylpyridinium esters formed from the reaction of an acid with N-methyl-2-chloropyridinium iodide (L=2-oxy-N-methylpyridinium iodide).

Starting materials of formulae IV and V are known or can be prepared by methods well known in the art.

Method F:

Step F1

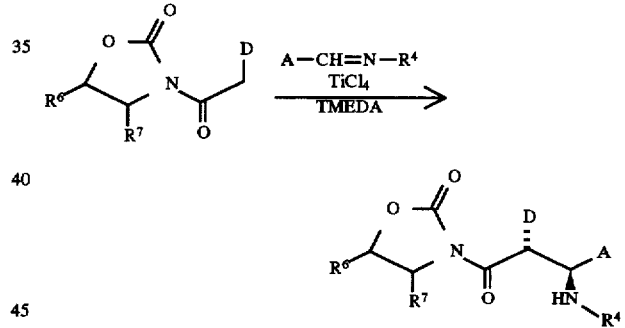

Step F2

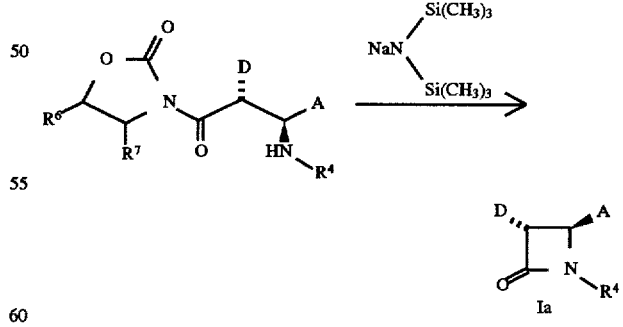

In step F1, compound XVI (from Method D, step 2) is dissolved in a suitable solvent, e.g. methylene chloride, then treated with titanium tetrachloride at about −60° C. to about 0° C., preferably about −25° C. to about −15° C., under a dry, inert atmosphere, preferably nitrogen, for a period of about 5 min. TMEDA is added and the mixture stirred at about −60° C. to about −10° C., preferably about −25° C. to about −20° C., for a period of about 1 hour. The imine (A—CH=N—R$^4$) is slowly over a pedod of 20 to 40 min., preferably about 30 min., and the mixture is stirred at about −60° C. to about 0° C., preferably about −25° C. to about −15° C., for 20 to 40 min., preferably about 30 min. The mixture is then warmed to about 0° C. and the reaction monitored by high pressure liquid chromatography (HPLC) until complete. The mixture is then poured into a solution of tartaric acid in water, preferably 10% tartaric acid. The product is isolated by extraction with a suitable solvent, e.g. ethyl acetate, then purified by crystallization.

In step F2, the product of step F1 is treated with a strong non-nucleophilic base, such as sodium or lithium bistrimethylsilylamide, in a suitable inert organic solvent, e.g. $CH_2Cl_2$, at about −20° C. to about 10° C., preferably about 0° C. The mixture is stirred while gradually warming to about 20° to about 25° C., then monitored by HPLC until the starting material is gone, typically after a period of 1 to 2 hours. The reaction mixture is poured into aqueous tartaric acid, preferably 10% tartaric acid, and the product isolated from the organic layer.

Imines of the formula A—CH=N—R$^4$ can be prepared from aldehydes of the formula A—CHO and amines of the formula R$^4$—NH$_2$ by procedures well known in the art. Aldehydes of formula A—CHO and amines of formula R$^4$—NH$_2$ are commercially available or can be prepared via known procedures.

Compounds of formula II can be prepared by methods similar to those described for compounds of formula I.

It will also be apparent to those skilled in the art, and by reference to the examples which follow, that compounds of formulae I and II can be converted into different compounds of formula I or II by well known methods. For example, a compound of formula I wherein A comprises a double or triple bond, or a compound of formula II wherein G comprises a double or triple bond can be converted to the corresponding saturated compound by treatment with hydrogen gas in the presence of a catalyst such as palladium or platinum on carbon.

Reactive groups not involved in the above processes can be protected during the reactions with conventional protecting groups which can be removed by standard procedures after the reaction. The following Table 3 shows some typical protecting groups:

TABLE 3

| Group to be Protected | Group to be Protected and Protecting Group |
|---|---|
| —COOH | —COOalkyl, —COObenzyl, —COOphenyl |
| \NH/ | \NCOalkyl/, \NCObenzyl/, \NCOphenyl/, \NCH$_2$OCH$_2$CH$_2$Si(CH$_3$)$_3$/, \NC(O)OC(CH$_3$)$_3$/, \N-benzyl/, \NSi(CH$_3$)$_3$/, \NSi—C(CH$_3$)$_3$/ with CH$_3$ groups |

TABLE 3-continued

| Group to be Protected | Group to be Protected and Protecting Group |
|---|---|
| —NH$_2$ | —N(succinimide-like ring with two C=O) |
| —OH | —OCH$_3$, —OSi(CH$_3$)$_3$, —OSi(CH$_3$)$_2$—C(CH$_3$)$_3$ |

We have found that the compounds of this invention lower serum lipid levels, in particular serum cholesterol levels. Compounds of this invention have been found to inhibit the intestinal absorbtion of cholesterol and to significantly reduce the formation of liver cholesteryl esters in animal models. Some compounds also inhibit ACAT in vitro. Thus, compounds of this invention are hypocholesterolemic agents by virtue of their ability to inhibit the esterification and/or intestinal absorption of cholesterol; they are therefore useful in the treatment and prevention of atherosclerosis in mammals, in particular in humans.

In addition to the compound aspect, the present invention therefore also relates to a method of lowering serum cholesterol levels, which method comprises administering to a mammal in need of such treatment a hypocholesterolemic effective amount of a compound of formula I or II of this invention. The compound is preferably administered in a pharmaceutically acceptable carrier suitable for oral administration.

The in vitro and in vivo activity of the compounds of formulae I or II can be determined by the following procedures.

ACAT Assay (in vitro)

This assay measures the activity of ACAT by measuring the ACAT-mediated transfer of tritiated oleic acid from acyl-CoA to cholesterol to give labelled cholesteryl oleate. Rat liver microsomes are used as the source of ACAT. Assays are performed in round bottom microtiterplates using a total incubation volume of 50 μL. Each incubation well receives 10 μL assay buffer (0.5M KHPO$_4$, 10 μM dithiothreitol, pH 7.4), 7.5 μL Of 40 mg/mL BSA (Bovine Serum Albumin) and 12.5 μg of microsomal protein. The test compound (in sufficient amount to bring the final concentration to from 0.1 to 25 μM), reference compound, or vehicle control is added and the final volume brought to 47 μL. The microtiterplate is then floated on the surface of a 37° C. water bath for fifteen minutes. Incubations are started by the addition of 3 μL $^3$H-acyl CoA (1 μCi/well, final concentration of 10 μM acyl CoA). The plate is then returned to the water bath for 15 minutes. The incubations are then terminated by application of 15 μL from each incubation to individual lanes on a thin layer plate (Silica Gel GF 20×20 cm). Standards are applied to several lanes so that the cholesteryl ester band can be identified. After drying, the plates am eluted with 90:10:1 petroleum ether:diethyl ether: acetic acid. The standards am visualized via iodine vapor, and the regions corresponding to cholesteryl ester are scraped into 7 mL scintillation vials. 4 mL of scintillant are added to each vial, and the radioactivity quantified. Background count is determined by the boiled controls. Full activity is determined by activity in the presence of vehicle. The percent inhibition is calculated by subtracting the background from both control and test samples, and the test value is calculated as a percentage of the control. For $IC_{50}$ determinations, the inhibition is plotted against drug does on a log scale and the concentration at which 50% inhibition is obtained is determined.

In Vivo Assay of Hypolipidemic Agents Using the Hyperlipidemic Hamster

Hamsters are separated into groups of six and given a controlled cholesterol diet (Purina Chow #5001 containing 0.5% cholesterol) for seven days. Diet consumption is monitored to determine dietary cholesterol exposure in the face of test compounds. The animals are dosed with the test compound once daily beginning with the initiation of diet. Dosing is by oral gavage of 0.2mL of corn oil alone (control group) or solution (or suspension) of test compound in corn oil. All animals roodbund or in poor physical condition are euthanized. After seven days, the animals are anesthetized by IM injection of ketamine and sacrificed by decapitation. Blood is collected into vacutainer tubes containing EDTA for plasma lipid analysis and the liver excised for tissue lipid analysis. Data is reported as percent reduction of lipid versus control.

The present invention also relates to a pharmaceutical composition comprising a Compound of formula I or II of this invention and a pharmaceutically acceptable carrier. The compounds of formula I or II can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily hypocholesteremic dose of a compound of formula I or II is about 7 to about 30 mg/kg of body weight per day. For an average body weight of 70 kg, the dosage level is therefore from about 500 to about 2000 mg of drug per day, given in a single dose or 2–4 divided doses. The exact dose, however, is determined by the attending clinician and is dependent on the potency of the compound administered, the age, weight, condition and response of the patient.

Following are examples of preparing compounds of formulae I and II. The stereochemistry listed is relative stereochemistry unless otherwise noted. The terms cis/trans refer to the relative orientations at the beta-lactam 3- and 4-positions when each is mono-substituted (i.e., R=H).

EXAMPLE 1

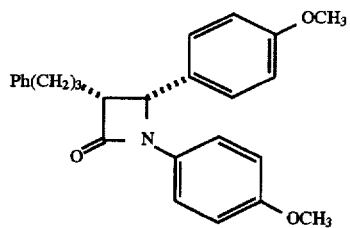

Freshly prepare lithium diisopropyl amide (LDA) by dissolving 23.96 mL (17.39 g, 172mmol) diisopropylamine in 230 mL dry THF at −78° C. under nitrogen. Add 103.9 mL (166 mmol@1.6M in hexanes) of n-butyl lithium and stir at −78° C. for 1 h. To this cold solution add 32.58 g (158 mmol) of 5-phenyl valeric acid ethyl ester in 195 mL dry THF over ~1 h, keeping the reaction temperature below −65° C. Stir for 1 h at −78° C., then add 38.13 g (158 mmol) of 4-methoxybenzylidine anisidine in 350 mL dry $CH_2Cl_2$. Allow the reaction to slowly come to room temperature and the precipitate that forms will begin to go into solution. Stir the reaction mixture for 16 h at room temperature. Partition the mixture between 1.2 liter of 1N aqueous hydrochloric acid (HCl) and 1 liter of ether. Wash the ether layer with 300 mL 1N HCl. Combine the acid layers and extract with 1 liter of ether. Combine the ether extracts, dry over $MgSO_4$ and concentrate in vacuo. Crystallize the residue (35.08 g, 55%) from ~200 mL ethyl acetate-hexane (1:1) to give 32.05 g of the title racemic compound as an off-white crystal, mp=90°–93° C.

Using a similar procedure, the following compounds shown in Tables 4 and 4A can also be prepared:

| Ex. | D | R | A | Relative Stereochemistry | R₄ | Data |
|---|---|---|---|---|---|---|
| 1A | C₆H₅—CH₂C(O)— | C₆H₅— | C₆H₅— | 3R,4S | p-MeO—C₆H₄— | mp = 120.5-122.0° C. |
| 1B | C₆H₅—(CH₂)₃— | H | C₆H₅— | 3R,4R | p-MeO—C₆H₄— | mp = 120.5-121.5° C. |
| 1C | C₆H₅—(CH₂)₃— | H | C₆H₅— | 3S,4R | p-MeO—C₆H₄— | mp = 92.0-92.5° C. |
| 1D | C₆H₅—(CH₂)₃— | H | C₆H₅— | 3S,4S | p-MeO—C₆H₄— | mp = 151-152° C. |
| 1E | C₆H₅—(CH₂)₃— | H | C₆H₅— | 3S,4R | p-MeO—C₆H₄— | mp = 156-158° C. |
| 1F | C₆H₅—(CH₂)₃— | H | C₆H₅— | 4:1 cis to trans | 2,4,6-tri-MeO—C₆H₄— | CI MS: (M + 1) 432 |
| 1G | C₆H₅—(CH₂)₃— | H | p-NO₂—C₆H₄— | 3S,4R | p-MeO—C₆H₄— | mp = 116-117° C. |
| 1H | C₆H₅—(CH₂)₃— | H | p-NO₂—C₆H₄— | 3R,4R | p-MeO—C₆H₄— | mp = 120.5-122.0° C. |
| 1I | C₆H₅—(CH₂)₃— | CH₃CH₂— | —C₆H₅CH=CH— | 3S,4S | 2,4,6-tri-MeO—C₆H₄— | FAB MS: (M + 1) 486.2 |
| 1J | C₆H₅—(CH₂)₃— | CH₃CH₂— | C₆H₅—CH=CH— | 3R,4S | 2,4,6-tri-MeO—C₆H₄— | FAB MS: (M + 1) 486.2 |
| 1K | C₆H₅—(CH₂)₃— | H | C₆H₅—CH=CH— | 3S,4S | p-MeO—C₆H₄— | mp = 119.5-120.5° C. |
| 1L | C₆H₅—(CH₂)₃— | H | p-OH—C₆H₄— | 3S,4S | p-MeO—C₆H₄— | mp = 152.5-155.0° C. |
| 1M | C₆H₅—(CH₂)₃— | H | p-MeO—C₆H₄— | 3S,4S | p-MeO—C₆H₄— | mp = 86-88° C. |
| 1P | C₆H₅—(CH₂)₃— | H | 3-MeO—C₆H₄— | 3S,4S | p-MeO—C₆H₄— | mp = 90.5-91.0° C. |
| 1AM | C₆H₅—(CH₂)₃— | H | p-MeO—C₆H₄— | trans | 3-pyridyl | 1H NMR (CDCl3) δ 8.41(s, 1H), 8.28(s, 1H), 7.79(d, 1H), 7.20(m, 8H), 6.90(d, 2H), 4.63(s, 1H), 3.80(s, 3H), 3.20(t, 1H), 1.85(m, 4H) |
| 1AN | C₆H₅—(CH₂)₃— | H | p-MeO—C₆H₄— | trans | p-CF₃O—C₆H₄— | elemental analysis: calc'd C = 68.56, H = 5.31, N = 3.08; found C = 68.32, H = 5.12, N = 2.97 |
| 1AO | C₆H₅—(CH₂)₃— | H | 4-MeO—C₆H₄— | cis | p-Cl—C₆H₄— | elemental analysis: calc'd C = 73.97, H = 5.96, N = 3.45, Cl = 8.73; found C = 73.63, H = 5.92, N = 3.52, Cl = 9.12 |
| 1AP | C₆H₅—(CH₂)₃— | H | 4-MeO—C₆H₄— | cis | p-CH₃—C₆H₄— | elemental analysis: calc'd C = 81.01, H = 7.06, N = 3.63; found C = 80.97, H = 7.06, N = 3.74 |
| 1AQ | C₆H₅—(CH₂)₃— | H | 4-CH₃O—C₆H₄— | cis | p-C₆H₅O—C₆H₄— | elemental analysis: calc'd C = 80.32, H = 6.31, N = 3.02; found C = 80.26, H = 6.27, N = 3.18 |
| 1AR | C₆H₅—(CH₂)₃— | H | ![pyridine with CH3] | trans | p-CH₃O—C₆H₄— | mp = 101.5-102.5° C. |
| 1AS | C₆H₅—(CH₂)₃— | H | (CH₃)₃CSi(CH₃)₂—OCH₂—C₆H₄— | trans | p-CH₃O—C₆H₄— | EIMS (M + 1) = 516 |
| 1AT | C₆H₅—(CH₂)₃— | H | (CH₃)₃CSi(CH₃)₂—OCH₂—C₆H₄— | cis | p-CH₃O—C₆H₄— | mp = 84-85° C. |
| 1AU | C₆H₅—(CH₂)₃— | H | 4-CH₃S—C₆H₄— | cis | p-CH₃O—C₆H₄— | mp = 103-104° C. |

-continued

| | | | | | | |
|---|---|---|---|---|---|---|
| 1AV | C$_6$H$_5$—(CH$_2$)$_3$— | H | 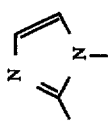 | trans | p-CH$_3$O—C$_6$H$_4$— | FABMS (M + 1) = 492 |
| 1AW | C$_6$H$_5$—(CH$_2$)$_3$— | H | 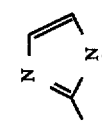 | cis | p-CH$_3$O—C$_6$H$_4$— | mp = 108.5–110° C. |
| 1AX | C$_6$H$_5$—(CH$_2$)$_3$— | H | 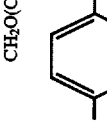 | cis | p-CH$_3$O—C$_6$H$_4$— | EIMS (M) = 443 |
| 1AY | C$_6$H$_5$—(CH$_2$)$_3$— | H | 4-((CH$_3$)$_2$CH—O)—C$_6$H$_4$— | cis | p-CH$_3$O—C$_6$H$_4$— | mp = 96–97° C. |
| 1AZ | C$_6$H$_5$—(CH$_2$)$_3$— | H | 4-(CH$_3$(CH$_2$)—O)—C$_6$H$_4$— | cis | p-CH$_3$O—C$_6$H$_4$— | mp = 96–97° C. |
| 1BA | C$_6$H$_5$—(CH$_2$)$_3$— | H |  | cis | p-CH$_3$O—C$_6$H$_4$— | mp = 91.5–92.5° C. |
| 1BB | C$_6$H$_5$—(CH$_2$)$_3$— | H | 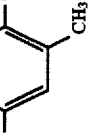 | cis | p-CH$_3$O—C$_6$H$_4$— | mp = 86.0–87.0° C. |
| 1BC | C$_6$H$_5$—(CH$_2$)$_3$— | H | 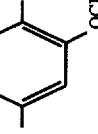 | cis | p-CH$_3$O—C$_6$H$_4$— | mp = 130.0–131.0° C. |
| 1BD | C$_6$H$_5$—(CH$_2$)$_3$— | H | 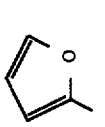 | trans | p-CH$_3$O—C$_6$H$_4$— | mp = 111.0–112.5° C. |
| 1BE | C$_6$H$_5$—(CH$_2$)$_3$— | H | 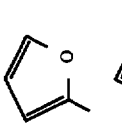 | cis | p-CH$_3$O—C$_6$H$_4$— | mp = 74.5–75° C. |

-continued

| ID | | | | | | |
|---|---|---|---|---|---|---|
| 1BF | C$_6$H$_5$—(CH$_2$)$_3$— | H | (furan ring) | trans | p-CH$_3$O—C$_6$H$_4$— | mp = 79.5–80.5° C. |
| 1BG | C$_6$H$_5$—(CH$_2$)$_3$— | H | 4-CF$_3$—C$_6$H$_4$— | trans | p-CH$_3$O—C$_6$H$_4$— | mp = 94.5–96.0° C. |
| 1BH | C$_6$H$_5$—(CH$_2$)$_3$— | H | 4-CF$_3$—C$_6$H$_4$— | cis | p-CH$_3$O—C$_6$H$_4$— | mp = 114.0–115.5° C. |
| 1BI | C$_6$H$_5$—(CH$_2$)$_3$— | H | (thiophene) | cis | p-CH$_3$O—C$_6$H$_4$— | mp = 117–120° C. |
| 1BJ | C$_6$H$_5$—(CH$_2$)$_3$— | H | (thiophene) | cis | p-CH$_3$O—C$_6$H$_4$— | mp = 88.5–90.5° C. |
| 1BK | C$_6$H$_5$—(CH$_2$)$_3$— | H | 3-CF$_3$—O—C$_6$H$_4$— | cis | p-CH$_3$O—C$_6$H$_4$— | mp = 66.0–68.0° C.; CI MS (M + 1) = 456.2 |
| 1BL | C$_6$H$_5$—(CH$_2$)$_3$— | H | 3-CF$_3$—O—C$_6$H$_4$— | trans | p-CH$_3$O—C$_6$H$_4$— | mp = 124–125° C. |
| 1BM | C$_6$H$_5$—(CH$_2$)$_3$— | H | 4-CH$_3$—C$_6$H$_4$— | cis | p-CH$_3$O—C$_6$H$_4$— | mp = 131–132° C. |
| 1BN | C$_6$H$_5$—(CH$_2$)$_3$— | H | 4-(C$_6$H$_5$—CH$_2$—O)—C$_6$H$_4$— | cis | p-CH$_3$O—C$_6$H$_4$— | mp = 84–85° C. |
| 1BO | C$_6$H$_5$—(CH$_2$)$_3$— | H | CH$_3$CH$_2$—O—C$_6$H$_4$— | cis | p-CH$_3$O—C$_6$H$_4$— | |
| 1BP | C$_6$H$_5$—(CH$_2$)$_3$— | H | (thiophene) | trans | p-CH$_3$O—C$_6$H$_4$— | mp = 68–70° C. |
| 1BQ | C$_6$H$_5$—(CH$_2$)$_3$— | H | (thiophene) | trans | p-CH$_3$O—C$_6$H$_4$— | mp = 50–52° C. |
| 1BR | C$_6$H$_5$—(CH$_2$)$_3$— | H | CH$_3$(CH$_2$)$_3$—O—C$_6$H$_4$— | cis | p-CH$_3$O—C$_6$H$_4$— | mp = 71.0–72.5° C. |
| 1BS | C$_6$H$_5$—(CH$_2$)$_3$— | H | 4-(C$_6$H$_5$—O)—C$_6$H$_4$— | cis | p-CH$_3$O—C$_6$H$_4$— | mp = 108–109° C. |
| 1BT | C$_6$H$_5$—(CH$_2$)$_3$— | H | 4-(C$_6$H$_5$)—C$_6$H$_4$— | cis | p-CH$_3$O—C$_6$H$_4$— | mp = 127.5–128.5° C. |
| 1BU | C$_6$H$_5$—(CH$_2$)$_3$— | H | 4-(CH$_2$=CH—CH$_2$—O)—C$_6$H$_4$— | cis | p-CH$_3$O—C$_6$H$_4$— | mp = 77.0–77.5° C. |
| 1BV | C$_6$H$_5$—(CH$_2$)$_3$— | H | 3,4,5-trimethoxyphenyl (OCH$_3$, OCH$_3$, OCH$_3$) | cis | | mp = 116–117° C. |

-continued

| ID | Col1 | Col2 | Col3 | Config | Col5 | Notes |
|---|---|---|---|---|---|---|
| 1BW | $C_6H_5-(CH_2)_3-$ | H | N-methylindole group | cis | $p-CH_3O-C_6H_4-$ | mp = 129.5–130.5° C. |
| 1BX | $C_6H_5-(CH_2)_3-$ | H | quinoline group | cis | $p-CH_3O-C_6H_4-$ | mp = 170.0–170.5° C. |
| 1BY | $C_6H_5-(CH_2)_3-$ | H | $4-(CH_3CH_2-O)-C_6H_4-$ | cis | $C_6H_5-$ | mp = 89.5–90.0° C. |
| 1BZ | $C_6H_5-(CH_2)_3-$ | H | 2-methylbenzofuran | cis | $p-CH_3O-C_6H_4-$ | mp = 100–104° C. |
| 1CA | $C_6H_5-(CH_2)_3-$ | H | 2-methylbenzofuran | trans | $4-CH_3O-C_6H_4-$ | mp = 91–92° C. |
| 1CB | $C_6H_5-(CH_2)_3-$ | H | $4-CH_3O-C_6H_4-$ | cis | $(CH_3)_3CSi(CH_3)_2-O-C_6H_4-$ | mp = 93–94° C. |
| 1CC | $C_6H_5-(CH_2)_3-$ | H | $4-CH_3O-C_6H_4-$ | cis | $4-CH_3O-C_6H_4-$ | mp = 128–129° C. |
| 1CD | $C_6H_5-O-(CH_2)_2-$ | H | $4-CH_3O-C_6H_4-$ | cis | $4-CH_3O-C_6H_4-$ | mp = 120–121° C. |
| 1CE | $C_6H_5-(CH_2)_6-$ | H | $4-CH_3O-C_6H_4-$ | cis | $4-CH_3O-C_6H_4-$ | mp = 80–81° C. |
| 1CF | cyclohexyl-$(CH_2)_3-$ | H | $4-CH_3O-C_6H_4-$ | cis | $4-CH_3O-C_6H_4-$ | mp = 101–102° C. |
| 1CG | $4-F-C_6H_4-O-(CH_2)_2-$ | H | $4-CH_3O-C_6H_4-$ | cis | $4-CH_3O-C_6H_4-$ | elemental analysis: calc'd C = 71.25, H = 5.74, N = 3.32; found C = 71.34, H = 5.73, N = 3.43 |
| 1CH | $4-F-C_6H_4-O-(CH_2)_2-$ | H | $4-CH_3O-C_6H_4-$ | cis | $C_6H_5-$ | elemental analysis: calc'd C = 73.64, H = 5.67, N = 3.; found C = 73.39, H = 5.51, N = 3.54 |
| 1CI | $C_6H_5-(CH_2)_4-$ | H | $4-CH_3O-C_6H_4-$ | cis | $4-CH_3O-C_6H_4-$ | elemental analysis: calc'd C = 78.04, H = 7.03, N = 3.37; found C = 77.69, H = 6.98, N = 3.60 |
| 1CM | $C_6H_5-(CH_2)_3-$ | H | $4-CH_3S-C_6H_4-$ | trans | $4-CH_3O-C_6H_4-$ | mp = 104–105.5° C. |

-continued

| Ex. | | | | | |
|---|---|---|---|---|---|
| 1CN | $C_6H_5-(CH_2)_3-$ | | 4-$CH_3O-C_6H_4-$ | cis | mp = 144.0–144.5° C. |
| 1CO | $C_6H_5-(CH_2)_3-$ | H | 4-$((CH_3)_2N-(CH_2)_3-O)-C_6H_4-$ | cis | mp = 92–94° C. |
| 1CP | $C_6H_5-(CH_2)_3-$ | H | 4-$CH_3O-C_6H_4-$ | cis | elemental analysis:<br>calc'd C = 80.83, H = 6.78, N = 3.77;<br>found C = 80.69, H = 6.78, N = 3.90 |

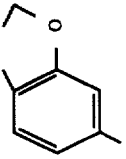

| Ex. | $R_{21}-E-$ | $R_{22}-F-$ | $R_{23}-G-$ | $R_{20}$ | Rel. Stereochemistry | Data |
|---|---|---|---|---|---|---|
| 1S | $C_{10}H_{21}-$ | H | $C_6H_5-$ | p-MeO—$C_6H_4-$ | 3R,4R | mp = 176.0–177.0° C. |
| 1T | $C_{10}H_{21}-$ | H | $C_6H_5-$ | p-MeO—$C_6H_4-$ | 3S,4R | mp = 83.5–84.0° C. |
| 1U | $C_{10}H_{21}-$ | H | $C_6H_5-$ | 2,4,6-tri-MeO—$C_6H_4-$ | 3R,4R 3.6:1 cis/trans | |
| 1V | H | $C_6H_5-$ | $C_6H_5-$ | p-MeO—$C_6H_4-$ | 3R,4R | mp = 158.5–159.0° C. |
| 1W | H | i-Pr | $C_6H_5-$ | p-MeO—$C_6H_4-$ | 3R,4R | mp = 162–164° C. |
| 1X | $C_6H_5-CH_2-$ | $C_6H_5-$ | $C_6H_5-$ | p-MeO—$C_6H_4-$ | 3S,4S | mp = 185.0–186.0° C. |
| 1Y | $C_6H_5-CH_2-$ | $C_6H_5-$ | $C_6H_5-$ | p-MeO—$C_6H_4-$ | 3S,4S | mp = 123.0–124.5° C. |
| 1Z | $CH_3CH_2-$ | $C_6H_5-$ | $C_6H_5-$ | p-MeO—$C_6H_4-$ | 3S,4S | mp = 101.0–102.5° C. |
| 1AA | $CH_3CH_2-$ | $C_6H_5-$ | $C_6H_5-$ | p-MeO—$C_6H_4-$ | 3R,4R | mp = 73.5–75.0° C. |
| 1AB | H | $C_6H_5-$ | $C_6H_5-$ | p-MeO—$C_6H_4-$ | 3R,4R | mp = 134.0–135.5° C. |
| 1AC | cyc-$C_3H_{11}$ | $CH_3CH_2-$ | $C_6H_5-$ | p-MeO—$C_6H_4-$ | 8:5 mix cis/trans phenyl | mp = 57.5–62.5° C. |
| 1AD | H | $C_6H_5-$ | $C_6H_5-$ | p-MeO—$C_6H_4-$ | 3R,4S | mp = 107–109° C. |
| 1AE | H | $CH_3CH_2-$ | $C_6H_5-CH=CH-$ | 2,4,6-tri-MeO—$C_6H_4-$ | 3R,4S | CI MS: (M + 1) 342 |
| 1AF | H | $CH_3CH_2-$ | $C_6H_5-CH=CH-$ | p-MeO—$C_6H_4-$ | 3R,4S | FAB MS: (M + 1) 307.9 |
| 1AG | H | $CH_3CH_2-$ | $C_6H_5-$ | p-MeO—$C_6H_4-$ | 3S,4S | mp = 84–86° C. |
| 1AH | H | $CH_3-$ | $C_6H_5-$ | p-MeO—$C_6H_4-$ | 3S,4S | mp = 122–123° C. |
| 1AI | H | $CH_3-$ | $C_6H_5-$ | p-MeO—$C_6H_4-$ | 3S,4S | mp = 93–94° C. |
| 1AJ | H | $CH_3CH_2-$ | p-$NO_2-C_6H_5$ | p-MeO—$C_6H_4-$ | 3S,4R | mp = 115–116° C. |
| 1AK | H | $CH_3CH_2-$ | 4-$NO_2-C_6H_4-$ | p-MeO—$C_6H_4-$ | 3R,4R | mp = 101–102° C. |
| 1AL | H | $CH_3CH_2-$ | 4-MeO—$C_6H_4-$ | p-MeO—$C_6H_4-$ | 3S,4S | mp = 96–103° C. |
| 1CJ | $(CH_3)_2-N-$ | H | 4-MeO—$C_6H_4-$ | $C_6H_5-$ | cis | mp = 115–117° C. |
| 1CK | $C_6H_5-$ | $CH_3CH_2-$ | 4-MeO—$C_6H_4-$ | 4-MeO—$C_6H_4-$ | trans | mp = 56–58° C. |
| 1CL | $C_{10}H_{21}-$ | H | 4-MeO—$C_6H_4-$ | 4-MeO—$C_6H_4-$ | cis | elem. anal:<br>calc'd C = 76.56, H = 8.80, N = 3.31;<br>found C = 76.60, H = 8.77, N = 3.48 |

EXAMPLE 2

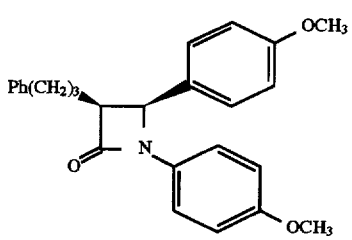

STEP 1: Add 39.1 mL (117.2 mmol) of ethyl magnesium bromide to a 0° C. solution of 31.00 g (97.6 mmol) of (−)-10-(diisopropylsulfonamido)-isoborneol (See Oppolzer, et al, *Tet. Lett.* 25 (1984), p. 5885) in 370 mL dry THF. Stir the mixture for 0.5 h at 0° C., then at room temperature for 0.5 h. Add 37.74 mL (39.67 g, 117.2 mmol) of 5-phenylvaleric acid anhydride to this mixture at 0° C. and stir overnight at room temperature. Pour the mixture into 1 liter of half-saturated NaHCO$_3$ and extract with two-800mL portions of hexane. Dry the combined hexane layers with Na$_2$SO$_4$ and concentrate in vacuo. Chromatograph the residue (57.35 g) in three portions over ~800 g SiO$_2$ eluting with 2% ethyl acetate-CH$_2$Cl$_2$ to obtain the desired ester (42.07 g, 90.2%). FAB MS: (M+1) 479.

STEP 2: Using a procedure similar to Example 1, treat the ester of Step 1, washing the ether layer with 200 mL 1N aqueous HCl, drying with MgSO$_4$ and concentrating in vacuo. Chromatograph the residue over 1 kg SiO$_2$, eluting with 20% ethyl acetate-hexane to give 24.19 g (79%) of the recovered alcohol and 25.66 (66%) of the title enantiomerically enriched β-lactam. This lactam can be further enriched by chromatography over a Chiralcel™ OD column (Daicel Chemical Industries, Ltd., Fort Lee, N.J.), eluting with 10% isopropanol-hexanes. Crystallize the resulting enantiomerically pure (3S,4S) compound from ether-hexane to obtain a white solid, mp=84°–85° C., $[\alpha]_D^{25}$=−98.0° (MeOH).

Using a similar procedure, the following enantiomerically pure (3R,4R) compound (EXAMPLE 2A) can also be prepared:

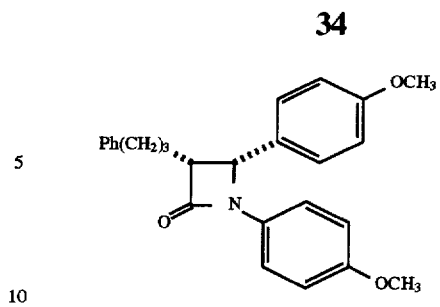

(m.p.=84°–85° C.; FAB MS: (M+1) 402.2; $[\alpha]_D^{25}$=+98.0° (MeOH).

EXAMPLE 3

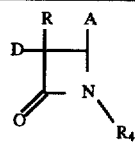

Freshly prepare a solution of lithium isopropylcyclohexyl amide (LICA) by dissolving 0.68 mL (0.58 g, 4.11 mmol) isopropylcyclohexyl amine in 20 mL THF at −78° C. under nitrogen. Add 2.58 mL (4.03 mmol) n-butyl lithium (1.6M, from Aldrich, Milwaukee, Wis.) and stir at −78° C. for 1 h. Add 1.04 g (2.61 mmol) of the compound of Example 1K in 5 mL dry THF to the solution. After 2 h at −78° C., add 2.8 mL (2.89 g, 16 mmol) of hexamethylphosphoric triamide followed by 0.33 mL (641 mg, 4.11 mmol) of ethyl iodide at −78° C. Stir the mixture overnight at room temperature. Quench the reaction with 40 mL 1N aqueous HCl and extract with two-50 mL portions of CH$_2$Cl$_2$. Combine the CH$_2$Cl$_2$ layers and wash sequentially with 50 mL 1N aqueous HCl and 50 mL Na$_2$SO$_3$. Dry over MgSO$_4$ and concentrate in vacuo. Chromatograph the residue over 40 g SiO$_2$, eluting with 20% ethyl acetate-hexane to give 0.95 g (83%) of the title compound as a colorless oil, FAB MS: (M+1) 426.4.

Using a similar procedure, the following compounds shown in Tables 5 and 5A can also be prepared:

| Ex. | D | R | A | Relative Stereochemistry | R$_4$ | Data |
|---|---|---|---|---|---|---|
| 3A | C$_6$H$_5$—(CH$_2$)$_3$— | CH$_3$CH$_2$— | C$_6$H$_5$— | 3S,4S | p-MeO—C$_6$H$_4$— | mp = 103.0–103.5° C. |
| 3B | C$_6$H$_5$—(CH$_2$)$_3$— | C$_6$H$_5$— | C$_6$H$_5$— | 3R,4S | p-MeO—C$_6$H$_4$— | FAB MS: (M + 1) 448 |
| 3C | C$_6$H$_5$—(CH$_2$)$_3$— | C$_{10}$H$_{21}$— | C$_6$H$_5$— | 3S,4R | p-MeO—C$_6$H$_4$— | CI MS: (M + 1) 512 |
| 3D | C$_6$H$_5$—(CH$_2$)$_3$— | CH$_3$CH$_2$— | C$_6$H$_5$— | 3S,4S | 2,4,6-tri-MeO—C$_6$H$_4$— | mp = 145.5–147.0° C. |
| 3E | C$_6$H$_5$—(CH$_2$)$_3$— | CH$_3$CH$_2$— | C$_6$H$_5$— | 3R,4S | p-MeO—C$_6$H$_4$— | mp = 82.5–83.5° C. |
| 3F | C$_6$H$_5$—(CH$_2$)$_3$— | CH$_3$CH$_2$— | C$_6$H$_5$— | 3R,4S | 2,4,6-tri-MeO—C$_6$H$_4$— | mp = 132–134° C. |
| 3G | C$_6$H$_5$—(CH$_2$)$_3$— | CH$_3$CH$_2$— | C$_6$H$_5$—CH=CH— | 3S,4S | p-MeO—C$_6$H$_4$— | mp = 98–99° C. |
| 3H | C$_6$H$_5$—(CH$_2$)$_2$— | CH$_3$CH$_2$— | C$_6$H$_5$— | 3R,4S | p-MeO—C$_6$H$_4$— | mp = 100.0–100.5° C. |
| 3I | C$_6$H$_5$—(CH$_2$)$_2$— | CH$_3$— | C$_6$H$_5$— | 3R,4S | p-MeO—C$_6$H$_4$— | mp = 130–131° C. |
| 3J | C$_6$H$_5$—(CH$_2$)$_3$— | CH$_3$— | C$_6$H$_5$— | 3S,4S | p-MeO—C$_6$H$_4$— | mp = 88–89° C. |
| 3K | C$_6$H$_5$—(CH$_2$)$_4$— | CH$_3$— | C$_6$H$_5$— | 3S,4S | p-MeO—C$_6$H$_4$— | mp = 109–110° C. |
| 3L | C$_6$H$_5$—(CH$_2$)$_4$— | CH$_3$CH$_2$— | C$_6$H$_5$— | 3S,4S | p-MeO—C$_6$H$_4$— | mp = 95–96° C. |
| 3M | C$_6$H$_5$—(CH$_2$)$_3$— | CH$_3$CH$_2$— | p-MeO—C$_6$H$_4$— | 3R,4S | p-MeO—C$_6$H$_4$— | FAB MS: (M + 1) 430.4 |

-continued

| Ex. | | | | Rel. Stereochemistry | $R_{20}$ | Data |
|---|---|---|---|---|---|---|
| 3N | $C_6H_5-(CH_2)_3-$ | $C_6H_4-(CH_2)_3-$ | $C_6H_5-CH=CH-$ | racemic | $p-MeO-C_6H_4-$ | FAB MS: (M + 1) 516.4 |
| 3O | $C_6H_5-(CH_2)_3-$ | $CH_3CH_2-$ | $p-MeO-C_6H_4-$ | 3S,4S | $p-MeO-C_6H_4-$ | FAB MS: (M + 1) 430.4 |

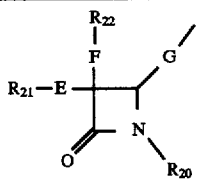

| Ex. | $R_{21}-E-$ | $R_{22}-F-$ | $R_{23}-G-$ | Rel. Stereochemistry | $R_{20}$ | Data |
|---|---|---|---|---|---|---|
| 3Q | $C_{10}H_{21}-$ | $CH_3CH_2-$ | $C_6H_5-$ | 3S,4S | $p-MeO-C_6H_4-$ | mp = 47.5–48.5° C. |
| 3R | $C_{10}H_{21}-$ | $C_6H_5-$ | $C_6H_5-$ | 3R,4S | $p-MeO-C_6H_4-$ | mp = 103.0–103.5° C. |
| 3T | $C_{10}H_{21}-$ | $CH_3CH_2-$ | $C_6H_5-$ | 3R,4R | $p-MeO-C_6H_4-$ | mp = 48.0–49.5° C. |
| 3U | $C_{10}H_{21}-$ | $C_6H_5-(CH_2)_3-$ | $C_6H_5-$ | 3R,4R | $p-MeO-C_6H_4-$ | CI MS: (M + 1) 512.6 |
| 3V | $C_{10}H_{21}-$ | $CH_3CH_2-$ | $C_6H_5-$ | 3S,4R | $2,4,6-tri-MeO-C_6H_4-$ | CI MS: (M + 1) 482 |
| 3W | $C_{10}H_{21}-$ | $CH_3CH_2-$ | $C_6H_5-$ | 3R,4R | $2,4,6-tri-MeO-C_6H_4-$ | mp = 96–98° C. |
| 3X | $C_{10}H_{21}-$ | $CH_3CH_2-$ | $C_6H_5-CH=CH-$ | 3S,4S | $p-MeO-C_6H_4-$ | EI MS: (M⁺) 425 |
| 3Y | $C_{10}H_{21}-$ | $CH_3-$ | $C_6H_5-$ | 3S,4S | $p-MeO-C_6H_4-$ | mp = 96–97° C. |

EXAMPLE 4

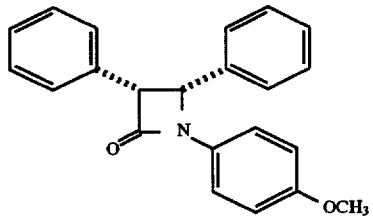

Add 100 mg (0.30 mmol) of the trans β-lactam of Example 1 V in 2 mL dry THF to a solution of 1.22 mL (0.32 mmol) LDA (1.5M, from Aldrich, Milwaukee, Wis.) in 0.5 mL dry THF at −78° C. under nitrogen. Stir for 5 min at −78° C., then quench at low temperature with ~0.3 mL acetic acid. Partition the mixture between 30 mL ethyl acetate and 20 mL water. Wash the organic layer with 20 mL 10% aqueous $NaHCO_3$ solution, dry over $MgSO_4$ and concentrate in vacuo to give 98 mg of an oily white solid. Chmmatograph the residue over $SiO_2$, eluting with 20% ethyl acetate-hexane to obtain 26 mg of the title cis β-lactam as a white solid, mp=1 41.3°–142.3° C.

EXAMPLE 5

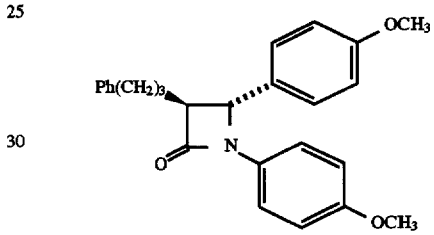

Dissolve 32.05 g (79.8 mmol) of the racemic cis β-lactam of Example 1 in 500 mL of THF. Add 1.79 g (16.0 mmol) of potassium t-butoxide and stir at 0° C. for 1.5 h. Partition the reaction mixture between 600 mL 1N aqueous HCl and 1.2 liters of ether. Extract the aqueous layer with 400 mL of ether. Combine the ether layers, dry over $MgSO_4$ and concentrate in vacuo to give 32.0 g of a mixture of cis and trans β-lactams (2.7:1). Isolate the pure trans β-lactam via silica gel HPLC chromatography, eluting with 10% ethyl acetate-hexane. Crystallize .from ethyl acetate-hexane to give white crystals, mp=96.0°–97.5°.

Using a procedure similar to that of Example 5, the following compounds shown in Tables 6 and 6A can be prepared:

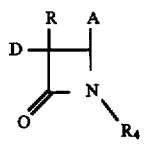

| Ex. | D | R | A | Relative Stereochemistry | $R_4$ | Data |
|---|---|---|---|---|---|---|
| 5B | $C_6H_5-(CH_2)_3-$ | H | $4-CH_3O-C_6H_4-$ | 3S,4R single enantiomer | $4-CH_3O-C_6H_4-$ | FAB MS (M + 1) = 402.2 |
| 5C | $C_6H_5-(CH_2)_3-$ | H | $3-CH_3O-C_6H_4-$ | 3R,4S | $4-CH_3O-C_6H_4-$ | mp = 109.5–110.0° C. |
| 5D | $C_6H_5-(CH_2)_3-$ | H | $4-CH_3O-C_6H_4-$ | trans | $4-F-C_6H_4-$ | CIMS (M + 1) = 390 |
| 5E | $C_6H_5-(CH_2)_3-$ | H | $4-CH_3O-C_6H_4-$ | trans | $3-CH_3O-C_6H_4-$ | elemental analysis: calc'd C = 77.78, H = 6.78, N = 3.49; found C = 77.75, H = 6.70, |

-continued

| | | | | | | |
|---|---|---|---|---|---|---|
| 5G | $C_6H_5-(CH_2)_3-$ | H | $4-CH_3O-C_6H_4-$ | trans | $4-Cl-C_6H_4-$ | N = 3.60<br>CIMS (M + 1) = 406 |
| 5H | $C_6H_5-(CH_2)_3-$ | H | $4-CH_3O-C_6H_4-$ | trans | $4-(CH_3CH_2-O)-C_6H_4-$ | elemental analysis:<br>calc'd C = 78.04, H = 7.04,<br>N = 3.37;<br>found C = 78.01, H = 7.03,<br>N = 3.47 |
| 5I | $C_6H_5-(CH_2)_3-$ | H | $4-CH_3O-C_6H_4-$ | trans | $4-CH_3S-C_6H_4-$ | elemental analysis:<br>calc'd C = 74.79, H = 6.52,<br>N = 3.35;<br>found C = 74.74, H = 6.44,<br>N = 3.48 |
| 5J | $C_6H_5-(CH_2)_3-$ | H | $4-CH_3O-C_6H_4-$ | trans | $4-CH_3-C_6H_4-$ | elemental analysis:<br>calc'd C = 81.01, H = 7.06,<br>N = 3.63;<br>found C = 81.25, H = 7.09,<br>N = 3.75 |
| 5K | $C_6H_5-(CH_2)_3-$ | H | $4-CH_3O-C_6H_4-$ | trans | $4-(C_6H_5-O)-C_6H_4-$ | elemental analysis:<br>calc'd C = 80.32, H = 6.31,<br>N = 3.02;<br>found C = 80.36, H = 6.29,<br>N = 3.16 |
| 5L | $C_6H_5-(CH_2)_3\cdots$ (phenyl) | H | 4-OCH$_3$-phenyl | trans<br>optically<br>pure | $C_6H_5-$ | mp = 74–75° C.<br>$[\alpha]_D^{25} = -7.6°$ |
| 5M | $C_6H_5-(CH_2)_3\blacktriangleright$ (phenyl) | H | 4-OCH$_3$-phenyl (wedge) | trans<br>optically<br>pure | $C_6H_5-$ | mp = 74–75° C.<br>$[\alpha]_D^{25} = -7.5°$ |
| 5P | $C_6H_5-(CH_2)_3-$ | H | 3,4-di-OCH$_3$-phenyl | trans | $4-CH_3O-C_6H_4-$ | mp = 70.5–71.5° C. |
| 5Q | $C_6H_5-(CH_2)_3-$ | H | 3,4-methylenedioxyphenyl | trans | $4-CH_3O-C_6H_4-$ | mp = 79.5–81.0° C. |
| 5R | $C_6H_5-(CH_2)_3-$ | H | $4-CH_3-C_6H_4-$ | trans | $4-CH_3O-C_6H_4-$ | mp = 74.5–77.0° C. |
| 5S | $C_6H_5-(CH_2)_3-$ | H | $4-(CH_3CH_2-O)-C_6H_4-$ | trans | $4-CH_3O-C_6H_4-$ | mp = 85–87° C. |
| 5T | $C_6H_5-(CH_2)_3-$ | H | $4-(C_6H_5-CH_2-O)-C_6H_4-$ | trans | $4-CH_3O-C_6H_4-$ | mp = 111–112° C. |
| 5U | $C_6H_5-(CH_2)_3-$ | H | $4-(CH_2=CH-CH_2-O)-C_6H_4-$ | trans | $4-CH_3O-C_6H_4-$ | mp = 75.5–77.0° C. |
| 5V | $C_6H_5-(CH_2)_3-$ | H | $4-(C_6H_5-O)-C_6H_4-$ | trans | $4-CH_3O-C_6H_4-$ | mp = 103.5–105.5° C. |
| 5W | $C_6H_5-(CH_2)_3-$ | H | $4-CH_3O-C_6H_4-$ | trans | $4-CH_3O-C_6H_4-$ | mp = 75–77° C. |
| 5X | $C_6H_5-O-(CH_2)_2-$ | H | $4-CH_3O-C_6H_4-$ | trans | $4-CH_3O-C_6H_4-$ | mp = 122–123° C. |
| 5Y | $C_6H_5-(CH_2)_6-$ | H | $4-CH_3O-C_6H_4-$ | trans | $4-CH_3O-C_6H_4-$ | elemental analysis:<br>calc'd C = 78.52, H = 7.50,<br>N = 3.16;<br>found C = 78.32, H = 7.37,<br>N = 3.25 |
| 5Z | $C_6H_5-(CH_2)_2-O-$ | H | $4-CH_3O-C_6H_4-$ | trans | $4-CH_3O-C_6H_4-$ | elemental analysis:<br>calc'd C = 74.42, H = 6.25,<br>N = 3.47;<br>found C = 74.57, H = 6.29,<br>N = 3.51 |
| 5AA | $4-F-C_6H_4-O-(CH_2)_2-$ | H | $4-CH_3O-C_6H_4-$ | trans | $4-MeO-C_6H_4-$ | elemental analysis:<br>calc'd C = 71.25, H = 5.74,<br>N = 3.32;<br>found C = 71.34, H = 5.73,<br>N = 3.43 |
| 5AB | $C_6H_5-(CH_2)_4-$ | H | $4-CH_3O-C_6H_4-$ | trans | $4-MeO-C_6H_4-$ | elemental analysis:<br>calc'd C = 78.04, H = 7.03,<br>N = 3.37;<br>found C = 77.90, H = 6.94,<br>N = 3.51 |

-continued

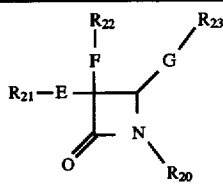

| Ex. | $R_{21}-E-$ | $R_{22}-F-$ | $R_{23}-G-$ | Rel. Stereochemistry | $R_{20}$ | Data |
|---|---|---|---|---|---|---|
| 5A | $(CH_3)_2CH-$ | H | $C_6H_5-$ | 3S,4R | $4\text{-MeO}-C_6H_4-$ | mp = 113–115° C. |
| 5N | $C_6H_5-(CH_2)_2-N(CH_3)$ | H | $4\text{-CH}_3O-C_6H_4-$ | trans | $C_6H_5-$ | mp = 122–123° C. |

EXAMPLE 6

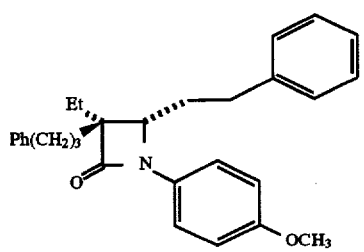

Dissolve 200 mg (0.47 mmol) of the β-lactam of Example 3G in 4 mL EtOAc and add ~10 mg 10% Pd/C. Hydrogenate at 1 atm for 4 h. Filter the mixture through Celite and concentrate. Chromatograph the residue over 40 g $SiO_2$, eluting with 20% EtOAc-hexane to obtain 188 mg (94%) of the title β-lactam as a colorless oil. CI MS :(M+1) 428.1.

EXAMPLE 7

To a refluxing solution of 4.33 grams (0.0205 moles) N-(4-methoxybenzylidine)-aniline and 7.6 grams (0.0410 moles) tributylamine in 40 mL heptane add, in portions, a solution of 4.03 grams (0.0205 moles) 5-phenylvaleroyl chloride in 15 mL heptane over about 2 hours, then reflux the solution for an additional 4 hours. Evaporate the solvent and take up the residue in 150 mL EtOAc. Wash with 1N HCl (2×30 mL), saturated $NaHCO_3$ (1×30 mL) and brine (1×30 mL), then dry over $MgSO_4$ and evaporate to give 7.69 grams of a semisolid. Recrystallization from 15% EtOAc in hexane to obtain 3.08 grams of the title compound, mp 75°–76° C. An additional 2.31 g is obtained from the mother liquors by chromatography (silica gel, 5% ethyl acetate in hexane) and recrystallization.

Using a procedure similar to that of Example 7, the following compounds shown in Tables 7 and 7A can be prepared:

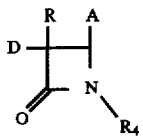

| Ex. | D | R | A | Relative Stereochemistry | $R_4$ | Data |
|---|---|---|---|---|---|---|
| 7A | $C_6H_5-(CH_2)_3-$ | H | $4\text{-CH}_3O-C_6H_4-$ | trans | $4\text{-}(CH_3CH_2OC(O))-C_6H_4-$ | mp = 75–77° C. |
| 7B | $C_6H_5-(CH_2)_3-$ | H | $4\text{-CH}_3O-C_6H_4-$ | trans | $3\text{-NO}_2-C_6H_4-$ | elemental analysis: calc'd C = 72.10, H = 5.81, N = 6.73; found C = 72.46, H = 5.91, N = 6.54 |
| 7C | $C_6H_5-(CH_2)_3-$ | H | $4\text{-CH}_3O-C_6H_4-$ | trans | $4\text{-}((CH_3CH_2)_2-N)-C_6H_4-$ | mp = 91–93° C. |
| 7D | $C_6H_5-(CH_2)_3-$ | H | $4\text{-CH}_3O-C_6H_4-$ | trans | $4\text{-NC}-C_6H_4-$ | mp = 79–81° C. |

| | | | | | | |
|---|---|---|---|---|---|---|
| 7E | C₆H₅—(CH₂)₃— | H | 4-CH₃O—C₆H₄— | trans | 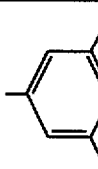 | elemental analysis: calc'd C = 73.69, H = 5.69, N = 3.44; found C = 73.36, H = 5.77 N = 3.48 |
| 7F | C₆H₅—(CH₂)₃— | H | 4-CH₃O—C₆H₄— | trans | 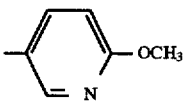 | mp = 103–104° C. |
| 7G | C₆H₅—(CH₂)₃— | H | 4-CH₃O—C₆H₄— | trans | 4-(CH₃C(O))—C₆H₄— | elemental analysis: calc'd C = 78.42, H = 6.58, N = 3.39; found C = 78.08, H = 6.51, N = 3.40 |
| 7H | C₆H₅—(CH₂)₃— | H | 4-CH₃O—C₆H₄— | trans | 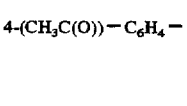 | mp = 90–92° C. |
| 7I | C₆H₅—(CH₂)₃— | H | 4-CH₃O—C₆H₄— | trans | 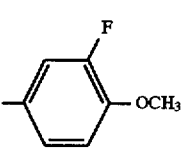 | mp = 129–130° C. |
| 7M | C₆H₅—(CH₂)₃— | H | 4-((CH₃)₂CH—O)—C₆H₄— | trans | 4-CH₃O—C₆H₄— | mp = 96.5–97.5° C. |
| 7O | C₆H₅—(CH₂)₃— | H | 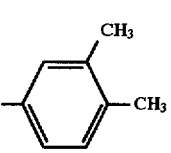 | trans | C₆H₅— | mp = 89–91° C. |
| 7P | C₆H₅—(CH₂)₃— | H | 4-(CH₃(CH₂)₂—O)—C₆H₄— | trans | 4-CH₃O—C₆H₄— | mp = 92.5–93.5° C. |
| 7Q | C₆H₅—(CH₂)₃— | H | 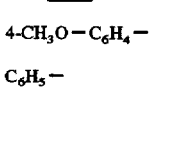 | trans | 4-CH₃O—C₆H₄— | EIMS (M) = 415 |
| 7R | C₆H₅—(CH₂)₃— | H | 4-(CH₃OC(O))—C₆H₄— | trans | C₆H₅— | mp = 84–85° C. |
| 7S | C₆H₅—(CH₂)₃— | H | 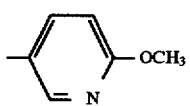 | trans | 4-CH₃O—C₆H₄— | EIMS (M) = 420 |
| 7T | C₆H₅—(CH₂)₃— | H | 4-(CH₃OCH₂O)—C₆H₄— | trans | C₆H₅— | CIMS (M + 1) = 402 |
| 7U | C₆H₅—(CH₂)₃— | H | 4-((CH₃)₂N)—C₆H₄— | trans | 4-CH₃O—C₆H₄— | mp = 96.5–97.5° C. |
| 7V | C₆H₅—(CH₂)₃— | H | 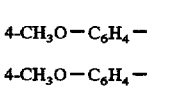 | trans | 4-CH₃O—C₆H₄— | EIMS (M) = 429 |
| 7W | C₆H₅—(CH₂)₃— | H | 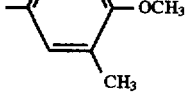 | cis | 4-CH₃O—C₆H₄— | EIMS (M) = 429 |
| 7X | C₆H₅—(CH₂)₃— | H | 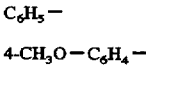 | trans | 4-CH₃O—C₆H₄— | EIMS (M) = 431 |

-continued

| | | | | | | |
|---|---|---|---|---|---|---|
| 7Y | $C_6H_5-(CH_2)_3-$ | H | $4-(CH_3CH_2-O)-C_6H_4-$ | trans | $C_6H_5-$ | mp = 95.0–95.5° C. |
| 7Z | $4-O_2N-C_6H_4-(CH_2)_3-$ | H | $4-CH_3O-C_6H_4-$ | trans | $4-CH_3O-C_6H_4-$ | mp = 136.5–137.0° C. |
| 7AA | $C_6H_5-(CH_2)_3-$ | H | $4-CH_3O-C_6H_4-$ | trans | $4-I-C_6H_4-$ | mp = 96.5–97.5° C. |
| 7AB | $C_6H_5-(CH_2)_3-$ | H | $4-(CH_3(CH_2)_3-O)-C_6H_4-$ | trans | $4-CH_3O-C_6H_4-$ | mp = 79–82° C. |
| 7AE | $C_6H_5-(CH_2)_2-O-$ | H | $4-CH_3O-C_6H_4-$ | cis | $4-CH_3O-C_6H_4-$ | mp = 149–150° C. |
| 7AI | 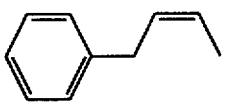 | H | $4-CH_3O-C_6H_4-$ | trans | $4-CH_3O-C_6H_4-$ | elemental analysis: calc'd C = 78.17, H = 6.31, N = 3.51; found C = 78.22, H = 6.36, N = 3.59 |
| 7AJ | 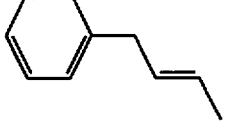 | H | $4-CH_3O-C_6H_4-$ | trans | $4-CH_3O-C_6H_4-$ | FAB mass spec 400 (100) |
| 7AK | 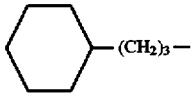 | H | $4-CH_3O-C_6H_4-$ | trans | $4-CH_3O-C_6H_4-$ | mp = 105–106° C. |
| 7AM | $C_6H_5-(CH_2)_5-$ | H | $4-CH_3O-C_6H_4-$ | trans | $4-CH_3O-C_6H_4-$ | elemental analysis: calc'd C = 78.29, H = 7.27, N = 3.26; found C = 78.37, H = 7.26, N = 3.41 |
| 7AN | $4-O_2N-C_6H_4-O-(CH_2)_2-$ | H | $4-CH_3O-C_6H_4-$ | trans | $C_6H_5-$ | mp = 54–56° C. |
| 7AO | 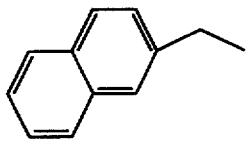 | H | $4-CH_3O-C_6H_4-$ | trans | $C_6H_5-$ | mp = 55–57° C. |
| 7AP | $4-(CH_3O)-C_6H_4-O-(CH_2)_2-$ | H | $4-CH_3O-C_6H_4-$ | trans | $C_6H_5-$ | elemental analysis: calc'd C = 74.42, H = 6.25, N = 3.47; found C = 74.13, H = 6.03, N = 3.26 |
| 7AQ | 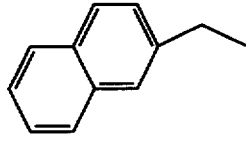 | H | $4-CH_3O-C_6H_4-$ | cis | $C_6H_5-$ | $^1$H NMR (CDCl$_3$) 7.97–7.78(m, 2H); 7.69(d, J=8Hz, 1H); 7.45–7.69(m, 10H); 6.90(d, J=8Hz, 2H); 6.63(d, J=8Hz, 1H); 5.17(d, J=6Hz, 1H); 4.15–4.0(m, 1H); 3.82(s, 2H); 3.5(dd, J=6, 14Hz, 1H); 2.96(dd, J=9, 14Hz, 1H) |
| 7AR | $C_6H_4-(CH_2)_3-$ | H | $4-CH_3O-C_6H_4-$ | trans | 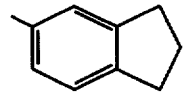 | mp = 111–112° C. |
| 7AS | $C_6H_4-(CH_2)_3-$ | H | $4-CH_3O-C_6H_4-$ | trans | 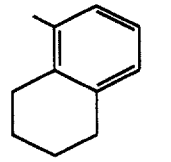 | MS CI+ (M + 1) = 426 |
| 7AT | $C_6H_4-(CH_2)_3-$ | H | $4-CH_3O-C_6H_4-$ | trans | 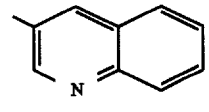 | mp = 122–124° C. |
| 7AU | $C_6H_4-(CH_2)_3-$ | H | $4-(C_6H_5-CH_2O)-C_6H_4-$ | trans | $4-(C_6H_5-CH_2O)-C_6H_4$ | mp = 105–106° C. |

-continued

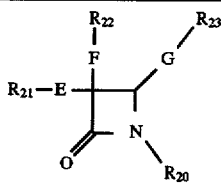

| Ex. | $R_{21}$—E— | $R_{22}$—F— | $R_{23}$—G— | Rel. Stereo-chemistry | $R_{20}$ | Data |
|---|---|---|---|---|---|---|
| 7J | $CH_3O-C(O)-CH=C(CH_3)-NH-$ | H | $4\text{-}CH_3O-C_6H_4-$ | cis | $C_6H_5-$ | mp = 186–187° C. |
| 7K | $C_6H_5-(CH_2)_2-N(CH_3)-$ | H | $4\text{-}CH_3O-C_6H_4-$ | cis | $C_6H_5-$ | mp = 120–123° C. |
| 7L | 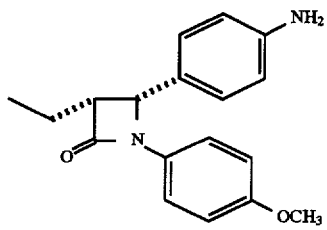 | H | $4\text{-}CH_3O-C_6H_4-$ | cis | $C_6H_5-$ | mp = 243–245.5° C. |
| 7N | $C_6H_5-(CH_2)_3-$ | H | $-C(O)OCH_2CH_3$ | cis | $4\text{-}CH_3O-C_6H_4-$ | mp = 97–98.5° C. |
| 7AC | $C_6H_5-$ | $C_6H_5-$ | $4\text{-}CH_3O-C_6H_4-$ | — | $4\text{-}CH_3O-C_6H_4-$ | mp = 78–81° C. |
| 7AD | cyclo-$C_5H_9-$ | $C_6H_5-$ | $4\text{-}CH_3O-C_6H_4-$ | trans | $4\text{-}CH_3O-C_6H_4-$ | mp = 60–63° C. |
| 7AF | $C_6H_5-$ | $C_6H_5-CH_2-$ | $4\text{-}CH_3O-C_6H_4-$ | cis | $4\text{-}CH_3O-C_6H_4-$ | mp = 108–110° C. |
| 7AG | $C_{10}H_{21}-$ | H | $4\text{-}CH_2O-C_6H_4-$ | trans | $4\text{-}CH_3O-C_6H_4-$ | elemental analysis: calc'd C = 76.56, H = 8.80, N = 3.31; found C = 76.37, H = 8.90, N = 3.46 |
| 7AH | $C_6H_5-CH_2-$ | $C_6H_5-$ | $4\text{-}CH_3O-C_6H_4-$ | cis | $4\text{-}CH_3O-C_6H_4-$ | mp = 114–117° C. |
| 7AL |  naphthyl-O— | H | $4\text{-}CH_3O-C_6H_4-$ | cis | $4\text{-}CH_3O-C_6H_4-$ | elemental analysis: calc'd C = 76.22, H = 5.45, N = 3.29; found C = 76.00, H = 5.46, N = 3.39 |

EXAMPLE 8

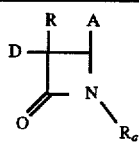

Stir a mixture of 981 mg (3.01 mmol) of the cis β-lactam of Example 1AK, above, and 20 mg 10% palladium on carbon in 10 mL ethyl acetate under 1 atm hydrogen gas at room temperature for 24 h. Filter the mixture through Celite and concentrate in vacuo. Chromatograph the residue over 50 g $SiO_2$, eluting with 40% ethyl acetate-hexane to obtain 818 mg (92%) of the title compound as a yellowish solid, mp=142.0°–142.5° C.

Using a similar procedure, the following compounds shown in Tables 8 and 8A can be prepared, and using conventional procedures, the amino group of compound 8A and the amino group of compound 8B can be protected with a t-butoxycarbonyl (BOC) group to obtain compounds 8G and 8H, respectively:

| Ex. | D | R | A | Relative Stereochemistry | $R_4$ | Data |
|---|---|---|---|---|---|---|
| 8B | $C_6H_5-(CH_2)_3-$ | H | $4\text{-}NH_2-C_6H_4-$ | cis | $4\text{-}CH_3O-C_6H_4-$ | mp = 138.5–139.5° C. |
| 8C | $C_6H_5-(CH_2)_3-$ | H | $4\text{-}NH_2-C_6H_4-$ | trans | $4\text{-}CH_3O-C_6H_4-$ | FAB MS (M + 1) = 387.1 |
| 8D | $C_6H_5-(CH_2)_3-$ | H | $4\text{-}CH_3O-C_6H_4-$ | trans | $4\text{-}NH_2O-C_6H_4-$ | mp = 46–48° C. |
| 8E | $4\text{-}NH_2-C_6H_4-(CH_2)_3-$ | H | $4\text{-}CH_3O-C_6H_4-$ | trans | $4\text{-}CH_3O-C_6H_4-$ | mp = 129.0–131.0° C. |
| 8F | $C_6H_5-(CH_2)_3-$ | H | $4\text{-}OH-C_6H_4-$ | trans | $4\text{-}CH_3O-C_6H_4-$ | mp = 171.0–171.5° C. |
| 8H | $C_6H_5-(CH_2)_3-$ | H | $4((CH_3)_3C-O-C(O)-NH)-C_6H_4-$ | cis | $4\text{-}CH_3O-C_6H_4-$ | CI MS: (M + 1) = 487 |

-continued

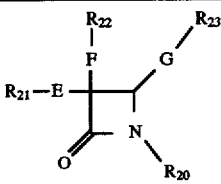

| Ex. | $R_{21}$—E— | $R_{22}$—F— | $R_{23}$—G— | Rel. Stereochemistry | $R_{20}$ | Data |
|---|---|---|---|---|---|---|
| 8A | $CH_3CH_2$— | H | 4-$NH_2$—$C_6H_4$— | 3S,4R | 4-$CH_3O$—$C_6H_4$— | mp = 136–137° C. |
| 8G | $CH_3CH_2$— | H | 4(($CH_3$)$_3$C—O—C(O)—NH)—$C_6H_4$— | 3S,4R | 4-$CH_3O$—$C_6H_4$— | CI MS: (M + 1) = 397 |

EXAMPLE 9

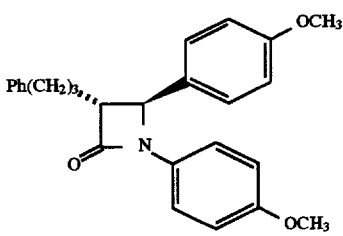

STEP 1: Combine 5-phenylvaleric acid (89.9 g, 0.504 mol) and thionyl chloride (89.3 mL, 1.225 mol), heat to 70° C. and reflux for 1 h. Vacuum distill (50–100 mm Hg) the excess thionyl chloride and add 200 mL of dry toluene to the resultant residue. Vacuum distill again, then add 188 mL of dry THF to the crude 5-phenylvaleroyl chloride and use the resulting solution directly in the next step.

STEP 2: Combine 76 g (0.4289 mol) of R-(+)-4-benzyloxazolidinone and 1.3L of dry THF under dry nitrogen atmosphere. Cool the resulting solution to −78° C. and add 278 mL of a 1.6M solution of n-butyllithium in hexane over 30–40 minutes. Stir for an additional 30 minutes, then add the solution of Step 1 over a pedod of 45 min. Allow the mixture to warm to 0° C. and stir for 1 h. Quench the reaction mixture by adding 673.6 mL of $K_2CO_3$ (1M aqueous solution) and stir for 1 h. Distill off the THF under vacuum at 30°–35° C. Dilute the residue with 1L of water and extract with 3×800 mL of $CH_2Cl_2$. Combine the organic extracts and wash with 800 mL of water, then with 800 mL of brine. Dry the organic extracts over $MgSO_4$, filter, then concentrate in vacuo to an oil. Dissolve the oil in 200 mL of hexane, then distill off the hexane under vacuum. Repeat the hexane treatment two more times, then dissolve the oil in 1.7 mL of $CH_2Cl_2$. The resulting solution is used directly in the next step.

STEP 3: Cool the solution of Step 2 to −5° C. to 0° C. under dry nitrogen atmosphere. Add 129.8 mL of di-n-butylboron triflate, maintaining the temperature of the reaction mixture at −6° C. to −3° C. Following the addition, stir the mixture for 10 min., then add 97.12 mL of diisopropylethylamine, again maintaining the temperature at −6° C. to −3° C. Following the addition, stir the mixture at 0° C. for 30 min., then cool the mixture to −78° C. and stir for 30 min. Add 57.4 mL of p-anisaldehyde and stir the mixture at −78° C. for 30 min., then at 0° C. for 1 h. While maintaining the temperature at 0° C. to 5° C., quench the mixture by adding 688.2 mL of a pH 7 buffer solution (68 g $KH_2PO_4$, 12 g NaOH and 800 mL of water), then add 473 mL of 30% $H_2O_2$ and stir the resulting mixture at 0° C. for 1 h. Extract the mixture with 3×600 mL hexane:ethyl acrerate (1:1), combine the organic extracts and wash with 800 mL of saturated $NaHCO_3$ (aqueous), then with 800 mL of brine. Dry the organic extracts over $NaSO_4$, filter, and evaporate to an oil. Crystallize the oil from hexane/ethyl acetate (1:1) to give 176 g of the product as a white solid.

STEP 4: Combine the product of Step 3 (170 g, 0.36 Mol), 1595 mL of THF and 400 mL of water, stir the mixture and cool to about 3° C. Add 226 mL (2.156 Mol) of 30% $H_2O_2$ to the mixture over 15 min., then add a solution of LiOH (36.2 g, 0.862 Mol) in 400 mL of water over a period of 30 min. Stir the reaction mixture at 0° C. to 5° C. for 3 h. Add a solution of 272 g of sodium sulfite in 850 mL of water over 70 min., keeping the temperature under 27° C. Concentrate the solvent under vacuum and add 7L of water. Extract with 4×1.7L of toluene. Acidify the aqueous layers to pH 2.4 with 3N HCl. Extract with one 2.6L portion and two 1.7L portions of ethyl acetate. Combine the ethyl acetate extracts, wash with brine, dry over $NaSO_4$, filter, then evaporate to give the product as a white solid, 112 g.

STEP 5: Combine the product of Step 4 (19.47 g, 62 mmol), 400 mL of acetonitrile, 9.49 g (62 mmol) of 1-hydroxybenzotriazole (HOBT), 22.91 g (186 mmol) of p-anisidine and 14.05 g (68.2 mmol) of dicyclohexylcarbodiimide (DCC). Stir the reaction mixture at 40° C. for 4 h and confirm the consumption of starting material by TLC (6:4 hexane/ethyl acetate). Concentrate the mixture to ⅓ its volume and partition between 300 mL of water and 300 mL of ethyl acetate. Filter the organic layer, then wash with 200 mL of 1N HCl, then with two 100 mL portions of saturated $NaHCO_3$, and two 100 mL portions of brine. Dry the organic layer over $NaSO_4$ and concentrate to give the product as a brown solid, 24 g.

STEP 6: Combine the product of Step 5 (115 g, 0.2745 Mol) and 2.3L of THF under dry nitrogen atmosphere and cool to −70° C. Stir the mixture while adding a solution of 137 mL (0.551 Mol) of tri-n-butylphosphine in 113 mL THF, and 163 mL (1.03 Mol) of diethylazodicarboxylate (DEAD) over 2 h. Allow the mixture to warm to room temperature and stir overnight. Remove the solvent under vacuum. Filter the residue through a plug of silica gel using $CH_2Cl_2$/hexane/ethyl acetate (70:24:6) as the eluant. Evaporate the solvent and purify the residue by preparative HPLC (silica gel, 15% ethyl actetate/hexane) to give 88 g of the (3R,4S) enantiomerically pure title compound, $[\alpha]_D^{25}=-19.3°$ (MeOH).

EXAMPLE 10

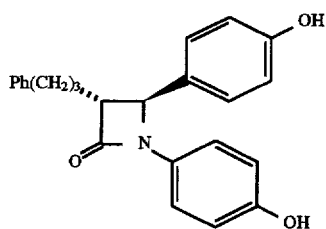

The compound of Example 7AU (0.686 g, 0.0012 moles) dissolved in 1:1 ethanol:ethyl acetate is hydrogenated over 0.70 grams 10% Pd on carbon at 50 psi for 16 hours. The resulting product is chromatographed (silica gel, 80:20 hexane:ethyl acetate) to give 0.432 grams of the title compound, mp 160°–161° C.

Using substantially the same procedure the following compound can be prepared:

EXAMPLE 10A

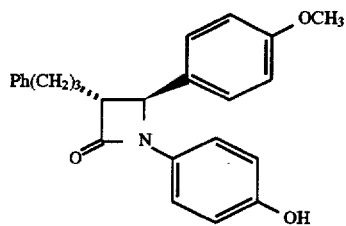

Elemental Analysis Calculated for $C_{25}H_{25}NO_3$ C, 77.49; H, 6.50; N, 3.61 Found: C, 77.47; H, 6.46; N, 3.74

EXAMPLE 11

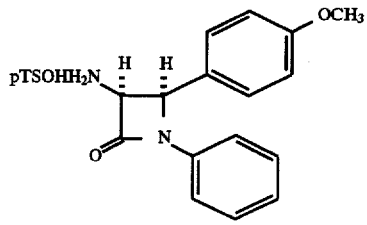

A flask is charged with the compound of Example 7J (27 g, 73.6 mmole), acetone (0.6 l), water (1.3 ml, 73 mmole), and p-toluenesulfonic acid-monohydrate (15.4 g, 81.1 mmole). The solution is stirred at 22° C. for 5.5 h and the product collected by filtration (34.1 g). Recrystallization from methanol affords the title compound,26.0 g (79% yield), mp 200°–202° C.

EXAMPLE 12

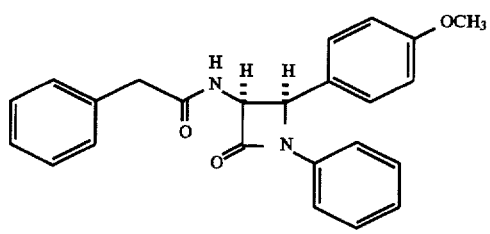

To a solution of the product of Example 11 (0.60 g, 1.36 mmole), triethylamine (0.14 g, 1.4 mmole) in $CH_2Cl_2$ (2 ml) was added phenylacetylchloride (0.310 g, 2.0 mmole) dropwise over 0.5 h. After 5 h the reaction mixture was concentrated to dryness, and the residue purified by chromatography (silica, 2:1 hexane: ethyl acetate) to afford 0.27 g (51% yield) of the title compound, mp 217°–218° C.

Using substantially the same procedure, the following compounds can be prepared:

Example 12A

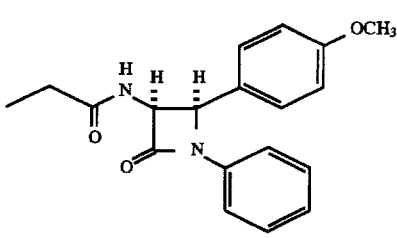

mp 167–168° C.

Example 12B

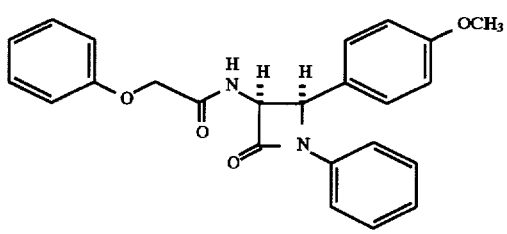

mp 192–193° C.

Example 12C

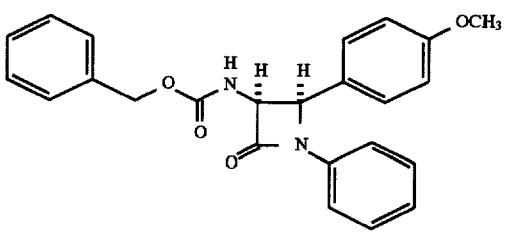

mp 194–195° C.

-continued
Example 12D

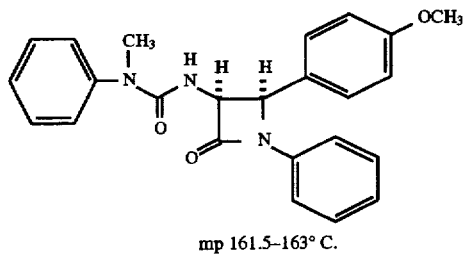

mp 161.5–163° C.

EXAMPLE 13

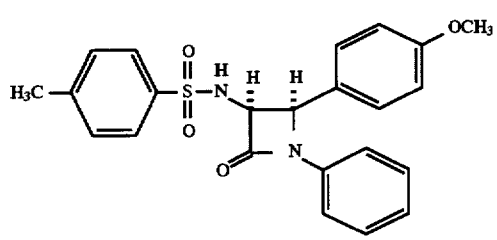

To a biphasic mixture of the product of Example 11 (0.80 g, 1.8 mmole), $CH_2Cl_2$ (15 ml) and 30% aqueous tetrabutylammonium hydroxide (2.36 ml, 3.64 mmole) was added p-toluenesulfonylchloride (0.515 g, 2.7 mmole). After 2 h the reaction mixture was washed with 1×1N HCl, 2×$H_2O$ and the organic layer dried over $MgSO_4$. Concentration followed by recrystillaztion from ethyl acetate afforded 0.38 g (50% yield) of the title compound, mp 204°–205° C.

EXAMPLE 14

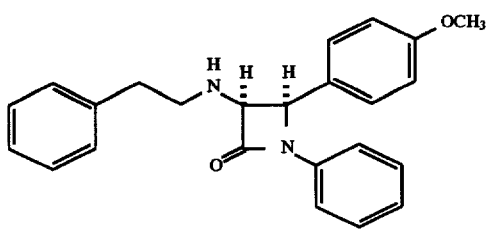

To a solution of the product of Example 11 (0.8 g, 1.8 mmole), methanol (20 ml) and triethylamine (0.19 g, 1.8 mmole) was added phenylacetaldehyde (0.44 g, 3.6 mmole). After 0.25 h, $NaBH_3CN$ (0.172 g, 2.7 mmole) and $ZnCl_2$ (0.174 g, 1.3 mmole) were added to the reaction. After 3.5 h, the reaction was quenched with ammonium chloride, concentrated partially in vacuo, and dissolved in $CH_2Cl_2$. The organic layer was washed 2× with water, dried and concentrated to afford crude product. Recrystallization from $CH_2Cl_2$ afforded 0.44 g (65% yield) of the title compound, mp 138°–139.5° C.

Using substantially the same procedure, the following compounds can be prepared:

Example 14A

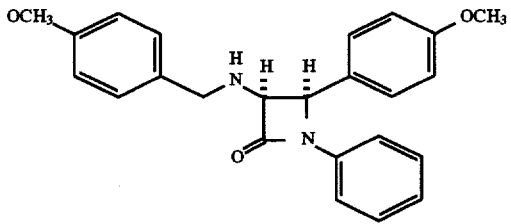

mp 148–149° C.

Example 14B

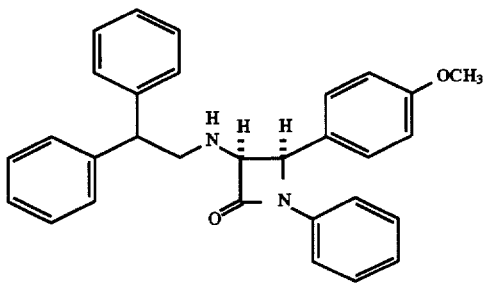

mp 179–180° C.

Example 14C

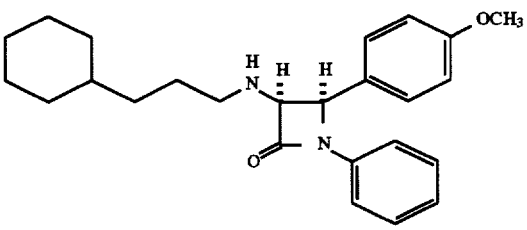

mp 100–101° C.

EXAMPLE 15

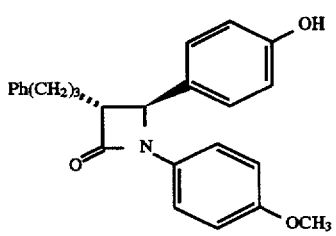

Add 49 mL (49 mmol) of 1M tetrabutylammonium fluoride 49 mL, 49 mmol, 1M in THF) to a room temperature solution of the compound of Example 1AS (5.1 g, 9.8 mmol)in THF (25 mL). Allow the mixture to stir overnight. TLC (50% EtOAc/hexanes) indicates consumption of starting material. Transfer the reaction mixture to a separatory funnel, partion between saturated ammonium chloride and ether, extract with ether. Combine the etheral extracts, wash with water and brine, dry over anhydrous $Na_2SO_4$, filter and concentrate to a residue. Chromatograph ($SIO_2$, 30–40% EtOAc/hexane) affords 3.31 g (84%) of the title compound, mp 91°–92° C.

The following compounds can be prepared via substantially the same procedure:

Example 15A

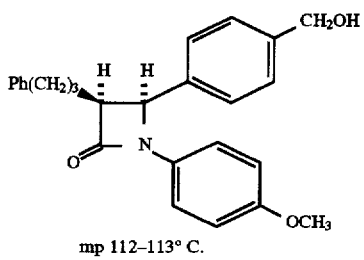

mp 112–113° C.

Example 15B

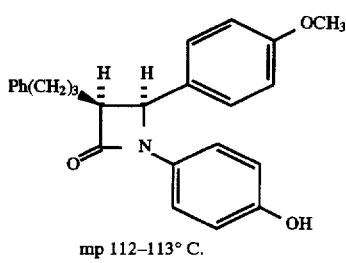

mp 112–113° C.

EXAMPLE 16

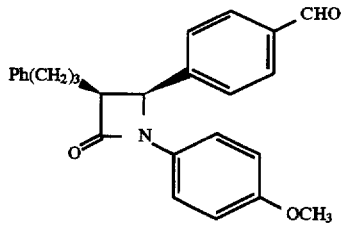

Add MnO$_2$ (0.64 g, 7.4 mmol) to a solution of the product of Example 15A (0.20 g, 0.5 mmol) in CH$_2$Cl$_2$ (50 mL) at room temperature. Allow the mixture to stir overnight. TLC (20% EtOAc/hexanes) indicates consumption of starting material. Filter the mixture through celite washing the filtercake well with CH$_2$Cl$_2$. Concentrate the flitrate to obtain 0.19 g (95%) of the title compound, mp 129°–130° C.

Using substantially the same procedure, the following compound can be prepared:

EXAMPLE 16A

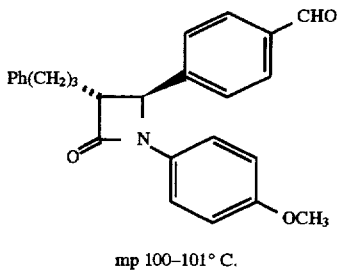

mp 100–101° C.

EXAMPLE 17

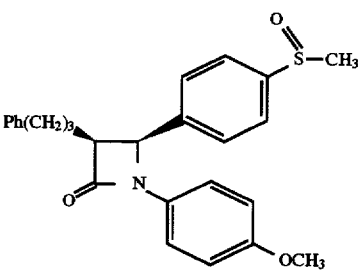

Add m-chloroperbenzoic acid (0.16 g, 0.092 mmol) to a solution of the compound of Example 1AU (0.31 g, 0.74 mmol) in CH$_2$Cl$_2$ (4 mL) at room temperature. Monitor the reaction by TLC (50% EtOAc/hexanes). Upon consumption of starting material (~1 h), add Ca(OH)$_2$ (0.1 g, 1.3 mmol) Stir the mixture for an additional 15 min. Filter the mixture through celite washing the filtercake well with CH$_2$Cl$_2$. Concentrate the flitrate onto silica gel, using enough silica gel until a free flowing powder is obtained. Load the resulting powder onto a chromatography column loaded with silica gel and 5% MeOH/CH$_2$Cl$_2$. Elute with 5% MeOH/CH$_2$Cl$_2$ to obtain 0.26 g of the title sulfoxide (Example 17), mp 134°–135° C. and 0.50 g of the analogous sulfone:

EXAMPLE 17A

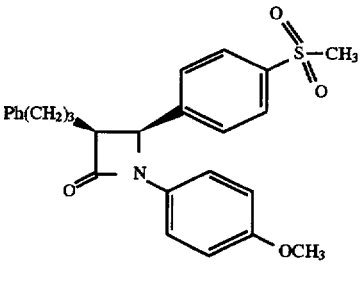

mp 116–117° C.

The following compounds can be prepared via substantially the same procedure:

Example 17B

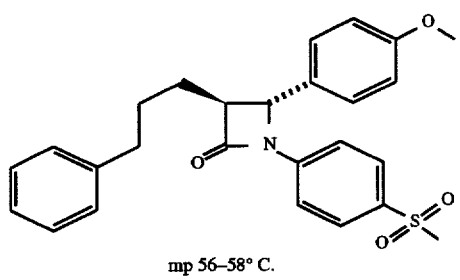

mp 56–58° C.

Example 17C

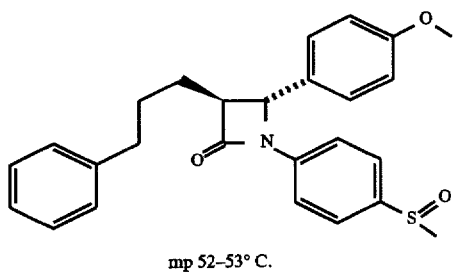

mp 52–53° C.

EXAMPLE 18

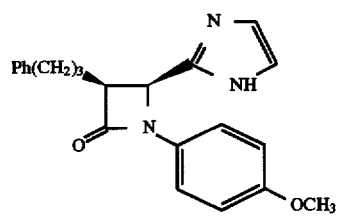

Reflux a mixture of the compound of Example 1AW (1.72 g, 3.49 mmol), 20 mL of THF and 3N HCl (20 mL) overnight. Monitor the reaction by TLC (50% EtOAc/hexanes). Upon consumption of starting material cool the mixture to room temperature, neutralize with saturated NaHCO$_3$ and extract with ethyl acetate. Combine the extracts, wash with water and brine, dry over anhydrous Na$_2$SO$_4$, filter and concentrate to a solid. Recrystallize from CH$_2$Cl$_2$/MeOH to obtain 0.322 g of the title compound, mp 190.5°–191.5° C.

Using substantially the same procedure the following compound can be prepared:

EXAMPLE 18A

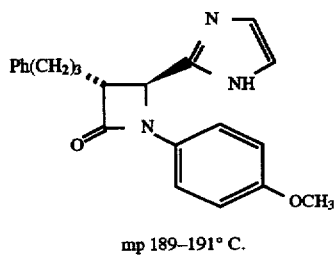

mp 189–191° C.

EXAMPLE 19

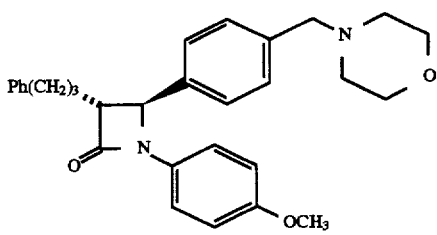

Add a solution of NaBH$_3$CN (0.19 g, 3.0 mmol) and ZnCl$_2$ (0.21 g, 1.5 mmol) in methanol to a room temperature solution of the product of Example 16A (1.0 g, 2.5 mmol) and morpholine (0.44 mL, 5.0 mmol) in THF. Monitor the reaction by TLC (50% EtOAc/hexanes). Upon consumption of starting material the mixture was diluted with 0.1N NaOH (120 mL) and remove the organic solvents on a rotary evaporator. Extract the resulting solution with ethyl acetate. Combine the extracts, wash with water and brine, dry over anhydrous Na$_2$SO$_4$, filter and concentrate to a solid. Recrystallize from Et$_2$O/hexanes to obtain 0.81 g (69%) of the title compound, mp 100°–101° C.

The following compounds can be prepared by substantially the same method:

Example 19A

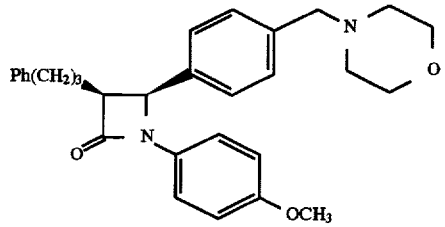

mp 97–98° C.

Example 19B

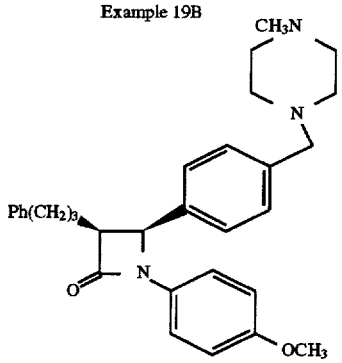

mp 141–142° C.

Example 19C

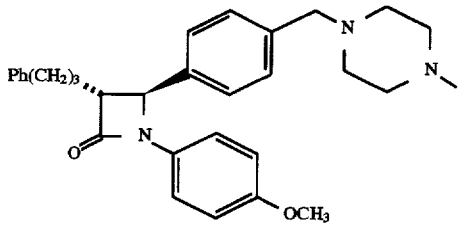

mp 103.5–104.5° C.

Example 19D

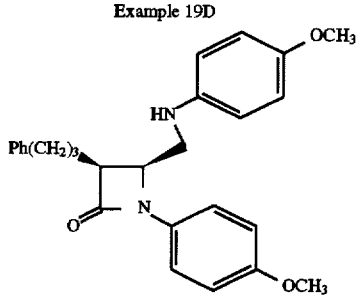

mp 94–95° C.

Example 19E

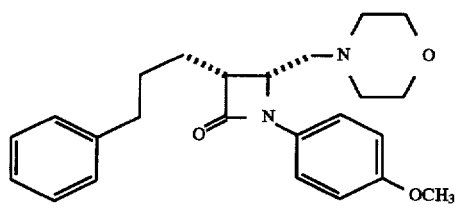

EI MS (M) = 394

EXAMPLE 20

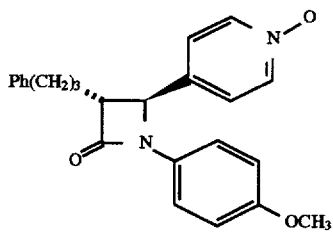

Heat a solution of the compound of Example 1AR (1.10 g, 2.95 mmol), 15% $H_2O_2$ (0.45 mL) in acetic acid (3 mL) to a 100° C. for 3.5 h with TLC monitoring (5% MeOH/ $CH_2Cl_2$). Upon consumption of the starting compound, cool to room temperature, neutralize with sat. $Na_2CO_3$ and dilute with ethyl acetate. Filter the mixture and wash the flitrate with water and brine, dry over anhydrous $Na_2SO_4$, filter and concentrate to a residue. Chromatograph the residue (silica gel, 10% MeOH/$CH_2Cl_2$) to give the title compound. FAB MS (M+1)=389.

EXAMPLE 21

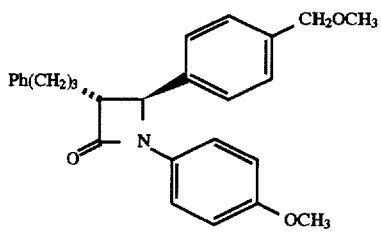

Add freshly prepared AgO (0.40 g, 1.73 mmol) to a solution of the product of Example 15A (0.46 g, 1.1 5 mmol) and methyl iodide (0.21 mL, 3.45 mmol) in dry DMF (5 mL). Heat the mixture to 40°–45° C. with TLC monitoring (50% EtOAc/hexanes). Add proportional amounts of AgO and methyl iodide until TLC indicates consumption of starting compound. Cool to room temperature, partion between water and ethyl acetate, extract with ethyl acetate. Combine ethyl acetate extracts, wash with water and brine, dry over anhydrous $Na_2SO_4$, filter and concentrate to a residue. Chromatograph the residue (silica gel, 30% EtOAc/ hexanes) to give the title compound. FAB MS (M+1)=416.

The following compound can be prepared by substantially the same procedure:

EXAMPLE 21A

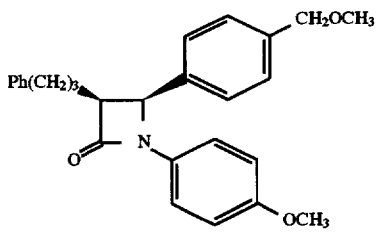

mp 84–85° C.

EXAMPLE 22

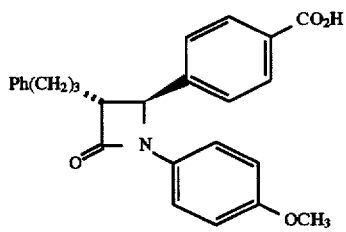

Add freshly prepared Jone's reagent (8 mL) dropwise to a solution of the product of Example 16 (2.76, 6.94 mmol) in acetone (80 mL) maintaining the temperature of the reaction mixture between 15°–20° C. Monitor by TLC (5% MeOH/CH$_2$Cl$_2$). Upon consumption of starting compound, quench the reaction with methanol. Concentrate to a residue and partion the residue between CH$_2$Cl$_2$ and water. Extract with CH$_2$Cl$_2$, combine the extracts, wash with water, 10% Na$_2$SO$_3$ (aq) and brine, then dry over anhydrous Na$_2$SO$_4$. Filter and concentrate to afford 2.90 g of the title compound, mp 64°–65° C.

The following compound can be prepared by substantially the same procedure.

EXAMPLE 22A

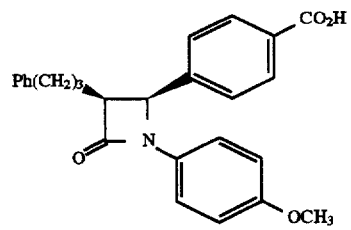

mp 158–159° C.

EXAMPLE 23

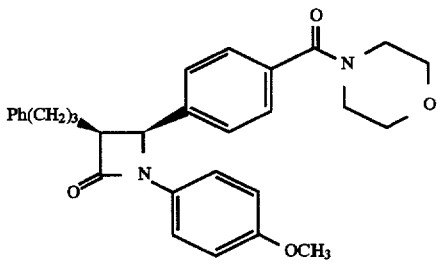

Add EDCl (0.2 g, 1.03 mmoL) to a room temperature solution of the product of Example 22A (0.30, 0.72 mmol), N-methylmorpholine (0.11 mL, 0.94 mmol), morpholine (0.13 mL, 0.42 mmol) and HOBT (0.12 g, 0.87 mmol) in CH$_2$Cl$_2$ (8 mL). Stir the mixture overnight. Monitor by TLC (5% MeOH/CH$_2$Cl$_2$). Upon consumption of the starting compound, dilute with CH$_2$Cl$_2$, wash with 1M HCl, water, dry over anhydrous Na$_2$SO$_4$, filter and concentrate to a residue. Chromatogaph the residue (SiO$_2$, 3% MeOH/CH$_2$Cl$_2$) to afford 0.3 g (86% yield) of the title compound, mp 61°–62° C.

EXAMPLE 24

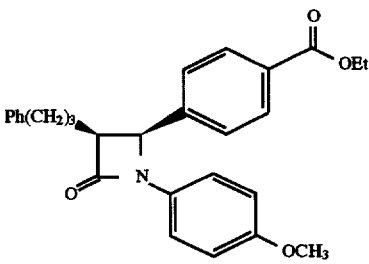

Add EDCl (0.2 g, 1.03 mmoL) to a room temperature solution of the product of Example 22A (0.30, 0.72 mmol), N-methylmorpholine (0.11 mL, 0.94 mmol), ethanol (0.1 mL, 1.44 mmol) and HOBT (0.12 g, 0.87 mmol) in CH$_2$Cl$_2$ (8 mL). Stir the mixture overnight. Monitor by TLC (5% MeOH/CH$_2$Cl$_2$). Upon consumption of starting compound, dilute with CH$_2$Cl$_2$, wash with 1M HCl, water, dry over anhydrous Na$_2$SO$_4$, filter and concentrate to a residue. Chromatogaph the residue (SiO$_2$, 3% MeOH/CH$_2$Cl$_2$) to afford 0.33 g (100% yield) of the title compound, mp 76°–77° C.

The following compound can be prepared by substantially the same procedure:

EXAMPLE 24A

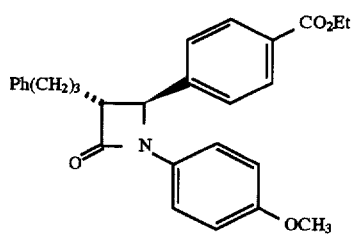

mp 74–75° C.

Add methanesulfonyl chloride (0.05 mL, 0.67 mmoL) to a 0° C. solution of the product of Example 8B (0.26, 0.67 mmol), pyridine(3 drops) in CH$_2$Cl$_2$ (5 mL). Stir the mixture overnight. Monitor by TLC (50% EtOAc/hexanes). Upon consumption of starting material, dilute with CH$_2$Cl$_2$, wash with 0.5M HCl, 5% NaHCO$_3$, water and brine, dry over anhydrous sodium sulfate, filter and concentrate to a residue. Chromatogaph the residue (SiO$_2$, 50% EtOAc/hexanes) to afford 0.18 g (58% yield) of the title compound, FAB MS (M+1)=465.

By substantially the same procedure, the following compounds can be prepared:

EXAMPLE 25

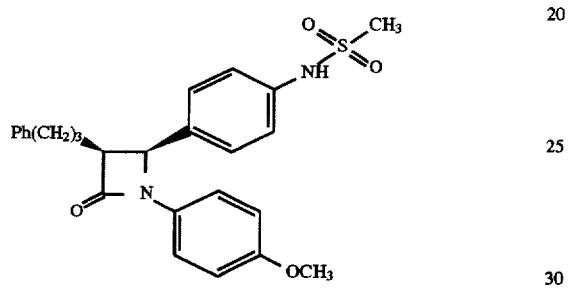

Example 25A

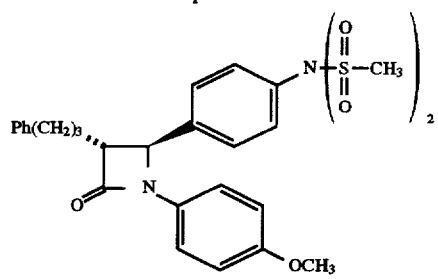

mp 170.5–171.5° C.

Example 25B

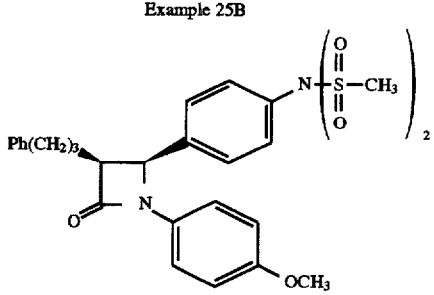

mp 175–176° C.

Example 25C

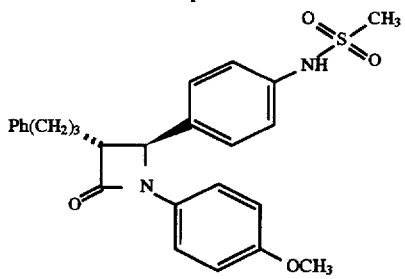

EI MS (M) = 542

EXAMPLE 26

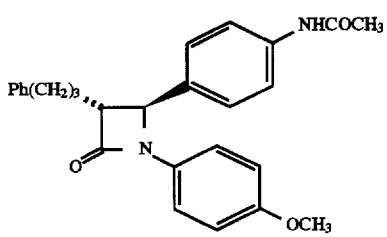

Add acetyl chloride (0.04 mL, 0.57 mmoL) to a solution of the product of Example 8C (0.20, 0.52 mmol) and triethylamine(0.11 mL, 0.79) in $CH_2Cl_2$ (3 mL) at room temperature. Monitor by TLC (50% EtOAc/hexanes). Upon consumption of starting material (~3h), dilute with $CH_2Cl_2$, wash with 5% $NaHCO_3$, water and brine, dry over anhydrous $Na_2SO_4$, filter and concentrate to afford 0.19 g (85% yield) of the title compound, mp 153°–154° C.

EXAMPLE 27

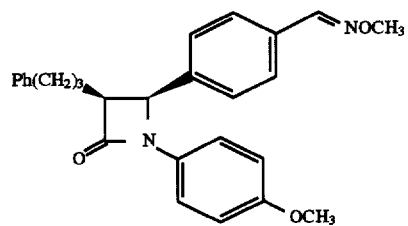

Reflux a suspension of the product of Example 16 (0.6 g, 1.5 mmol), hydroxylamine hydrochloride (0.4 g, 4.5 mmoL), sodium acetate (0.4 g 4.5 mmol), methanol (12 mL) and water (5 mL) overnight. Monitor by TLC (50% EtOAc/hexanes). Upon consumption of starting material, evaporate to dryness, partition the residue between water and ethyl acetate, extract with EtOAc, combine the extracts, wash with water and brine, dry over anhydrous $Na_2SO_4$, filter and concentrate to a residue. Chromatograph the residue (silica gel, 20% EtOAc/hexanes) to provide the title compound, mp 98°–99° C.; and Example 27A:

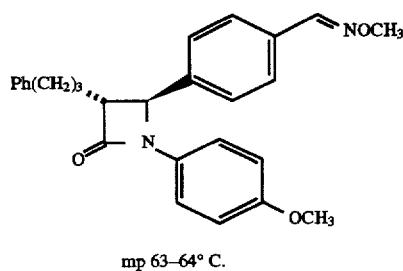

mp 63–64° C.

EXAMPLE 28

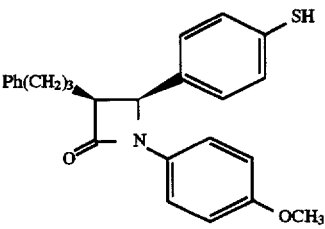

Reflux a solution of the product of Example 17 (3.2 g, 7.38 mmol), $CH_2Cl_2$ (15 mL) trifluoracetic anhydride (15 mL) for 15 min. Monitor the reaction by TLC (100% EtOAc). Upon consumption of starting material, distill to remove most of solvent, cool to room temperature, and evaporate to a residue. Dissolve the residue in 50% triethylamine/methanol solution (30 mL) stir for 15 min., evaporate to dryness on a rotovap. Redissolve in $CH_2Cl_2$, wash with $NH_4Cl$ (sat.), dry over anhydrous $Na_2SO_4$, filter and concentrate onto enough silica gel (1 g $SiO_2$/mmol substrate) that a free flowing powder results. Load the powder onto a chromatography column packed with silica gel and 30% EtOAc/hexanes. Elute with 30–60% EtOAc/hexanes to provide 2.65 g (89%) of a residue. Recrystallize from $Et_2O/CH_2Cl_2$ to give the title compound, mp 134°–135° C.

EXAMPLE 29

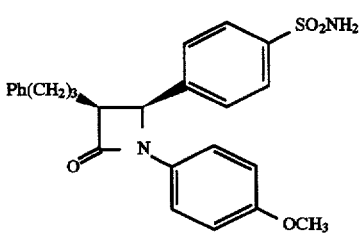

Dissolve the product of Example 28 ( 1.81 g, 4.49 mmol) in THF (25 mL) cool to 0° C. Add 1N NaOH (5.39 mL, 5.39 mmol), and a solution of aqueous ammonia (16.8 mL, 5.39 mmol), followed by cholorox (6.7 mL, 5.39 mmol). Monitor the reaction by TLC (50% EtOAc/hexane). Upon consumption of starting material, dilute with EtOAc, wash with water and brine, dry over anhydrous $Na_2SO_4$ and concentrate to provide the sulfinamine (1.88 g).

Dissolve the sulfinamine (1.88 g, 4.49 mmol) in $CH_2Cl_2$ (50 mL), add m-chloroperbenzoic acid (1.70 g, 9.88 mmol). Monitor the reaction by TLC (50% EtOAc/hexane). Upon consumption of starting material, quench with solid $Ca(OH)_2$ (1.78 g, 24.0 mmol), stir for 20 min., filter and concentrate onto enough silica gel (1 g $SiO_2$/mmol substrate) that a free flowing powder results. Load the powder onto a chromatography column packed with silica gel and 50% EtOAc/hexanes. Elute with 50% EtOAc/hexanes to provide 0.49 g (24%) of the title compound, mp 174°–176° C.

EXAMPLE 30

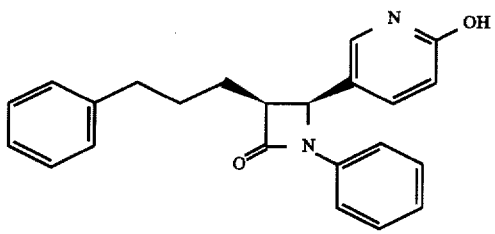

Add BBr$_3$ (5.15 mL, 5.15 mmol, 1M in CH$_2$Cl$_2$) to a 0° C. solution of the compound of Example 70 (0.768 g, 2.06 mmol) in CH$_2$Cl$_2$ (25 mL). Monitor the reaction by TLC (30% EtOAc). Upon consumption of starting material, quench with NaHCO$_3$ (sat.) and methanol, stir for 30 min., wash with NaHCO$_3$ (sat.) and water, dry over anhydrous Na$_2$SO$_4$, filter and concentrate onto enough silica gel (1 g SiO2/mmol substrate) such that a free flowing powder results. Load the powder onto a chromatography column packed with silica gel and 100% EtOAc. Elute with 100% EtOAc followed by 5% MeOH/EtOAc to provide 0.234 g (32%) of the title compound, Cl MS (M+1)=359.

EXAMPLE 31

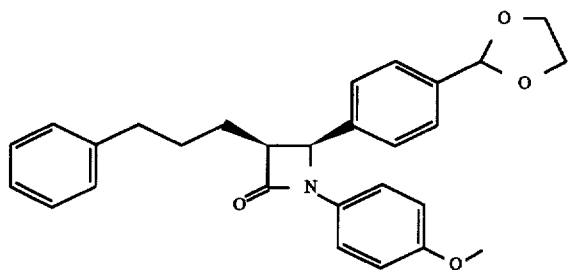

Reflux a mixture of the product of Example 16 (0.23 g, 0.6 mmol) ethylene glycol (0.2 mL, 3.6 mmol), p-toluene sulfonic acid and toluene (5 mL) overnight. Monitor by 1H NMR and TLC (50% EtOAc/hexanes). Cool to room temperature, wash with NaHCO$_3$(sat.), water and brine, dried over anhydrous Na$_2$SO$_4$, and concentrate to give 0.27 g (100%) of the title compound, EI MS (M)=443.

The following compound can be prepared by substantially the same procedure:

EXAMPLE 31A

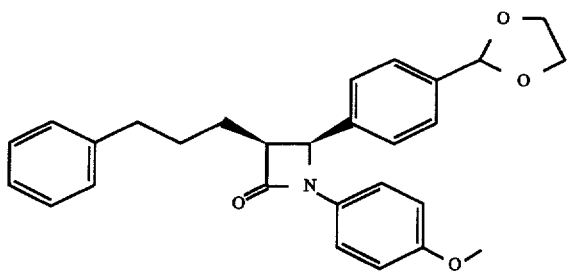

EI MS (M) = 443

EXAMPLE 32

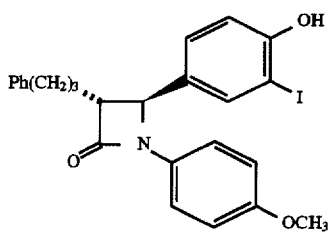

Stir a solution of 388 mg (1.00 mmol) of the compound of Example 8F, and 180 mg (1.20 mmol) chloramine-T NaI in 4.6 mL DMF. Add 377 mg (1.2 mmol) and stir for 18 h at room temperature. Partition the reaction between 30 mL 1N HCl and 30 mL ethyl acetate. Wash the organic layer with 10% aqueous Na$_2$SO$_3$ and dry the organic solution with MgSO$_4$. Concentrate in vacuo and chromatograph the residue over (silica gel, 40% ethyl acetate-hexane) to give 170 mg of the title compound, Cl MS (M+1)=514, and 41 mg of the diodo analog (Example 32A):

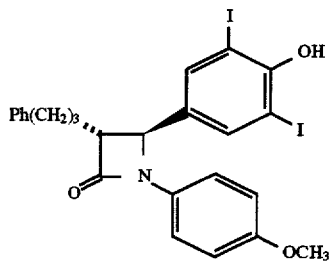

Cl MS (M + 1) = 640

EXAMPLE 33

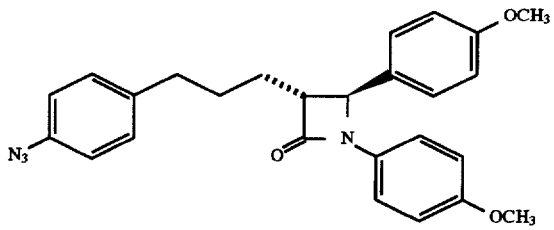

Stir 400 mg (0.96 mmol) of the compound of Example 8E, in 25 mL acetic acid and 5 mL water at 0° C. and add 133 mg (1.92 mmol) NaNO$_2$ in 4.7 mL water. Stir for 20 min. at 0° C. add 21 2 mg (3.26 mmol) NaN$_3$ in 9 mL water and stir for 3 h while warming to room temperature. Dilute with ethyl acetate and neutralize with NH$_4$OH. Dry the ethyl acetate layer with MgSO$_4$ and concentrate to a residue. Recrystallize the residue from ether-hexanes to give the titled compound, mp=80°–84° C.

EXAMPLE 34

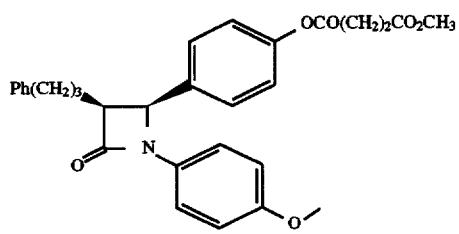

Dissolve 300 mg (0.77 mmol) of the compound of Example 8F, in 3 mL $CH_2Cl_2$ and add 98 µL (120 mg, 0.80 mmol) 3-carbomethoxypropionyl chloride and 146 µL (109 mg, 0.84 mmol) Hünig's base. Stir at room temperature for 1.5 h. Add another full portion of acid chloride and Hünig's base and stir for an additional hour. Partition the reaction between ethyl acetate and 1N HCl. Dry the ethyl acetate layer with $MgSO_4$ and concentrate to a residue. Chromatograh the residue ($SiO_2$, 40% ethyl acetate-hexane) and filter through grade I basic alumina eluting with 50% ethyl acetate-hexane to give 334 mg (86%) of the title compound, EI MS (M+)=501.25.

EXAMPLE 35

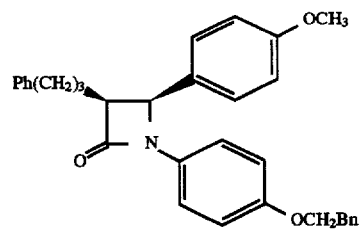

Benzyl bromide (0.44 g) was added to a solution of the compound of Example 15B (1.0 g) in acetone (15 mL) containing $K_2CO_3$ (0.715 g). The reaction was heated at reflux for 26 h. The reaction mixture was then poured into water and the product extracted with ethyl acetate. The crude product was recrystallized from ethyl acetate/hexane to give (0.908 g, 74% yield) of the desired product, mp 115°–116° C.

The following compounds were prepared via substantially the same procedure:

Example 35A

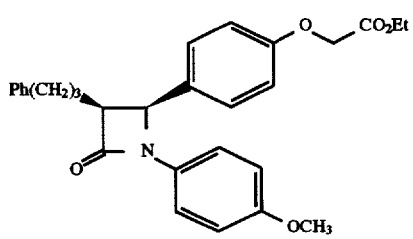

Cl MS (M + 1) = 474

EXAMPLE 36

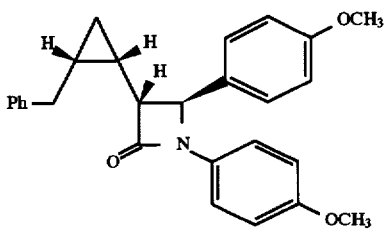

The compound of Example 7AI (0.19 g) was cooled to −20° C. To this ws added a solution of diethyl zinc in toluene(4.3 mL of a 1.1M solution) followed by diiodomethane (2.56 g). The reaction mixture was slowly allowed to warm to ambient temperature over three hours. Then the reaction mixture was warmed to 45° C. for 5 min. After cooling the reaction mixture was treated with aqueous $NH_4Cl$ and product extracted .with diethyl ether. The organic layer was washed with water, brine and concentrated to a residue. The residue was purified by chromatography ($SIO_2$, ethyl acetate/hexane (3:7)) to give the title compound (0.17 g, 88% yield). Elemental analysis: calculated-C, 78.42; H, 6.58; N, 3.39 found-C, 78.32; H, 6.48; N, 3.61.

EXAMPLE 37

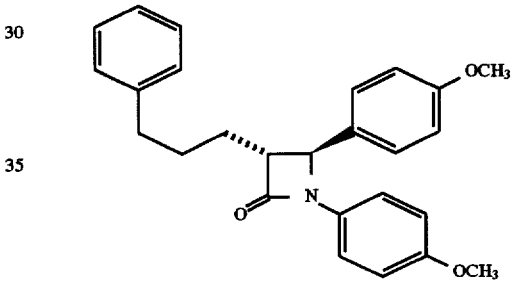

step (a)

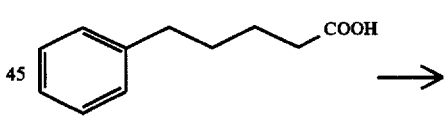

Example 35B

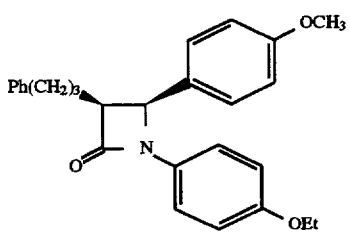

Elemental analysis:
calculated for $C_{27}H_{29}NO_3$:
C, 78.04; H, 7.03; N 3.37
Found: C, 78.00; H, 7.02;
N, 3.55

-continued

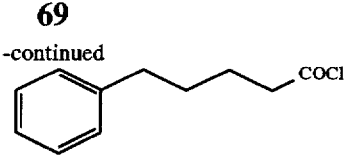

Combine 5-phenylvaleric acid (89.9 g, 0.504 mol) and SOCl₂ (89.3 mL, 1.225 mol) in a 500 mL round bottom flask equipped with a condenser and drying tube. Heat the flask to 70° C. and maintain the reaction at reflux for 1 h. Vacuum distill (50–100 mm Hg) the excess SOCl₂ and add 200 mL of dry toluene to the remaining mixture. Vacuum distill a second time to remove the toluene and any residual SOCl₂. Add 188 mL of dry THF to the crude acid chloride remaining in the reaction vessel and use the resulting solution directly in the next step.

step (b)

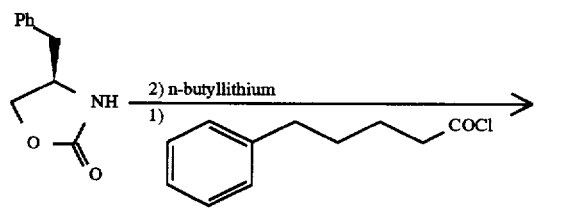

Combine 76 g (0.4289 mol) of R-(+)-4-benzyl-oxazolidinone and 1.3L of dry THF under dry nitrogen atmosphere. Cool the resulting solution to –78° C. and add 278 mL of a 1.6M solution of n-butyllithium in hexane over a period of 30–40 minutes. Stir the mixture for an additional 30 minutes following the addition. Add the solution of 5-phenylvaleroyl chloride from step (a) over a period of 45 minutes. Allow the mixture to warm to 0° C. and stir for 1 h. Quench the reaction mixture by adding 673.6 mL of K₂CO₃ (1M aqueous solution) and stir for 1 h. Distill off the THF Under vacuum at 30°–35° C. Dilute the residue with 1 L of water and extract with three 800 mL portions of CH₂Cl₂. Combine the organic extracts and wash with 800 mL of water, then with 800 mL of brine. Dry the organic extracts over MgSO₄, filter, then concentrate in vacuo to an oil. Dissolve the oil in 200 mL of hexane, then distill off the hexane under vacuum. Repeat the hexane treatment two more times, then dissolve the oil in 1.7 mL of CH₂Cl₂. The resulting solution is used directly in the next step.

step (c)

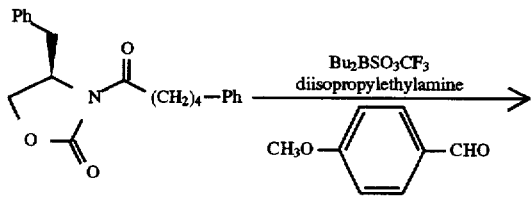

-continued

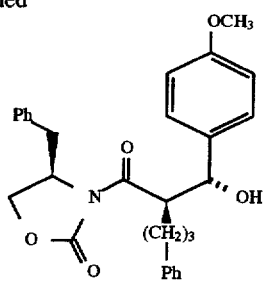

Cool the solution of the product from step (b) to –5° C. to 0° C., under dry nitrogen atmosphere. Add 129.8 mL of di-n-butylboron triflate at a rate that maintains the temperature of the reaction mixture at –6° C. to –3° C. Following the addition, stir the mixture for 10 minutes, then add 97.12 mL of diisopropylethylamine at a rate that maintains the temperature of the reaction mixture at –6° C. to –3° C. Following the addition, stir the mixture at 0° C. for 30 minutes, then cool the mixture to –78° C. and stir for 30 minutes. Add 57.4 mL of p-anisaldehyde and stir the mixture at –78° C. for 30 minutes, then at 0° C. for 1 h. While maintaining the temperature at 0° C. to 5° C., quench the mixture by adding 688.2 mL of a pH 7 buffer solution (68 g KH₂PO₄, 12 g NaOH and 800 mL of water), then add 473 mL of 30% H₂O₂ and stir the resulting mixture at 0° C. for 1 h. Extract the mixture with three 600 mL portions of hexane:ethyl actetate (1:1). Combine the organic extracts and wash with 800 mL of saturated NaHCO₃ (aqueous), then with 800 mL of brine. Dry the organic extracts over NaSO₄, filter, and evaporate to an oil. Crystallize the oil from hexane/ethyl acetate (1:1) to give 176 g of the product as a white solid.

step (d)

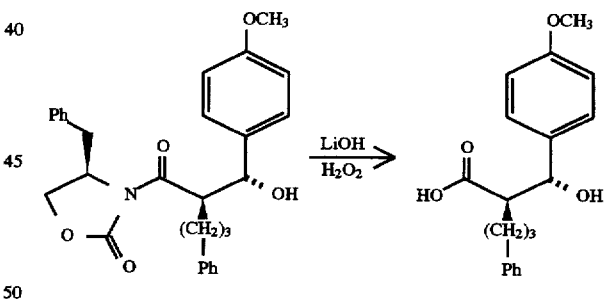

Combine the product of step (c) (170 g, 0.36 Mol), 1595 mL of THF and 400 mL of water, stir the mixture and cool to about 3° C. Add 226 mL (2.156 Mol) of 30% H₂O₂ to the mixture over 15 minutes, then add a solution of LiOH (36.2 g, 0.862 Mol) in 400 mL of water over a period of 30 minutes. Stir the reaction mixture at 0° C. to 5° C. for 3 h. Add a solution of 272 g of Na₂SO₃ in 850 mL of water over 70 minutes while keeping the temperature under 27° C. Distill off the bulk of the solvent under vacuum and add 7L of water. Extract with four 1.7L portions of toluene. Acidify the aqueous layers to pH 2.4 with 3N HCl. Extract with one 2.6L portion and two 1.7L portions of ethyl acetate. Combine the ethyl acetate extracts, wash with brine, dry over NaSO₄, filter, then evaporate to give the product as a white solid, 112 g.

step (e)

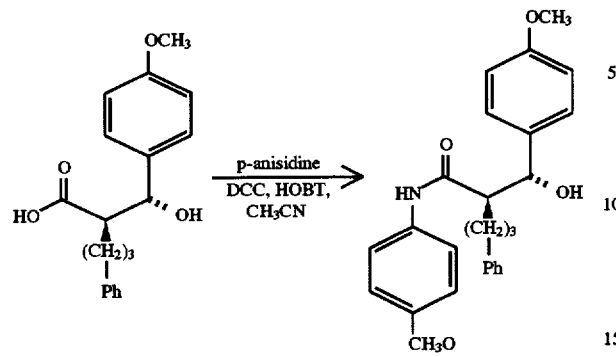

Combine the product of step (d) (19.47 g, 62 mmol), 400 mL of acetonitrile, 9.49 g (62 mmol) of 1-hydroxybenzotriazole (HOBT), 22.91 g (186 mmol) of p-anisidine and 14.05 g (68.2 mmol) of dicyclohexylcarbodiimide (DCC). Stir the reaction mixture at 40° C. for 4 h and confirm the consumption of starting material by TLC (6:4 hexane/ethyl acetate). Concentrate the mixture to ⅓ its volume and partition between 300 mL of water and 300 mL of ethyl acetate. Filter the organic layer, then wash with 200 mL of 1N HCl, then with two 100 mL portions of saturated NaHCO₃, and two 100 mL portions of bdne. Dry the organic layer over NaSO₄ and concentrate to give the product as a solid, 24 g.

step (f)

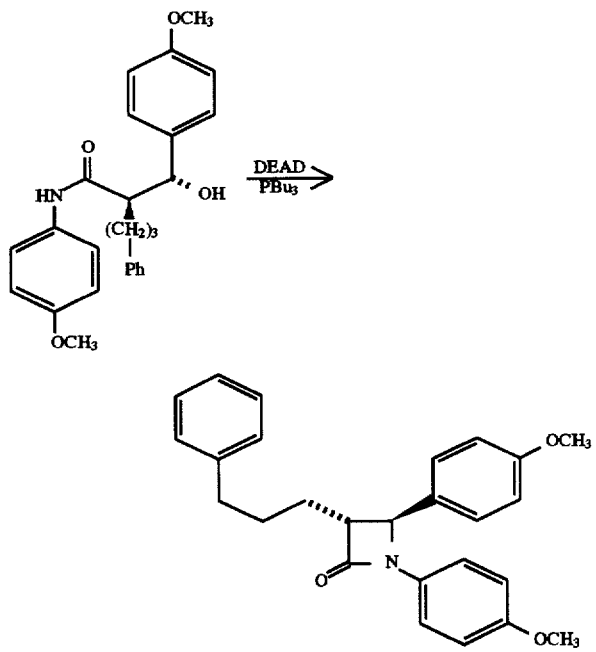

Combine the product of step (e) (115 g, 0.2745 Mol) and 2.3L of THF under dry nitrogen atmosphere and cool to −70° C. Stir the mixture and simultaneously ,add a solution of 137 mL (0.551 Mol) of tri-n-butylphosphine in 113 mL THF, and 163 mL (1.03 Mol) of diethylazodicarboxylate (DEAD) over 2 h. Allow the mixture to warm to room temperature and stir overnight. Remove the solvent under vacuum. Filter the residue through a plug of silica gel using CH₂Cl₂/hexane/ ethyl acetate (70:24:6) as the eluant. Evaporate the solvent and purify the residue by preparative HPLC (silica gel, 15% ethyl actetate/hexane) to give 88 g (80% yield) of the β-lactam product.

EXAMPLE 38

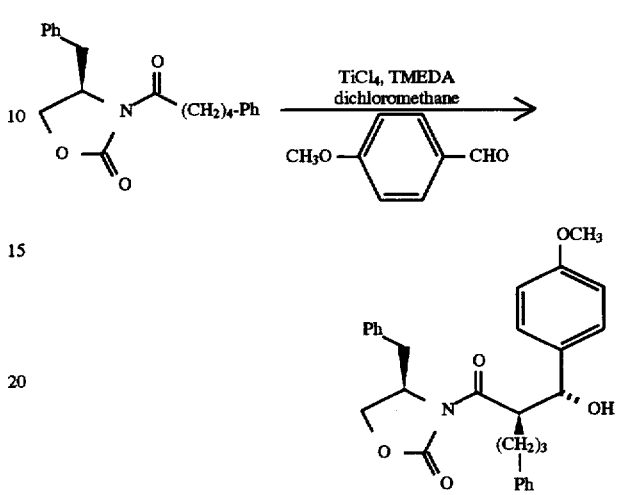

Cool a solution of 33.7 g (0.1 mol) of the product of Example 37, step (b) , in 200 mL of CH₂Cl₂ to −20° C. Stir the cold solution and add 11 mL (0.1 mol) of TiCl₄. Stir the mixture for 10 min. at −20° C., then slowly add 30 mL (2 equiv.) of tetramethylethylenediamine (TMEDA) over a period of 10 min., while keeping the temperature below −10° C. Stir the mixture at −15° to −10° C. for 70 min., then add 24 mL (2 equiv.) of p-anisaldehyde. Stir at −15° to −10° C. for 1 hour, then allow the mixture to warm to 10° C. while stirring for 40 min. Quench the reaction by adding 600 mL of 10% aqueous tartaric acid, then add 600 mL of ethyl acetate. Agitate well, then separate the layers, extracting the aqueous layer with another 200 mL of ethyl acetate. Combine the organic extracts and wash successively with water, saturated NaHCO₃ (aqueous) .and brine. Dry the organic solution over anhydrous Na₂SO₄, filter, then concentrate to a residue. Crystallize the residue from a mixture of 100 mL of ethyl acetate+210 mL of hexane to give 36.8 g of the desired compound, which can be used in step (d) of Example 37.

EXAMPLE 39

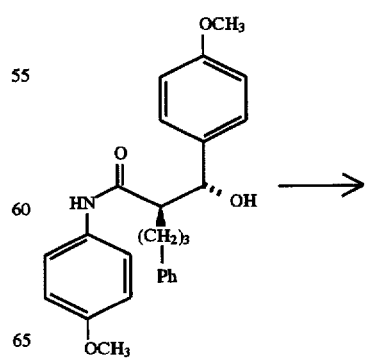

73
-continued

74
-continued

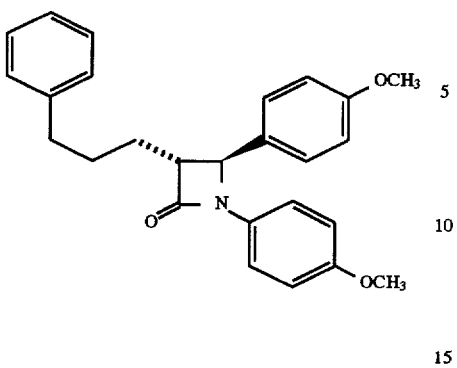

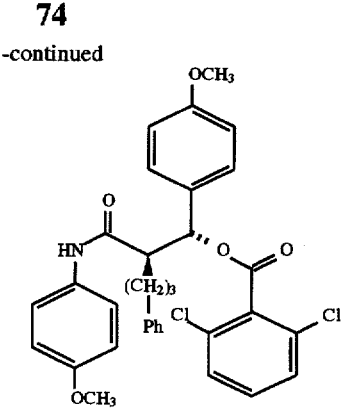

Step (a)

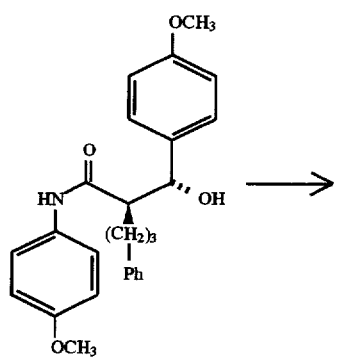

Dissolve 500 g (0.85 mol) of the product of Example 37, step(e), in 1700 mL of $CH_2Cl_2$, then add 4.0 g (12 mmol) of tera-n-butyl-ammonium hydrogen sulfate. Stir the mixture while cooling to 10° to 20° C. and add 50% aqueous NaOH (200 g). Slowly add 60 g (285 mmol) of 2,6-dichlorobenzoyl chloride to the stirred mixture over a period of 30 min. Continue stirring at 15° to 20° C. for 3 h., then pour the mixture into 2000 mL of cold water. Separate the layers and wash the organic layer with water until neutral pH is attained. Distill the methylene chloride solution to reduce the volume to 800 mL. Heat the solution to reflux and add 800 mL of heptane. Cool the hot solution to 0° C. to crystallize. Collect the product by filtration to give 116 g of the dichlorobenzoate product.

Step (b)

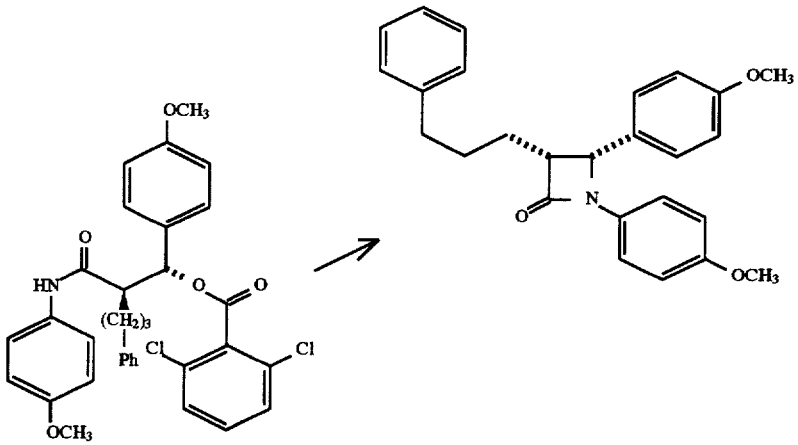

Combine 500 g (0.85 mol) of the product of step (a) with 250 g (1.1 mol) of benzyltdethylammonium chloride, 2000 mL of $CH_2Cl_2$ and 8000 mL of methyl t-butyl ether. Stir the mixture while cooling to 15° to 20° C., then add 1000 mL of 50% aqueous NaOH over a period of 10 min. Stir the mixture for 4 h., then pour into 5000 mL of water and 4 kg of ice. Separate the layers and wash the organic layer with water until the pH is neutral. Distill the solvent to reduce the volume to 2000 mL, then filter. Evaporate the flitrate to a residue and purify the residue by. chromatography on silica gel to obtain the crude product. Crystallize the product from 6 volumes of a 1:2 mixture of methyl t-butyl ether and heptane at 0° C. to give the product (240 g).

EXAMPLE 40

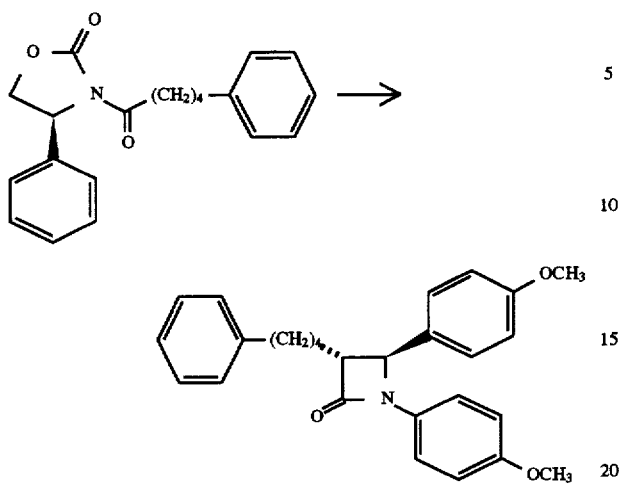

Step (a):

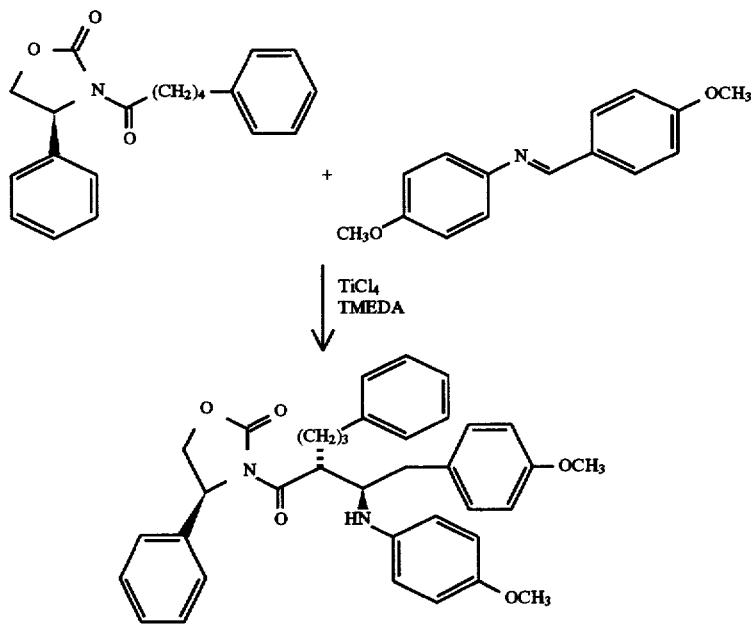

Dissolve 3.23 g (10 mmol) of the product of Example 37, step (b), in 50 mL of $CH_2Cl_2$, then stir under nitrogen atmosphere while cooling to –20° C. Add 10 mL (10 mmol) of a 1M solution of $TiCl_4$ in $CH_2Cl_2$, stir the mixture for 5 min., then add 1.5 mL (10 mmol) of TMEDA. Stir the mixture at –25° to –20° C. for 1 h., then slowly add 4.8 g (20 mmol) of the Schiff's base derived from anisaldehyde and p-anisidine as a solution in 50 mL of $CH_2Cl_2$ over a period of 30 min. Stir the mixture at –20° C. for 30 min. then gradually warm to 0° C. The reaction is monitored by HPLC (Zorbax® Sil column, 1:4 ethyl acetate/hexane), while stirring at 0° C., until complete. Quench the mixture by pouring into 50 mL of 10% aqueous tartaric acid. Extract with ethyl acetate, then wash the organic extract successively with saturated $NaHCO_3$ (aqueous) and brine. Dry the organic solution over anhydrous $Na_2SO_4$, filter, then concentrate to give the crude product. Crystallize from ethyl acetate/hexane to give the purified product.

Step (b):

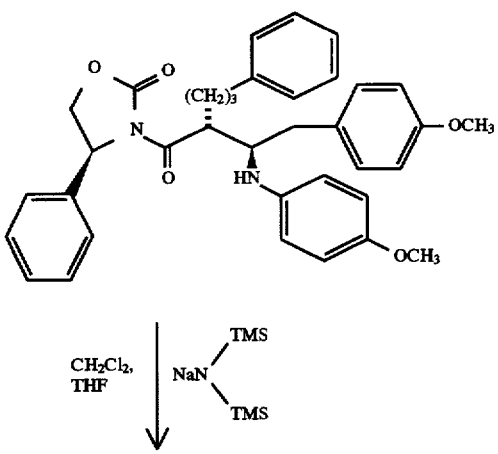

-continued

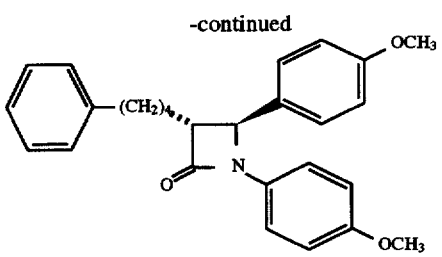

A solution of 0.505 g (0.89 mmol) of the product of step (a) in 25 mL of $CH_2Cl_2$ is stirred at 0° C., then treated with 1.77 mL (1.77 mmol) of a 1M solution of sodium bistrimethylsilylamide in THF. Stir the mixture while warming to room temperature, then continue stirring until the starting material is gone as determined by HPLC (typically 1 to 1½ h.) Quench the mixture into 10% tartaric acid (aqueous).

Wash the organic layer successively with saturated NaHCO$_3$ (aqueous) and brine, then dry over anhydrous Na$_2$SO$_4$. Filter and concentrate to give the title compound.

The following formulations exemplify some of the dosage forms of this invention. In each the term "active compound" designates a compound of formula I or II, preferably (3R, 4S)-1,4-bis-(4-methoxyphenyl)-3-(3-phenylpropyl)-2-azetidinone. However, this compound may be replaced by an equally effective amount of other compounds of formula I or II.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

Using the test procedures described above, the following in vitro and in vivo data were obtained for the preferred compounds, which are referred to in the following table by the corresponding example numbers. For the in vitro ACAT data, negative percent inhibition denotes apparent stimulation, while positive numbers denote inhibition. For the in vivo results, data is reported as percent change versus control, therefore, negative numbers indicate a positive lipid-lowering effect.

| | ACAT (in vitro) | | | % Reduction (in vivo) | | |
|---|---|---|---|---|---|---|
| Ex. | IC50 (mM) | % Inhib. | Conc. (mM) | Serum Cholest. | Cholest. Esters | Dose mg/kg |
| 1 | — | 38 | 10 | −45 | −95 | 50 |
| | | | | −17 | −55 | 10 |
| | | | | 0 | 0 | 5 |
| 1A | 7.5 | 83 | 25 | −10 | −26 | 100 |
| 1B | — | 28 | 10 | 0 | 0 | 50 |
| 1C | — | 22 | 10 | −6 | −15 | 50 |
| 1D | — | 39 | 10 | 0 | 0 | 50 |
| 1E | — | 3 | 10 | — | — | — |
| 1F | — | 61 | 10 | 0 | 20 | 50 |
| 1G | — | 21 | 10 | −11 | 0 | 50 |
| 1H | — | 57 | 10 | −21 | −51 | 50 |
| 1I | 4.5 | 81 | 10 | — | — | — |
| 1J | 3.0 | 86 | 10 | — | — | — |
| 1K | — | −70 | 10 | 0 | 0 | 50 |
| 1L | — | 20 | 10 | −31 | −75 | 50 |
| | | | | −22 | −34 | 10 |
| | | | | −25 | −30 | 5 |
| 1M | 7.0 | 80 | 10 | −11 | −31 | 25 |
| 1P | — | 39 | 10 | −19 | −54 | 50 |
| 1S | — | −19 | 10 | 0 | −32 | 85 |
| 1T | — | −11 | 10 | 0 | 0 | 50 |
| 1U | 19 | 58 | 10 | 0 | 0 | 50 |
| 1V | — | 64 | 10 | — | — | — |
| 1W | — | 9 | 10 | — | — | — |
| 1X | — | 9 | 10 | −12 | 0 | 50 |
| 1Y | — | 50 | 10 | — | — | — |
| 1Z | — | −15 | 10 | −15 | −39 | 50 |
| 1AA | — | −36 | 10 | — | — | — |
| 1AB | — | 17 | 10 | — | — | — |
| 1AC | — | 40 | 10 | −16 | −33 | 50 |
| 1AD | — | −5 | 10 | — | — | — |
| 1AE | — | −7 | 10 | — | — | — |
| 1AF | — | 0 | 10 | — | — | — |
| 1AG | — | −3 | 10 | −16 | −29 | 50 |
| 1AH | — | 4 | 10 | — | — | — |
| 1AI | — | 27 | 10 | — | — | — |
| 1AJ | — | −17 | 10 | 0 | 0 | 50 |
| 1AK | — | −33 | 10 | — | — | — |
| 1AL | — | −43 | 10 | 0 | 0 | 50 |
| 1AM | — | — | — | −12 | −29 | 50 |
| 1AN | — | — | — | −34 | −85 | 50 |
| 1AO | — | — | — | −33 | −78 | 50 |
| 1AP | — | — | — | −51 | −95 | 50 |
| 1AQ | — | — | — | −20 | −22 | 50 |
| 1AR | — | −41 | 10 | −22 | −25 | 50 |
| 1AS | 1.0 | 83 | 10 | 0 | −19 | 50 |
| 1AT | 5.0 | 70 | 10 | 0 | −28 | 50 |
| 1AU | — | 44 | 10 | 0 | −21 | 50 |
| 1AV | — | 7 | 10 | 15 | 0 | 50 |
| 1AW | — | 68 | 10 | −14 | −16 | 50 |
| 1AX | — | — | — | −16 | −52 | 50 |
| 1AY | — | — | — | −28 | −78 | 50 |
| 1AZ | — | — | — | −37 | −91 | 50 |
| 1BA | — | — | — | 0 | −0 | 50 |
| 1BB | — | −16 | 10 | 0 | 0 | 50 |
| 1BC | — | −2 | 10 | 0 | 0 | 50 |
| 1BD | — | 17 | 10 | 0 | −25 | 50 |
| 1BE | — | 30 | 10 | −10 | −21 | 50 |
| 1BF | — | −17 | 10 | 0 | −23 | 50 |
| 1BG | — | 3 | 10 | 12 | 0 | 50 |
| 1BH | — | 50 | 10 | 0− | 0 | 50 |
| 1BI | — | 59 | 10 | −17 | −45 | 50 |
| 1BJ | — | 56 | 10 | 0 | 0 | 50 |
| 1BK | — | 55 | 10 | 0 | 0 | 50 |
| 1BL | — | 42 | 10 | −10 | 0 | 50 |
| 1BM | — | 38 | 10 | 0 | −21 | 50 |
| 1BN | 7.0 | — | — | −16 | 0 | 50 |
| 1BO | 5.4 | 79 | 10 | −48 | −93 | 50 |
| 1BP | — | 58 | 10 | −9 | 0 | 50 |
| 1BQ | — | 35 | 10 | 0 | −17 | 50 |
| 1BR | — | — | — | −15 | −70 | 50 |
| 1BS | — | — | — | 0 | −43 | 50 |
| 1BT | — | — | — | 0 | 0 | 50 |
| 1BU | — | — | — | −39 | −95 | 50 |
| 1BV | — | — | — | −11 | 0 | 50 |

| | ACAT (in vitro) | | | % Reduction (in vivo) | | | | ACAT (in vitro) | | | % Reduction (in vivo) | | |
|---|---|---|---|---|---|---|---|---|---|---|---|---|---|
| Ex. | IC50 (mM) | % Inhib. | Conc. (mM) | Serum Cholest. | Cholest. Esters | Dose mg/kg | Ex. | IC50 (mM) | % Inhib. | Conc. (mM) | Serum Cholest. | Cholest. Esters | Dose mg/kg |
| 1BW | — | — | — | −9 | −29 | 50 | 5S | — | 28 | 10 | −52 | −98 | 50 |
| 1BX | — | — | — | 0 | 0 | 50 | 5T | — | — | — | −15 | −48 | 50 |
| 1BY | — | — | — | −18 | −72 | 50 | 5U | — | — | — | −48 | −86 | 50 |
| 1BZ | — | — | — | −9 | 0 | 50 | 5V | — | — | — | −37 | −77 | 50 |
| 1CA | — | — | — | −12 | 0 | 50 | 5W | — | −16 | 10 | 0 | −19 | 50 |
| 1CB | — | 33 | 10 | 0 | 0 | 50 | 5X | — | 38 | 10 | 0 | −39 | 50 |
| 1CC | — | 46 | 10 | 0 | 0 | 50 | 5Y | — | — | — | −29 | 0 | 50 |
| 1CD | 7.0 | 84 | 10 | 0 | −23 | 50 | 5Z | — | — | — | −16 | 0 | 50 |
| 1CE | — | 15 | 10 | −19 | −17 | 50 | 5AA | — | — | — | −53 | −93 | 50 |
| 1CF | — | 53 | 10 | −23 | −47 | 50 | 5AB | — | 30 | 10 | −28 | −72 | 50 |
| 1CG | — | 8 | 10 | −30 | −61 | 50 | 6 | 5 | 59 | 10 | 14 | 0 | 50 |
| 1CH | — | — | — | −49 | −95 | 50 | 7 | — | — | — | −49 | −95 | 40 |
| | | | | −41 | −90 | 10 | | | | | −41 | −89.5 | 10 |
| | | | | −24 | −80 | 3 | | | | | −30 | −50 | 3 |
| 1CI | — | 26 | 10 | −8 | −23 | 50 | 7A | — | — | — | −22 | −54 | 50 |
| 1CJ | — | — | — | 0 | 0 | 50 | 7B | — | — | — | −13 | −45 | 50 |
| 1CK | — | −12 | 10 | 0 | −28 | 50 | 7C | — | — | — | −51 | −95 | 50 |
| 1CL | — | 89 | 10 | 0 | −18 | 50 | 7D | — | — | — | −35 | −74 | 50 |
| 1CM | | | | 0 | 0 | 50 | 7E | — | — | — | −52 | −93 | 50 |
| 1CN | — | −28 | 10 | 0 | 0 | 50 | 7F | — | — | — | 0 | −26 | 50 |
| 2 | 6.0 | 82 | 10 | −15 | −37 | 5 | 7J | — | — | — | −21 | −27 | 50 |
| | | | | −28 | −69 | 10 | 7K | — | — | — | 0 | −32 | 50 |
| 2A | 25 | — | — | 0 | 0 | 50 | 7L | — | — | — | 0 | 0 | 50 |
| 3 | — | 56 | 10 | 0 | 0 | 50 | 7M | — | — | — | −38 | −94 | 50 |
| 3A | — | 33 | 10 | −12 | −29 | 50 | 7N | — | — | — | −11 | 0 | 50 |
| 3B | 6.0 | 84 | 10 | −11 | −16 | 50 | 7O | — | — | — | −14 | −20 | 50 |
| 3C | — | −18 | 10 | — | — | — | 7P | — | — | — | −40 | −95 | 50 |
| 3D | 12 | 42 | 10 | 0 | 0 | 50 | 7Q | — | — | — | −16 | 0 | 50 |
| 3E | — | −24 | 10 | 0 | 0 | 50 | 7R | — | — | — | −35 | −80 | 50 |
| 3F | 1.7 | 82 | 10 | 0 | −31 | 50 | 7S | — | — | — | −27 | −82 | 50 |
| 3G | 5.0 | 74 | 10 | 9 | 0 | 50 | 7T | — | — | — | −49 | −93 | 50 |
| 3H | — | 66 | 10 | −10 | 31 | 50 | 7U | — | — | — | −29 | −60 | 50 |
| 3I | — | 43 | 10 | −9 | 0 | 50 | 7V | — | — | — | 0 | 0 | 50 |
| 3J | — | 45 | 10 | 0 | −16 | 50 | 7W | — | — | — | 12 | 0 | 50 |
| 3K | — | 19 | 10 | 0 | 0 | 50 | 7X | — | — | — | −26 | −78 | 50 |
| 3L | — | 53 | 10 | 0 | 0 | 25 | 7Y | — | — | — | −53 | −94 | 50 |
| 3M | — | 13 | 10 | 0 | 0 | 50 | | | | | −27 | −79 | 10 |
| 3N | — | 62 | 10 | 0 | 0 | 50 | | | | | −22 | −55 | 3 |
| 3O | — | −28 | 10 | 0 | 0 | 50 | 7Z | — | — | — | −21 | −39 | 50 |
| 3Q | — | 3 | 10 | −6 | 0 | 50 | 7AA | — | — | — | −10 | −42 | 50 |
| 3R | — | −8 | 10 | 0 | 0 | 50 | 7AC | — | 31 | 10 | 0 | 0 | 50 |
| 3T | — | −9 | 10 | — | — | — | 7AD | — | −22 | 10 | −12 | −12 | 50 |
| 3U | — | 46 | 10 | 0 | 0 | 50 | 7AE | — | −95 | 10 | −17 | −10 | 50 |
| 3V | 6.5 | 60 | 10− | 0 | 0 | 50 | 7AF | — | 53 | 10 | 23 | −15 | 50 |
| 3W | — | 56 | 10 | 0 | 0 | 50 | 7AG | — | — | — | 0 | −15 | 50 |
| 3X | — | 3 | 10 | — | — | — | 7AH | — | −5 | 10 | 16 | 16 | 50 |
| 3Y | — | −33 | 10 | 0 | 0 | 50 | 7AI | — | — | — | −63 | −95 | 50 |
| 4 | — | 16 | 10 | — | — | — | | | | | −20 | −73 | 10 |
| 5 | 18 | 33 | 10 | −29 | −77.5 | 50 | | | | | −11 | −46 | 3 |
| | | | | −20 | −72 | 25 | 7AJ | — | — | — | 0 | −18 | 50 |
| | | | | −21 | −60 | 10 | 7AK | — | — | — | 12 | −28 | 50 |
| 5A | — | −70 | 10 | — | — | — | 7AL | — | — | — | −13 | 0 | 50 |
| 5C | — | 21 | 10 | −17 | −24 | 50 | 7AM | — | — | — | −24 | −70 | 50 |
| 5D | — | — | — | −38 | −95 | 50 | 7AN | — | — | — | −12 | −42 | 50 |
| | | | | −41 | −94 | 30 | 7AO | — | — | — | −41 | −90 | 50 |
| | | | | −24 | −77 | 10 | 7AP | — | — | — | −24 | −82 | 50 |
| 5E | — | — | — | −38 | −91 | 50 | 7AQ | — | — | — | −52 | −91 | 50 |
| 5F | — | — | — | −44 | −98 | 50 | 7AR | — | — | — | −32 | −88 | 50 |
| | | | | −15 | −59 | 30 | 7AS | — | — | — | 0 | −20 | 50 |
| | | | | −13 | −25 | 10 | 7AT | — | — | — | −10 | −32 | 50 |
| 5G | — | — | — | −44 | −93 | 50 | 8 | — | −12 | 10 | — | — | — |
| 5H | — | — | — | −57 | −96 | 50 | 8A | — | −17 | 10 | 0 | 0 | 50 |
| 5I | — | — | — | −26 | −70 | 50 | 8B | — | −5 | 10 | −9 | −35 | 50 |
| 5J | — | — | — | −38 | −90 | 50 | 8C | — | 63 | 10 | 0 | 0 | 50 |
| 5K | — | — | — | −28 | −49 | 50 | 8E | — | — | — | 0 | −32 | 50 |
| 5L | — | — | — | −50 | −95 | 10 | 8F | — | 8 | 10 | −16 | −48 | 50 |
| | | | | −39 | −84 | 3 | | | | | −20 | −45 | 25 |
| | | | | −54 | −64 | 1 | 9 | 26 | 30 | 20 | −43 | −93 | 10 |
| 5M | — | — | — | −8 | −36 | 10 | | | | | −21.5 | −66 | 5 |
| | | | | −12 | 0 | 3 | | | | | −25 | −68 | 3 |
| | | | | −20 | −50 | 50 | 10A | — | −37 | 10 | −19 | −58 | 50 |
| 5N | — | −23 | 10 | −17 | −55 | 50 | 11 | — | — | — | −8 | 0 | 50 |
| 5P | — | 53 | 10 | −11 | −33 | 50 | 12 | — | — | — | −12 | 0 | 50 |
| 5Q | — | −36 | 10 | 0 | −19 | 50 | 12A | — | — | — | −14 | −39 | 50 |
| 5R | — | 18 | 10 | −20 | −21 | 50 | 12B | — | — | — | 0 | −26 | 50 |

-continued

| Ex. | ACAT (in vitro) | | | % Reduction (in vivo) | | |
|---|---|---|---|---|---|---|
| | IC50 (mM) | % Inhib. | Conc. (mM) | Serum Cholest. | Cholest. Esters | Dose mg/kg |
| 12C | — | — | — | 0 | 0 | 50 |
| 12D | — | — | — | 0 | 0 | 50 |
| 13 | — | — | — | −18 | 0 | 50 |
| 14 | — | — | — | 30 | −87 | 50 |
| 14A | — | — | — | 31 | −78 | 50 |
| 14B | — | — | — | 0 | 0 | 50 |
| 14C | — | — | — | 0 | 0 | 50 |
| 15 | — | −6 | 10 | −21 | −46 | 50 |
| 15A | — | 2 | 10 | 0 | 0 | 50 |
| 15B | — | −55 | 10 | 0 | −18 | 50 |
| 16 | — | 42 | 10 | −25 | −29 | 50 |
| 16A | — | 55 | 10 | −30 | −53 | 50 |
| 17 | — | 25 | 10 | −17 | −52 | 50 |
| 17A | — | 38 | 10 | −11 | −25 | 50 |
| 17B | — | — | — | 0 | −39 | 50 |
| 18 | — | — | — | 0 | 0 | 50 |
| 19 | — | 24 | 10 | −20 | −51 | 50 |
| 19A | — | 64 | 10 | −20 | −34 | 50 |
| 19B | — | 53 | 10 | −26 | −31 | 50 |
| 19C | — | — | — | −9 | −46 | 50 |
| 19D | — | — | — | −15 | −18 | 50 |
| 19E | — | — | — | −19 | −30 | 50 |
| 20 | — | — | — | 12 | 0 | 50 |
| 21 | — | — | — | −27 | −56 | 50 |
| 21A | — | — | — | 0 | −25 | 50 |
| 22 | — | — | — | −17 | −33 | 50 |
| 22A | — | — | — | −16 | −22 | 50 |
| 23 | — | — | — | −22 | −40 | 50 |
| 24 | — | — | — | −17 | 0 | 50 |
| 24A | — | — | — | −21 | −76 | 50 |
| 25 | — | — | — | −8 | −34 | 50 |
| 25A | — | — | — | −13 | 0 | 50 |
| 25B | — | — | — | 0 | 0 | 50 |
| 25C | — | — | — | −8 | −46 | 50 |
| 26 | — | — | — | −4 | −26 | 50 |
| 27 | — | — | — | −12 | −36 | 50 |
| 27A | — | — | — | −15 | −42 | 50 |
| 28 | — | — | — | −19 | 0 | 50 |
| 29 | — | — | — | −22 | −24 | 50 |
| 31 | — | — | — | −19 | −52 | 50 |
| 31A | — | — | — | 0 | 0 | 50 |
| 32 | — | — | — | 0 | 0 | 50 |
| 32A | — | — | — | 0 | 0 | 50 |
| 33 | — | — | — | 0 | 0 | 50 |
| 34 | — | — | — | −39 | −94 | 50 |
| 35 | — | 18 | 10 | −15 | −32 | 50 |
| 35A | — | — | — | −34 | −84 | 50 |
| 35B | — | 65 | 10 | −53 | −99 | 50 |
| 36 | — | — | — | −53 | −94 | 50 |

We claim:

1. A compound having the structural formula

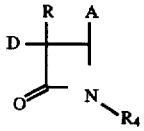

wherein

A is —$(CH_2)_p$—X—B, wherein p is 0, 1 or 2 and X is a bond;

D is B'—$(CH_2)_q$—, wherein q is 2, 3, 4, 5 or 6;

B'—$(CH_2)_e$—Z—$(CH_2)_r$—, wherein Z is —O—, e is 0, 1, 2, 3, 4 or 5 and r is 1, 2, 3, 4 or 5, provided that the sum of e and r is 1, 2, 3, 4, 5 or 6;

B'—($C_2$-$C_6$ alkenylene)—; or

B'—$(CH_2)_f$—V—$(CH_2)_g$—, wherein V is $C_3$-$C_6$ cycloalkylene, f is 1, 2, 3, 4 or 5 and g is 0, 1, 2, 3, 4 or 5, provided that the sum of f and g is 1, 2, 3, 4, 5 or 6;

B is

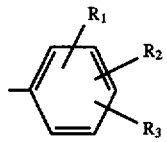

B' is

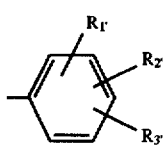

R is hydrogen;

$R_1$, $R_2$ and $R_3$ are independently selected from the group consisting of H, lower alkoxy, alkoxyalkyl, alkoxyalkoxy, alkoxycarbonyl-alkoxy, lower alkyl lower alkanedioyl, allyloxy, phenoxy, OH, m-halogeno and —$C(O)R_{12}$;

$R_{1'}$, $R_{2'}$ and $R_{3'}$ are independently selected from the group consisting of H, lower alkoxy and halogeno;

$R_4$ is

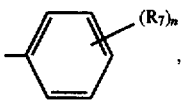

wherein n is 0, 1, 2 or 3, or indanyl;

$R_7$ is lower alkyl, lower alkoxy, halogeno, OH or —$OCF_3$, and where n is 2 or 3, the $R_7$ groups can be the same or different; and $R_{12}$ is alkoxy;

or a pharmaceutically acceptable salt thereof.

2. A pharmaceutical composition comprising a cholesterol-lowering effective amount of a compound of claim 1 and a pharmaceutically acceptable carrier.

3. A method of lowering cholesterol levels in a mammal in need of such treatment comprising administering an effective amount of a compound of claim 1.

4. A compound of claim 1 wherein D is B'—$(CH_2)_q$— wherein B' is phenyl and q is 3 or 4; B'—$(CH_2)_e$—Z—$(CH_2)_r$— wherein B' is p-fluorophenyl or p-methoxyphenyl, e is zero, Z is —O—, and r is 2; B'—($C_2$-$C_6$ alkenylene)— is 3-phenyl-1-propenyl; or B'—$(CH_2)_f$—V—$(CH_2)_g$— wherein B' is phenyl, f is 1, V is cyclopropylene, and g is zero.

5. A compound of claim 1 selected from the group consisting of compounds of the formula

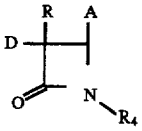

wherein D, R, A and $R_4$ and relative stereochemistry between D and A are as defined in the following table:

| Ex. | D | R | A | Relative Stereochemistry | $R_4$ |
|---|---|---|---|---|---|
| 1 | $C_6H_5-(CH_2)_3-$ | H | $p-CH_3O-C_6H_4-$ | 3S,4S | $p-CH_3O-C_6H_4-$ |
| 1L | $C_6H_5-(CH_2)_3-$ | H | $p-OH-C_6H_4-$ | 3S,4S | $p-CH_3O-C_6H_4-$ |
| 1P | $C_6H_5-(CH_2)_3-$ | H | $p-CH_3O-C_6H_4-$ | 3S,4S | $p-CH_3O-C_6H_4-$ |
| 1AN | $C_6H_5-(CH_2)_3-$ | H | $p-CH_3O-C_6H_4-$ | trans | $p-CF_3-C_6H_4-$ |
| 1AO | $C_6H_5-(CH_2)_3-$ | H | $4-CH_3O-C_6H_4-$ | cis | $p-Cl-C_6H_4-$ |
| 1AP | $C_6H_5-(CH_2)_3-$ | H | $p-CH_3O-C_6H_4-$ | cis | $p-CH_3C_6H_4-$ |
| 1AY | $C_6H_5-(CH_2)_3-$ | H | $4-((CH_3)_2CH-O)-C_6H_4-$ | cis | $p-CH_3O-C_6H_4-$ |
| 1AZ | $C_6H_5-(CH_2)_3-$ | H | $4-(CH_3(CH_2)_2-O)-C_6H_4-$ | cis | $p-CH_3O-C_6H_4-$ |
| 1BO | $C_6H_5-(CH_2)_3-$ | H | $CH_3CH_2-O-C_6H_4-$ | cis | $p-CH_3O-C_6H_4-$ |
| 1BR | $C_6H_5-(CH_2)_3-$ | H | $CH_3(CH_2)_3-O-C_6H_4-$ | cis | $p-CH_3O-C_6H_4-$ |
| 1BS | $C_6H_5-(CH_2)_3-$ | H | $4-(C_6H_5-O)-C_6H_4-$ | cis | $p-CH_3O-C_6H_4-$ |
| 1BU | $C_6H_5-(CH_2)_3-$ | H | $4-(CH_2=CH-CH_2-O)-C_6H_4-$ | cis | $p-CH_3O-C_6H_4-$ |
| 1BY | $C_6H_5-(CH_2)_3-$ | H | $4-(CH_3CH_2-O)-C_6H_4-$ | cis | $C_6H_5-$ |
| 1CG | $4-F-C_6H_4-O-(CH_2)_2-$ | H | $4-CH_3O-C_6H_4-$ | cis | $4-CH_3O-C_6H_4-$ |
| 1CH | $4-F-C_6H_4-O-(CH_2)_2-$ | H | $4-CH_3O-C_6H_4-$ | cis | $C_6H_5-$ |
| 1CP=5F | $C_6H_5-(CH_2)_3-$ | H | $4-CH_3O-C_6H_4-$ | trans | $C_6H_5-$ |
| 2 | $C_6H_5-(CH_2)_3-$ | H | $4-CH_3O-C_6H_4-$ | 3S,4S | $p-CH_3O-C_6H_4-$ |
| 5 | $C_6H_5-(CH_2)_3-$ | H | $p-CH_3O-C_6H_4-$ | 3S,4R | $p-CH_3O-C_6H_4-$ |
| 5D | $C_6H_5-(CH_2)_3-$ | H | $4-CH_3O-C_6H_4-$ | trans | $4-F-C_6H_4-$ |
| 5E | $C_6H_5-(CH_2)_3-$ | H | $4-CH_3O-C_6H_4-$ | trans | $3-CH_3O-C_6H_4-$ |
| 5G | $C_6H_5-(CH_2)_3-$ | H | $4-CH_3O-C_6H_4-$ | trans | $4-Cl-C_6H_4-$ |
| 5H | $C_6H_5-(CH_2)_3-$ | H | $4-CH_3O-C_6H_4-$ | trans | $4-(CH_3CH_2-O)-C_6H_4-$ |
| 5J | $C_6H_5-(CH_2)_3-$ | H | $4-CH_3O-C_6H_4-$ | trans | $4-CH_3-C_6H_4-$ |
| 5L | 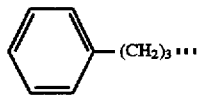 | H | 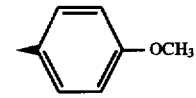 | trans | $C_6H_5-$ |
| 5M | 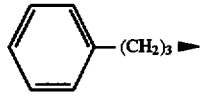 | H | 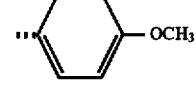 | trans | $C_6H_5-$ |
| 5S | $C_6H_5-(CH_2)_3-$ | H | $4-(CH_3CH_2-O)-C_6H_4-$ | trans | $4-CH_3O-C_6H_4-$ |
| 5U | $C_6H_5-(CH_2)_3-$ | H | $4-(CH_2=CH-CH_2-O)-C_6H_4-$ | trans | $4-CH_3O-C_6H_4-$ |
| 5V | $C_6H_5-(CH_2)_3-$ | H | $4-(C_6H_5-O)-C_6H_4-$ | trans | $4-CH_3O-C_6H_4-$ |
| 5X | $C_6H_5-O-(CH_2)_2-$ | H | $4-CH_3O-C_6H_4-$ | trans | $4-CH_3O-C_6H_4-$ |
| 5AA | $4-F-C_6H_4-O-(CH_2)_2-$ | H | $4-CH_3O-C_6H_4-$ | trans | $4-CH_3O-C_6H_4-$ |
| 5AB | $C_6H_5-(CH_2)_4-$ | H | $4-CH_3O-C_6H_4-$ | trans | $4-CH_3O-C_6H_4-$ |
| 7 | $C_6H_5-(CH_2)_3-$ | H | $4-CH_3O-C_6H_4-$ | trans | $C_6H_5-$ |
| 7E | $C_6H_5-(CH_2)_3-$ | H | $4-CH_3O-C_6H_4-$ | trans | 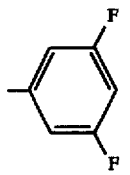 |
| 7M | $C_6H_5-(CH_2)_3-$ | H | $4-((CH_3)_2CH-O)-C_6H_4-$ | trans | $4-CH_3O-C_6H_4-$ |
| 7P | $C_6H_5-(CH_2)_3-$ | H | $4-(CH_3(CH_2)_2-O)-C_6H_4-$ | trans | $4-CH_3O-C_6H_4-$ |
| 7R | $C_6H_5-(CH_2)_3-$ | H | $4-(CH_3OC(O))-C_6H_4-$ | trans | $C_6H_5-$ |
| 7S | $C_6H_5-(CH_2)_3-$ | H | 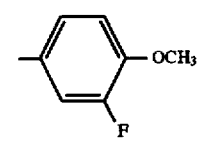 | trans | $4-CH_3O-C_6H_4-$ |
| 7T | $C_6H_5-(CH_2)_3-$ | H | $4-(CH_3OCH_2O)-C_6H_4-$ | trans | $C_6H_5-$ |
| 7X | $C_6H_5-(CH_2)_3$ | H | 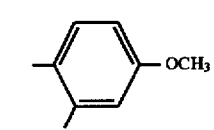 | trans | $4-CH_3O-C_6H_4-$ |
| 7Y | $C_6H_5-(CH_2)_3-$ | H | $4-(CH_3CH_2-O)-C_6H_4-$ | trans | $C_6H_5-$ |
| 7AA | $C_6H_5-(CH_2)_3-$ | H | $4-CH_3O-C_6H_4-$ | trans | $4-I-C_6H_4-$ |

-continued

| Ex. | D | R | A | Relative Stereochemistry | R4 |
|---|---|---|---|---|---|
| 7AI | 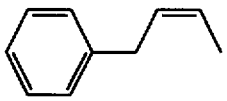 | H | 4-CH$_3$O—C$_6$H$_4$— | trans | 4-CH$_3$O—C$_6$H$_4$— |
| 7AM | C$_6$H$_5$—(CH$_2$)$_5$— | H | 4-CH$_3$O—C$_6$H$_4$— | trans | 4-CH$_3$O—C$_6$H$_4$— |
| 7AP | 4-(CH$_3$O)—C$_6$H$_4$—O—(CH$_2$)$_2$— | H | 4-CH$_3$O—C$_6$H$_4$— | trans | C$_6$H$_5$— |
| 7AR | C$_6$H$_5$—(CH$_2$)$_3$— | H | 4-CH$_3$O—C$_6$H$_4$— | trans | 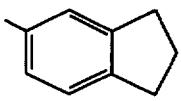 |
| 8F | C$_6$H$_5$—(CH$_2$)$_3$— | H | 4-OH—C$_6$H$_4$— | trans | 4-CH$_3$O—C$_6$H$_4$— |
| 9 | C$_6$H$_5$—(CH$_2$)$_3$— | H | 4-CH$_3$O—C$_6$H$_4$— | 3R,4S | 4-CH$_3$O—C$_6$H$_4$— |
| 10A | C$_6$H$_5$—(CH$_2$)$_3$— | H | 4-CH$_3$O—C$_6$H$_4$— | 3R,4S | 4-OH—C$_6$H$_4$— |
| 21 | C$_6$H$_5$—(CH$_2$)$_3$— | H | 4-(CH$_3$OCH$_2$)—C$_6$H$_4$— | trans | 4-CH$_3$O—C$_6$H$_4$— |
| 24A | C$_6$H$_5$—(CH$_2$)$_3$— | H | 4-(CH$_3$CH$_2$O$_2$C)—C$_6$H$_4$— | trans | 4-CH$_3$O—C$_6$H$_4$— |
| 34 | C$_6$H$_5$—(CH$_2$)$_3$— | H | —Ph—OC(CH$_2$)$_2$COCH$_3$ (with two C=O), Wherein Ph is 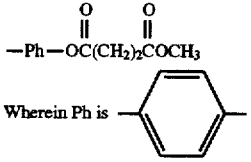 | trans | 4-CH$_3$O—C$_6$H$_4$— |
| 35A | C$_6$H$_5$—(CH$_2$)$_3$— | H | —Ph—OCH$_2$CO$_2$Et, Wherein Ph is 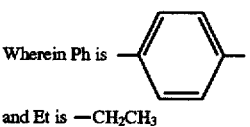 and Et is —CH$_2$CH$_3$ | 3R,4S | 4-CH$_3$O—C$_6$H$_4$— |
| 35B | C$_6$H$_5$—(CH$_2$)$_3$— | H | 4-CH$_3$O—C$_6$H$_4$— | cis | 4-(CH$_3$CH$_2$O)—C$_6$H$_4$— |
| 36 | 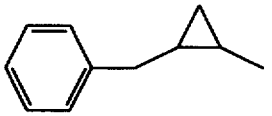 | H | 4-CH$_3$O—C$_6$H$_4$— | cis | 4-CH$_3$O—C$_6$H$_4$— |

6. A compound of claim 1 wherein p is zero and Z is a bond.

7. (3R,4S)-1,4-bis-(4-methoxyphenyl)-3-(3-phenylpropyl)-2-azetidinone.

* * * * *